US008629160B2

(12) United States Patent
Amari et al.

(10) Patent No.: US 8,629,160 B2
(45) Date of Patent: *Jan. 14, 2014

(54) ALKALOID AMINOESTER DERIVATIVES AND MEDICINAL COMPOSITION THEREOF

(75) Inventors: Gabriele Amari, Parma (IT); Mauro Riccaboni, Parma (IT); Antonio Caligiuri, Parma (IT)

(73) Assignee: Chiesi Farmaceutici S.p.A., Parma (IT)

( * ) Notice: Subject to any disclaimer, the term of this patent is extended or adjusted under 35 U.S.C. 154(b) by 223 days.

This patent is subject to a terminal disclaimer.

(21) Appl. No.: 13/165,936

(22) Filed: Jun. 22, 2011

(65) Prior Publication Data

US 2011/0311461 A1   Dec. 22, 2011

(30) Foreign Application Priority Data

Jun. 22, 2010  (EP) .................................. 10166898

(51) Int. Cl.
| | |
|---|---|
| A61K 9/12 | (2006.01) |
| A61K 31/439 | (2006.01) |
| A61P 11/00 | (2006.01) |
| A61P 11/06 | (2006.01) |
| A61P 11/08 | (2006.01) |
| C07D 453/02 | (2006.01) |

(52) U.S. Cl.
USPC .......................................... 514/305; 546/137

(58) Field of Classification Search
USPC .......................................... 546/137; 514/305
See application file for complete search history.

(56) References Cited

U.S. PATENT DOCUMENTS

| | | | |
|---|---|---|---|
| 2010/0035922 A1 | 2/2010 | Amari et al. | |
| 2010/0173880 A1 | 7/2010 | Caligiuri et al. | |
| 2011/0308519 A1* | 12/2011 | Schiaretti | 128/203.15 |
| 2011/0311458 A1* | 12/2011 | Amari et al. | 424/43 |
| 2011/0311459 A1* | 12/2011 | Amari et al. | 424/43 |
| 2012/0220557 A1* | 8/2012 | Raschini et al. | 514/171 |

FOREIGN PATENT DOCUMENTS

| | | | |
|---|---|---|---|
| EP | 2206712 | * | 7/2010 |
| WO | 03/053966 | | 7/2003 |
| WO | 2010072338 | * | 7/2010 |

OTHER PUBLICATIONS

Karakiulakis et al., Mediators of Inflammation, (2012), vol. 10, pp. 1-9.*
U.S. Appl. No. 13/303,413, filed Nov. 23, 2011, Amari, et al.
U.S. Appl. No. 13/729,388, filed Dec. 28, 2012, Amari, et al.
U.S. Appl. No. 13/232,415, filed Sep. 14, 2011, Amari, et al.
U.S. Appl. No. 13/219,109, filed Aug. 26, 2011, Amari, et al.
U.S. Appl. No. 13/165,948, filed Jun. 22, 2011, Amari, et al.
U.S. Appl. No. 13/165,930, filed Jun. 22, 2011, Amari, et al.
European Search Report in Application No. 10166898.6, issued Dec. 22, 2010.
U.S. Appl. No. 13/827,101, filed Mar. 14, 2013, Caligiuri, et al.

* cited by examiner

*Primary Examiner* — Niloofar Rahmani
(74) *Attorney, Agent, or Firm* — Oblon, Spivak, McClelland, Maier & Neustadt, L.L.P.

(57) ABSTRACT

The present invention relates to alkaloid aminoester compounds which act as muscarinic receptor antagonists, processes for their preparation, compositions comprising them, and therapeutic uses thereof.

22 Claims, No Drawings

ALKALOID AMINOESTER DERIVATIVES AND MEDICINAL COMPOSITION THEREOF

CROSS REFERENCES TO RELATED APPLICATIONS

This application claims priority to European Patent Application No. 10166898.6, filed on Jun. 22, 2010, which is incorporated herein by reference in its entirety.

BACKGROUND OF THE INVENTION

1. Field of the Invention

The present invention relates to alkaloid aminoester derivatives which act as muscarinic receptor antagonists. The present invention also relates to processes for the preparation of such an alkaloid aminoester derivative, compositions comprising such an alkaloid aminoester derivative, and therapeutic uses of such an alkaloid aminoester derivative.

2. Discussion of the Background

Quaternary ammonium salts acting as muscarinic (M) receptor antagonist drugs are currently used in therapy to induce bronchodilation for the treatment of respiratory diseases. Examples of well known M receptor antagonists are for instance represented by ipratropium bromide and tiotropium bromide.

Several chemical classes acting as selective M3 receptor antagonist drugs have been developed for the treatment of inflammatory or obstructive airway diseases such as asthma and chronic obstructive pulmonary disease (COPD).

Quinuclidine carbamate derivatives and their use as M3 antagonists are for instance disclosed in WO 02/051841, WO 03/053966, and WO 2008/012290, all of which are incorporated herein by reference in their entireties. Said M and M3 receptor antagonists are currently administered through inhalation route in order to deliver the drug directly at the site of action, thus limiting the systemic exposure and any undesirable side effect due to systemic absorption.

Therefore, it is highly desirable to provide M3 receptor antagonists able to act locally, while having high potency and long duration of action. Said drugs, once adsorbed, are degraded to inactive compounds which are deprived of any systemic side effects typical of muscarinic antagonists.

The co-pending application WO 2010/072338, which is incorporated herein by reference in its entirety, describes azonia-bicyclo[2.2.2]octane compounds acting as muscarinic receptor antagonists, further possessing the above therapeutically desirable characteristics.

There remains, however a need for muscarinic receptor antagonists with even further improved properties.

SUMMARY OF THE INVENTION

Accordingly, it is one object of the present invention to provide novel compounds which act as muscarinic receptor antagonists.

It is another object of the present invention to provide novel processes for producing such a compound.

It is another object of the present invention to provide novel pharmaceutical compositions which contain such a compound.

It is another object of the present invention to provide novel methods of treating and/or preventing certain diseases and conditions by administering an effective amount of such a compound.

These and other objects, which will become apparent during the following detailed description, have been achieved by the inventors' discovery that the presence of a heteroaryl group in the above azonia-bicyclo[2.2.2]octane derivatives, as per the details below, improves even further the duration of action of these latter compounds.

Thus, the present invention provides alkaloid aminoester derivatives of general formula (I), which act as muscarinic receptor antagonists.

In another embodiment, the present invention provides processes for the preparation of such compounds.

In another embodiment, the present invention provides pharmaceutical compositions which contain such a compound.

In another embodiment, the present invention provides methods for the treatment of respiratory disorders.

In another embodiment, the present invention provides combinations of the such a compound with other pharmaceutical active ingredients among which are, for instance, those currently used in the treatment of respiratory disorders, e.g. beta2-agonists, corticosteroids, P38 MAP kinase inhibitors, IKK2, HNE inhibitors, PDE4 inhibitor, leukotriene modulators, NSAIDs, and mucus regulators.

The compounds of the present invention thus behave as soft-drugs, since they are able to produce a more persistent bronchodilating effect in the lungs but are more consistently and rapidly transformed into inactive metabolites after passing into human plasma.

This behavior gives great advantages in terms of safety.

DETAILED DESCRIPTION OF THE PREFERRED EMBODIMENTS

In particular, the invention is directed to alkaloid aminoester derivatives of general formula (I):

(I)

wherein:

$R_1$ is selected from the group consisting of aryl, heteroaryl, aryl($C_1$-$C_6$)alkyl and heteroaryl($C_1$-$C_6$)alkyl, optionally substituted by one or more substituents selected from the group consisting of halogen atoms, —OH, oxo, —SH, —$NH_2$, —$NO_2$, —CN, —CON($R_5$)$_2$, —NHCOR$_5$, —COR$_5$, —$CO_2R_5$, ($C_1$-$C_6$)alkylsulfanyl, ($C_1$-$C_6$)alkylsulfinyl, ($C_1$-$C_6$)alkylsulfonyl, ($C_1$-$C_6$)alkyl, ($C_1$-$C_6$)haloalkyl, ($C_1$-$C_6$)alkoxy and ($C_1$-$C_6$)haloalkoxy;

$R_2$ is H or is selected from the group consisting of ($C_1$-$C_6$) alkyl, ($C_3$-$C_8$)cycloalkyl and aryl($C_1$-$C_6$)alkyl, optionally substituted by one or more substituents selected from the group consisting of halogen atoms, —OH, oxo, —SH, —$NH_2$, —$NO_2$, —CN, —CON($R_5$)$_2$, —NHCOR$_5$, —COR$_5$, —$CO_2R_5$, ($C_1$-$C_6$)alkylsulfanyl, ($C_1$-$C_6$)alkylsulfinyl, ($C_1$-$C_6$)alkylsulfonyl, ($C_1$-$C_6$)alkyl, ($C_1$-$C_6$)haloalkyl, ($C_1$-$C_6$) alkoxy and ($C_1$-$C_6$)haloalkoxy;

$R_3$ is selected from the group consisting of aryl, heteroaryl, aryl($C_1$-$C_6$)alkyl and heteroaryl($C_1$-$C_6$)alkyl, optionally substituted by one or more substituents selected from the group consisting of halogen atoms, —OH, oxo, —SH, —$NH_2$, —$NO_2$, —CN, —CON($R_5$)$_2$, —COR$_5$, —$CO_2R_5$, ($C_1$-$C_6$) alkylsulfanyl, ($C_1$-$C_6$)alkylsulfinyl, ($C_1$-$C_6$)alkylsulfonyl, ($C_1$-$C_6$)alkyl, ($C_1$-$C_6$)haloalkyl, ($C_1$-$C_6$)alkoxy and ($C_1$-$C_6$)haloalkoxy and aryl($C_1$-$C_6$)alkyl;

$R_5$ is selected, independently in each occurrence, from the group consisting of —H, ($C_1$-$C_6$)alkyl, ($C_2$-$C_6$)alkenyl, ($C_3$-$C_8$)cycloalkyl, heteroaryl and aryl optionally substituted by one or more substituents selected from the group consisting of halogen atoms, —OH, oxo, —SH, —$NH_2$, —$NO_2$, —CN, —$CONH_2$, —COOH, ($C_1$-$C_6$)alkoxycarbonyl, ($C_1$-$C_6$)alkylsulfanyl, ($C_1$-$C_6$)alkylsulfinyl, ($C_1$-$C_6$)alkylsulfonyl, ($C_1$-$C_6$)alkyl, ($C_1$-$C_6$)haloalkyl, ($C_1$-$C_6$)alkoxy and ($C_1$-$C_6$)haloalkoxy;

Q represents a group of formula (i) or (ii)

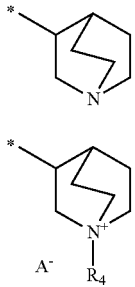

wherein $R_4$ is a group of formula (Y)

—$(CH_2)_p$—P—$(CH_2)_q$—W                     (Y)

wherein
p is 0 or an integer of 1 to 4;
q is 0 or an integer of 1 to 4;
P is absent or is selected from the group consisting of —O—, —S—, —SO—, —$SO_2$—, —CO—, —$NR_5$—, —CH=CH—, —$N(R_5)SO_2$—, —$N(R_5)COO$—, —$N(R_5)C(O)$—, —$SO_2N(R_5)$—, —$CO(O)N(R_5)$—, and —$C(O)N(R_5)$—;
W is selected from the group consisting of —H, ($C_1$-$C_6$)alkyl, ($C_2$-$C_6$)alkenyl, ($C_3$-$C_8$)cycloalkyl, aryl and heteroaryl, optionally substituted by one or more substituents selected from the group consisting of halogen atoms, —OH, oxo, —SH, —$NH_2$, —$NO_2$, —CN, —$CON(R_5)_2$, —$NHCOR_5$, —$COR_5$, —$CO_2R_5$, ($C_1$-$C_6$)alkyl, ($C_1$-$C_6$)alkylsulfanyl, ($C_1$-$C_6$)alkylsulfinyl, ($C_1$-$C_6$)alkylsulfonyl, ($C_1$-$C_6$)alkyl, ($C_1$-$C_6$)haloalkyl, ($C_1$-$C_6$)alkoxy and ($C_1$-$C_6$)haloalkoxy;
$A^-$ is a physiologically acceptable anion;
and pharmaceutically acceptable salts thereof;
wherein at least one between $R_1$ and $R_3$ is a heteroaryl group.

In the present description, unless otherwise provided, the term "halogen" includes fluorine, chlorine, bromine and iodine atom or atoms.

The expression "($C_1$-$C_6$)alkyl" refers to straight or branched chain alkyl groups wherein the number of carbon atoms is from 1 to 6. Examples of said groups are methyl, ethyl, n-propyl, isopropyl, n-butyl, isobutyl, sec-butyl, tert-butyl, pentyl, hexyl and the like.

The derived expression "($C_1$-$C_6$)alkoxy" should be construed in an analogous manner as referring to the above alkyloxy (e.g. alkoxy) groups. Examples of said groups may thus comprise methoxyl, ethoxyl, n-propoxyl, isopropoxyl, n-butoxyl, isobutoxyl, sec-butoxyl, tert-butoxyl, pentoxyl, hexoxyl and the like.

Likewise, the expression "($C_1$-$C_6$)alkoxycarbonyl" should be construed as referring to the above ($C_1$-$C_6$)alkoxy groups further bearing a carbonyl group among which is, for instance, acetoxy (e.g. acetyloxycarbonyl), tert-butoxycarbonyl, and the like.

The derived expressions "($C_1$-$C_6$)haloalkyl" and "($C_1$-$C_6$)haloalkoxy", thus refer to the above "($C_1$-$C_6$)alkyl" and "($C_1$-$C_6$)alkoxy" groups wherein one or more hydrogen atoms are replaced by one or more, the same or different from each other, halogen atoms.

Examples of the said ($C_1$-$C_6$)haloalkyl and ($C_1$-$C_6$)haloalkoxy groups may thus include halogenated, poly-halogenated and even fully halogenated alkyl and alkoxy groups wherein all of the hydrogen atoms are replaced by halogen atoms. Among these latter are, as an example, trifluoromethyl or trifluoromethoxyl groups.

Likewise, the derived expressions "($C_1$-$C_6$)alkylsulfanyl", "($C_1$-$C_6$)alkylsulfinyl" or "($C_1$-$C_6$)alkylsulfonyl" refer, respectively, to alkyl-S—, alkyl-SO— or alkyl-$SO_2$— groups.

The expression "($C_3$-$C_8$)cycloalkyl", refers to cyclic non-aromatic hydrocarbon groups with from 3 to 8 carbon atoms. Examples include cyclopropyl, cyclobutyl, cyclopentyl, cyclohexyl, cycloheptyl, and the like.

The expression "aryl" refers to mono or bi- or tricyclic ring systems which have 6 to 20 ring atoms, preferably from 6 to 15 and wherein at least one ring is aromatic.

The expression "heteroaryl" refers to mono, bi- or tricyclic ring systems which have 5 to 20 ring atoms, preferably from 5 to 15, in which at least one ring is aromatic and in which at least one ring atom is a heteroatom or heteroaromatic group (e.g. N, NH, S or O).

Examples of suitable aryl or heteroaryl monocyclic systems include, for instance, thiophene (thiophenyl), benzene (phenyl), pyrrole (pyrrolyl), pyrazole (pyrazolyl), imidazole (imidazolyl), isoxazole (isoxazolyl), oxazole (oxazolyl), isothiazole (isothiazolyl), thiazole (thiazolyl), pyridine (pyridinyl), imidazolidine (imidazolidinyl), furan (furanyl) radicals and the like.

Examples of suitable aryl or heteroaryl bicyclic systems include naphthalene (naphthyl), biphenyl (biphenylyl), purine (purinyl), pteridine (pteridinyl), benzotriazole (benzotriazolyl), quinoline (quinolinyl), isoquinoline (isoquinolinyl), indole (indolyl), isoindole (isoindolyl), benzothiophene (benzothiophenyl), dihydrobenzo dioxin, dihydrobenzo dioxepin, benzo oxazin radicals, and the like.

Examples of suitable aryl or heteroaryl tricyclic systems include fluorene (fluorenyl) radicals as well as benzocondensed derivatives of the aforementioned heteroaryl bicyclic systems.

The expressions "aryl($C_1$-$C_6$)alkyl", "heteroaryl($C_1$-$C_6$)alkyl, refer to ($C_1$-$C_6$)alkyl groups further substituted by aryl or heteroaryl rings, respectively.

The expression "aryl($C_1$-$C_6$)alkoxy" refer to ($C_1$-$C_6$)alkoxy further substituted by aryl.

The expression "($C_2$-$C_6$)alkenyl" refers to straight or branched carbon chains with one or more double bonds. Examples of said groups may thus comprise ethenyl, propenyl, butenyl, pentenyl, hexenyl, and the like.

As far as $R_5$ is concerned, it is clear to the skilled person that, in any possible occurrence, it may represent —H or a group among those formerly reported.

Hence, just as an example, in case $R_1$ is an aryl group further substituted by —$CON(R_5)_2$ group, this latter also includes —$CONH_2$, —$CONHR_5$ and —$CON(R_5)(R_5)$, wherein $R_5$ is as set forth above.

Advantageously, physiologically acceptable anions $A^-$ include those selected from chloride, bromide, iodide, trifluoroacetate, formate, sulfate, phosphate, methanesulfonate, nitrate, maleate, acetate, citrate, fumarate, tartrate, oxalate, succinate, benzoate, and p-toluenesulfonate, preferably chloride, bromide, and trifluoroacetate.

Besides the presence of $A^-$ anion, whenever further basic amino groups are present within the compounds of formula (I), additional physiological acceptable anions, among those formerly indicated, may be present. Likewise, in the presence of acidic groups such as COOH groups, corresponding physiological cation salts may be present as well, for instance including alkali or earth-alkali metal ions.

A first group of compounds of general formula (I) is that wherein $R_1$ is selected from the group consisting of aryl, heteroaryl and aryl($C_1$-$C_6$)alkyl, optionally substituted by one or more substituents selected from the group consisting of halogen atoms, —$COR_5$, —$CO_2R_5$, —$CON(R_5)_2$, ($C_1$-$C_6$)alkyl, and ($C_1$-$C_6$)alkoxy; $R_2$ is H or ($C_1$-$C_6$)alkyl; Q is a group of formula (i); and $R_3$ and $R_5$ have the above reported meanings.

Still more preferred, within this class, are the compounds of general formula (I), wherein $R_1$ is selected from the group consisting of phenyl, benzyl and thiophenyl, optionally substituted by one or more substituents selected from the group consisting of halogen atoms, —$COR_5$, —$CO_2R_5$, —$CON(R_5)_2$, ($C_1$-$C_6$)alkyl, and ($C_1$-$C_6$)alkoxy, wherein $R_5$ is H or ($C_1$-$C_6$)alkyl; Q is a group of formula (i); $R_2$ is H or methyl; and $R_3$ has the above reported meaning.

A second group of compounds of general formula (I) is that wherein $R_1$ is selected from the group consisting of aryl, heteroaryl and aryl($C_1$-$C_6$)alkyl, optionally substituted by one or more substituents selected from the group consisting of halogen atoms, —$COR_5$, —$CO_2R_5$, —$CON(R_5)_2$, ($C_1$-$C_6$)alkyl, and ($C_1$-$C_6$)alkoxy; $R_2$ is H or ($C_1$-$C_6$)alkyl; Q is a group of formula (ii); and $R_3$, $R_4$, $R_5$ and $A^-$ have the above reported meanings.

Still more preferred, within this class, are the compounds of general formula (I), wherein $R_1$ is selected from the group consisting of phenyl, benzyl and thiophenyl, optionally substituted by one or more substituents selected from the group consisting of halogen atoms, —$COR_5$, —$CO_2R_5$, —$CON(R_5)_2$, ($C_1$-$C_6$)alkyl, and ($C_1$-$C_6$)alkoxy, wherein $R_5$ is H or ($C_1$-$C_6$)alkyl; Q is a group of formula (ii); $R_2$ is H or methyl; and $R_3$, $R_4$ and $A^-$ have the above reported meanings.

Another preferred group of compounds of general formula (I) is that wherein $R_3$ is selected from the group consisting of aryl and heteroaryl, optionally substituted by one or more substituents selected from the group consisting of halogen atoms, ($C_1$-$C_6$)alkoxy, —OH, and ($C_1$-$C_6$)arylalkoxy; Q is a group of formula (i); $R_2$ is H or ($C_1$-$C_6$)alkyl; and $R_1$ and $R_5$ have the above reported meanings.

An even more preferred group of compounds of general formula (I), within this class, is that wherein $R_3$ is selected from the group consisting of phenyl, pyridyl, thiophenyl and benzothiophenyl, optionally substituted as above indicated; Q is a group of formula (i); and $R_2$ is H or methyl; and $R_5$ has the above reported meaning.

Another preferred group of compounds of general formula (I) is that wherein $R_3$ is selected from the group consisting of aryl and heteroaryl, optionally substituted by one or more substituents selected from the group consisting of halogen atoms, ($C_1$-$C_6$)alkoxy, —OH and ($C_1$-$C_6$)arylalkoxy; Q is a group of formula (ii); $R_2$ is H or ($C_1$-$C_6$)alkyl; and $R_1$, $R_4$, $R_5$ and $A^-$ have the above reported meanings.

An even more preferred group of compounds of general formula (I), within this class, is that wherein $R_3$ is selected from the group consisting of phenyl, pyridyl, thienyl and benzothiophenyl, optionally substituted as above indicated; Q is a group of formula (ii); $R_2$ is H or methyl; and $R_1$, $R_4$ and $A^-$ have the above reported meanings.

Another preferred group of compounds of general formula (I) is that wherein Q is a group of formula (ii); $R_4$ is a group of formula (Y) wherein p is 0, 1, 2 or 3, q is 0, P is absent or is selected from the group consisting of —O—, —CO— and —C(O)N($R_5$)— and W is selected from the group consisting of aryl, ($C_2$-$C_6$)alkenyl and heteroaryl, optionally substituted by one or more substituents as above indicated; and $R_1$, $R_2$, $R_3$, $R_5$ and $A^-$ have the above reported meanings.

Still more preferred, within this class, are the compounds of general formula (I), wherein Q is a group of formula (ii); p is 1, q is 0, P is —CO— and W is selected from the group consisting of phenyl, pyridyl, thiophenyl, isoxazolyl and thiazolyl, optionally substituted as above described; and $R_1$, $R_2$, $R_3$, $R_5$ and $A^-$ have the above reported meanings.

Even still more preferred within this class are the compound of general formula (I), wherein Q is a group of formula (ii); p is 3, q is 0, P is O and W is phenyl optionally substituted as above described; and $R_1$, $R_2$, $R_3$, $R_5$ and A have the above reported meanings.

Even still more preferred within this class are the compound of general formula (I), wherein Q is a group of formula (ii); p is 2, q is 0, P is absent and W is phenyl optionally substituted as above described; and $R_1$, $R_2$, $R_3$, $R_5$ and A have the above reported meanings.

Even still more preferred within this class are the compound of general formula (I), wherein Q is a group of formula (ii); p is 1, q is 0, P is —CON(H)— and W is pyridyl optionally substituted as above described; and $R_1$, $R_2$, $R_3$, $R_5$ and $A^-$ have the above reported meanings.

Still more preferred within this class are the compound of general formula (I), wherein Q is a group of formula (ii); p and q are 0, P is absent and W is methyl; and $R_1$, $R_2$, $R_3$, $R_5$ and $A^-$ have the above reported meanings.

According to specific embodiments, the present invention provides, as an example, the compounds reported below:

| Compound | Chemical name |
| --- | --- |
| C2 | (R)-quinuclidin-3-yl 2-(6-methoxypyridin-3-yl)-2-(phenylamino)acetate |
| C3 | (3R)-3-(2-(6-methoxypyridin-3-yl)-2-(phenylamino)acetoxy)-1-(2-oxo-2-phenylethyl)-1-azoniabicyclo[2.2.2]octane trifluoroacetate |
| C5 | (2-acetyl-thiophen-3-ylamino)-phenyl-acetic acid (R)-(1-aza-bicyclo[2.2.2]oct-3-yl) ester |
| C6 | (3R)-3-(2-(2-acetylthiophen-3-ylamino)-2-phenylacetoxy)-1-(2-oxo-2-phenylethyl)-1-azoniabicyclo[2.2.2]octane trifluoroacetate |
| C8 | (R)-quinuclidin-3-yl 2-(2-carbamoylthiophen-3-ylamino)-2-phenylacetate |
| C9 | (3R)-3-(2-(2-carbamoylthiophen-3-ylamino)-2-phenylacetoxy)-1-(2-oxo-2-phenylethyl)-1-azoniabicyclo[2.2.2]octane 2,2,2-trifluoroacetate |
| C11 | 3-(2-oxo-1-phenyl-2-((R)-quinuclidin-3-yloxy)ethylamino)thiophene-2-carboxylate |

-continued

| Compound | Chemical name |
|---|---|
| C12 | (3R)-3-(2-(2-(methoxycarbonyl)thiophen-3-ylamino)-2-phenylacetoxy)-1-(2-oxo-2-(thiazol-2-yl)ethyl)-1-azoniabicyclo[2.2.2]octane trifluoroacetate |
| C13 | (3R)-1-(2-(4-hydroxyphenyl)-2-oxoethyl)-3-(2-(2-(methoxycarbonyl)thiophen-3-ylamino)-2-phenylacetoxy)-1-azoniabicyclo[2.2.2]octane bromide |
| C14 | (3R)-3-(2-(2-(methoxycarbonyl)thiophen-3-ylamino)-2-phenylacetoxy)-1-(2-oxo-2-(thiophen-3-yl)ethyl)-1-azoniabicyclo[2.2.2]octane bromide |
| C15 | (3R)-3-(2-(2-(methoxycarbonyl)thiophen-3-ylamino)-2-phenylacetoxy)-1-(3-phenoxypropyl)-1-azoniabicyclo[2.2.2]octane bromide |
| C16 | (3R)-3-(2-(2-(methoxycarbonyl)thiophen-3-ylamino)-2-phenylacetoxy)-1-(2-oxo-2-(pyridin-2-yl)ethyl)-1-azoniabicyclo[2.2.2]octane 2,2,2-trifluoroacetate 2,2,2-trifluoroacetate anion |
| C17 | (3R)-1-(4-fluorophenethyl)-3-(2-(2-(methoxycarbonyl)thiophen-3-ylamino)-2-phenylacetoxy)-1-azoniabicyclo[2.2.2]octane 2,2,2-trifluoroacetate |
| C19 | (R)-quinuclidin-3-yl 2-(benzo[b]thiophen-3-yl)-2-(phenylamino)acetate |
| C20 | (3R)-3-(2-(benzo[b]thiophen-3-yl)-2-(phenylamino)acetoxy)-1-(2-oxo-2-(thiophen-2-yl)ethyl)-1-azoniabicyclo[2.2.2]octane bromide |
| C21 | (3R)-3-(2-(benzo[b]thiophen-3-yl)-2-(phenylamino)acetoxy)-1-(2-oxo-2-phenylethyl)-1-azoniabicyclo[2.2.2]octane trifluoroacetate |
| C22 | (R)-3-(2-(benzo[b]thiophen-3-yl)-2-(phenylamino)acetoxy)-1-(2-(4-hydroxyphenyl)-2-oxoethyl)-1-azoniabicyclo[2.2.2]octane bromide |
| C23 | (R)-3-(2-(benzo[b]thiophen-3-yl)-2-(phenylamino)acetoxy)-1-(2-oxo-2-(pyridin-2-ylamino)ethyl)-1-azoniabicyclo[2.2.2]octane chloride |
| C24 | (R)-3-(2-(benzo[b]thiophen-3-yl)-2-(phenylamino)acetoxy)-1-(2-oxo-2-(thiophen-3-yl)ethyl)-1-azoniabicyclo[2.2.2]octane bromide |
| C25 | (R)-3-(2-(benzo[b]thiophen-3-yl)-2-(phenylamino)acetoxy)-1-(2-oxo-2-(thiazol-2-yl)ethyl)-1-azoniabicyclo[2.2.2]octane bromide |
| C27 | (R)-quinuclidin-3-yl 2-(benzo[b]thiophen-7-yl)-2-(phenylamino)acetate |
| C28 | (3R)-3-(2-(benzo[b]thiophen-7-yl)-2-(phenylamino)acetoxy)-1-(2-oxo-2-phenylethyl)-1-azoniabicyclo[2.2.2]octane chloride |
| C29 | (3R)-3-(2-(benzo[b]thiophen-7-yl)-2-(phenylamino)acetoxy)-1-(2-oxo-2-(thiophen-2-yl)ethyl)-1-azoniabicyclo[2.2.2]octane chloride |
| C31 | (R)-quinuclidin-3-yl 2-(benzo[b]thiophen-2-yl)-2-(phenylamino)acetate |
| C32 | (3R)-3-(2-(benzo[b]thiophen-2-yl)-2-(phenylamino)acetoxy)-1-(2-oxo-2-phenylethyl)-1-azoniabicyclo[2.2.2]octane 2,2,2-trifluoroacetate |
| C33 | (3R)-3-(2-(benzo[b]thiophen-2-yl)-2-(phenylamino)acetoxy)-1-(2-oxo-2-(thiazol-2-yl)ethyl)-1-azoniabicyclo[2.2.2]octane 2,2,2-trifluoroacetate |
| C35 | (R)-quinuclidin-3-yl 2-(benzo[b]thiophen-3-yl)-2-(methyl(phenyl)amino)acetate |
| C36 | (3R)-3-(2-(benzo[b]thiophen-3-yl)-2-(methyl(phenyl)amino)acetoxy)-1-(2-oxo-2-phenylethyl)-1-azoniabicyclo[2.2.2]octane chloride |
| C38 | (R)-quinuclidin-3-yl 2-(benzo[b]thiophen-3-yl)-2-(benzylamino)acetate |
| C39 | (3R)-3-(2-(benzo[b]thiophen-3-yl)-2-(benzylamino)acetoxy)-1-(2-oxo-2-phenylethyl)-1-azoniabicyclo[2.2.2]octane 2,2,2-trifluoroacetate 2,2,2-trifluoroacetate anion |
| C41 | (R)-quinuclidin-3-yl 2-(benzo[b]thiophen-3-yl)-2-(3-fluorophenylamino)acetate |
| C42 | (3R)-3-(2-(benzo[b]thiophen-3-yl)-2-(3-fluorophenylamino)acetoxy)-1-(2-oxo-2-phenylethyl)-1-azoniabicyclo[2.2.2]octane 2,2,2-trifluoroacetate |
| C44 | (R)-quinuclidin-3-yl 2-(benzo[b]thiophen-3-yl)-2-(2-ethylphenylamino)acetate |
| C45 | (3R)-3-(2-(benzo[b]thiophen-3-yl)-2-(2-ethylphenylamino)acetoxy)-1-(2-oxo-2-phenylethyl)-1-azoniabicyclo[2.2.2]octane bromide |
| C47 | Preparation of (R)-quinuclidin-3-yl 2-(benzo[b]thiophen-3-yl)-2-(3-methoxyphenylamino)acetate |
| C48 | (3R)-3-(2-(benzo[b]thiophen-3-yl)-2-(3-methoxyphenylamino)acetoxy)-1-(2-oxo-2-phenylethyl)-1-azoniabicyclo[2.2.2]octane 2,2,2-trifluoroacetate |
| C50 | 3-(1-(benzo[b]thiophen-3-yl)-2-oxo-2-((R)-quinuclidin-3-yloxy)ethylamino)benzoate |
| C51 | (3R)-3-(2-(benzo[b]thiophen-3-yl)-2-(3-(ethoxycarbonyl)phenylamino)acetoxy)-1-(2-oxo-2-phenylethyl)-1-azoniabicyclo[2.2.2]octane 2,2,2-trifluoroacetate |
| C53 | (R)-quinuclidin-3-yl 2-(6-(benzyloxy)pyridin-3-yl)-2-(phenylamino)acetate |
| C54 | (R)-3-(2-(6-(benzyloxy)pyridin-3-yl)-2-(phenylamino)acetoxy)-1-(2-oxo-2-phenylethyl)-1-azoniabicyclo[2.2.2]octane 2,2,2-trifluoroacetate |
| C55 | (3R)-3-(2-(6-hydroxypyridin-3-yl)-2-(phenylamino)acetoxy)-1-(2-oxo-2-phenylethyl)-1-azoniabicyclo[2.2.2]octane 2,2,2-trifluoroacetate |
| C57 | (R)-quinuclidin-3-yl 2-(4-methoxyphenylamino)-2-(thiophen-3-yl)acetate |
| C58 | (3R)-3-(2-(4-methoxyphenylamino)-2-(thiophen-3-yl)acetoxy)-1-(2-oxo-2-phenylethyl)-1-azoniabicyclo[2.2.2]octane 2,2,2-trifluoroacetate |
| C60 | (R)-methyl 3-(1-(6-methoxypyridin-3-yl)-2-oxo-2-(quinuclidin-3-yloxy)ethylamino)thiophene-2-carboxylate |
| C61 | (R)-3-(2-(2-(methoxycarbonyl)thiophen-3-ylamino)-2-(6-methoxypyridin-3-yl)acetoxy)-1-(2-oxo-2-phenylethyl)-1-azoniabicyclo[2.2.2]octane 2,2,2-trifluoroacetate |
| C62 | (R)-3-(2-(2-(methoxycarbonyl)thiophen-3-ylamino)-2-(6-methoxypyridin-3-yl)acetoxy)-1-(2-oxo-2-(thiazol-2-yl)ethyl)-1-azoniabicyclo[2.2.2]octane 2,2,2-trifluoroacetate |

| Compound | Chemical name |
|---|---|
| C63 | (3R)-3-(2-(2-(methoxycarbonyl)thiophen-3-ylamino)-2-(6-methoxypyridin-3-yl)acetoxy)-1-(2-oxo-2-(thiophen-2-yl)ethyl)-1-azoniabicyclo[2.2.2]octane 2,2,2-trifluoroacetate |
| C65 | ethyl 3-(1-(6-methoxypyridin-3-yl)-2-oxo-2-((R)-quinuclidin-3-yloxy)ethylamino)benzoate |
| C66 | (3R)-3-(2-(3-(ethoxycarbonyl)phenylamino)-2-(6-methoxypyridin-3-yl)acetoxy)-1-(2-oxo-2-phenylethyl)-1-azoniabicyclo[2.2.2]octane chloride |
| C67 | (3R)-3-(2-(3-(ethoxycarbonyl)phenylamino)-2-(6-methoxypyridin-3-yl)acetoxy)-1-(2-oxo-2-(thiophen-2-yl)ethyl)-1-azoniabicyclo[2.2.2]octane chloride |
| C68 | (3R)-3-(2-(3-(ethoxycarbonyl)phenylamino)-2-(6-methoxypyridin-3-yl)acetoxy)-1-(2-(4-hydroxyphenyl)-2-oxoethyl)-1-azoniabicyclo[2.2.2]octane bromide |
| C69 | (3R)-3-(2-(3-(ethoxycarbonyl)phenylamino)-2-(6-methoxypyridin-3-yl)acetoxy)-1-(2-oxo-2-(thiazol-2-yl)ethyl)-1-azoniabicyclo[2.2.2]octane bromide |
| C70 | (3R)-3-(2-(3-(ethoxycarbonyl)phenylamino)-2-(6-methoxypyridin-3-yl)acetoxy)-1-(2-(isoxazol-3-ylamino)-2-oxoethyl)-1-azoniabicyclo[2.2.2]octane chloride |
| C71 | (3R)-3-(2-(3-(ethoxycarbonyl)phenylamino)-2-(6-methoxypyridin-3-yl)acetoxy)-1-methyl-1-azoniabicyclo[2.2.2]octane iodide |
| C72 | (3R)-3-(2-(3-(ethoxycarbonyl)phenylamino)-2-(6-methoxypyridin-3-yl)acetoxy)-1-(3-methylbut-2-enyl)-1-azoniabicyclo[2.2.2]octane bromide |
| C74 | (R)-quinuclidin-3-yl 2-(3-ethylphenylamino)-2-(6-methoxypyridin-3-yl)acetate |
| C75 | (3R)-3-(2-(3-ethylphenylamino)-2-(6-methoxypyridin-3-yl)acetoxy)-1-(2-oxo-2-phenylethyl)-1-azoniabicyclo[2.2.2]octane chloride |
| C77 | (R)-quinuclidin-3-yl 2-(3-fluorophenylamino)-2-(6-methoxypyridin-3-yl)acetate |
| C78 | (3R)-3-(2-(3-fluorophenylamino)-2-(6-methoxypyridin-3-yl)acetoxy)-1-(2-oxo-2-phenylethyl)-1-azoniabicyclo[2.2.2]octane chloride |
| C80 | methyl 2-(1-(6-methoxypyridin-3-yl)-2-oxo-2-((R)-quinuclidin-3-yloxy)ethylamino)benzoate |
| C81 | (3R)-3-(2-(2-(methoxycarbonyl)phenylamino)-2-(6-methoxypyridin-3-yl)acetoxy)-1-(2-oxo-2-phenylethyl)-1-azoniabicyclo[2.2.2]octane chloride |

The compounds of general formula (I) show at least two chiral centers, which are represented by the carbon atoms denoted with one asterisk in the following

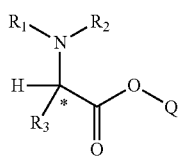
(I)

and with the other one represented below, depending whether Q represents a group of formula

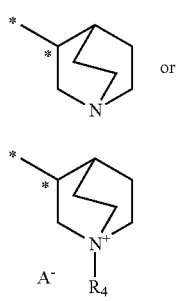

Further, depending from any of the meanings provided to $R_1$, $R_2$, $R_3$ and $R_4$, among those formerly reported, it will be clear to the skilled person that additional asymmetric centers may be present within the compounds of general formula (I). Therefore the invention also includes any of the optical stereoisomers, diastereoisomers and mixtures thereof, in any proportion.

In one of the preferred embodiments the chiral center on the quinuclidine ring shows a R configuration.

In the present invention, since the absolute configuration of the diastereoisomers is not defined, they are indicated in the examples as diastereoisomer 1, 2, or mixtures of them.

The present invention also provides pharmaceutical compositions of compounds of general formula (I) alone or in combination or in admixture with one or more pharmaceutically acceptable carriers and/or excipients.

The present invention also provides pharmaceutical compositions suitable for administration by inhalation such as, for instance, inhalable powders, propellant-containing metering aerosols or propellant-free inhalable formulations.

The present invention also provides compounds of general formula (I) for use as a medicament.

The present invention also provides compounds of general formula (I) for use in the treatment of broncho-obstructive or inflammatory diseases, preferably asthma or chronic bronchitis or chronic obstructive pulmonary disease (COPD).

In a further aspect, the present invention provides the use of the compounds of formula (I) for the manufacture of a medicament for the prevention and/or treatment of broncho-obstructive or inflammatory diseases, preferably asthma or chronic bronchitis or chronic obstructive pulmonary disease (COPD).

The present invention also provides methods for the prevention and/or treatment of broncho-obstructive or inflammatory diseases, preferably asthma or chronic bronchitis or chronic obstructive pulmonary disease (COPD), which comprises administering to a subject in need thereof a therapeutically effective amount of a compound of general formula (I).

The present invention also provides devices which may be a single- or multi-dose dry powder inhaler, a metered dose inhaler and a soft mist nebulizer comprising the compounds of general formula (I).

The present invention also provides kits comprising the above pharmaceutical compositions in a suitable vial or container and a device which may be a single- or multi-dose dry powder inhaler, a metered dose inhaler and a soft mist nebulizer, adapted to hold the above vial or container.

The compounds of general formula (I) may be prepared according to methods whose reactions and operative conditions are known or evident to a person skilled in the art.

The present invention is also directed to a process for the preparation of a compound of general formula (I) which comprises:

(a) the coupling of alcohol (IX)

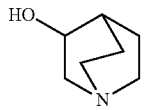
(IX)

with a compound of formula (VIII) to give a compound of general formula (I)

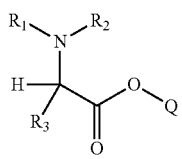
(I)

wherein Q has formula (i);

(b) the optional alkylation of the compound of general formula (I) by an alkylating agent of general formula (X)

A-R$_4$      (X)

in which A is a leaving group selected from the group consisting of halide and sulfonate ester and R$_4$ is as above described, to obtain compounds of general formula (I) wherein Q has formula (ii) and;

(c) optionally, the conversion of the compound of general formula (I) into another compound of general formula (I) and/or into a pharmaceutically acceptable salt thereof.

The present invention is also directed to processes, suitable for the preparation of the intermediate compounds of general formula (VIII), (VIII)

which are reported in the following:

Route A. The process comprises the alkylation of an amine compound of general formula (II) wherein R$_1$ and R$_2$ have the above reported meanings (II)

with a compound of general formula (III)

(III)

in which LG is a leaving group and K may be either a carboxyl group, either as such or in an optionally protected form;

Route B. The process comprises the dissolution in a solvent and stirring of an equimolar mixture of amine of formula (II) with glyoxylic acid (IV) and boronic acid (V);

Route C. The process comprises the reaction between compounds of general formula (VI)

(VI)

and (VII)

(VII)

The operative conditions that may be used in the processes of the present invention are described in more details below and are further reported in the following Scheme 1.

The starting materials for the preparation of the compounds of formula (I), that is the compounds of formula (II) and (III), as well as any reactant of the process are known or easily prepared according to known procedures.

Scheme 1

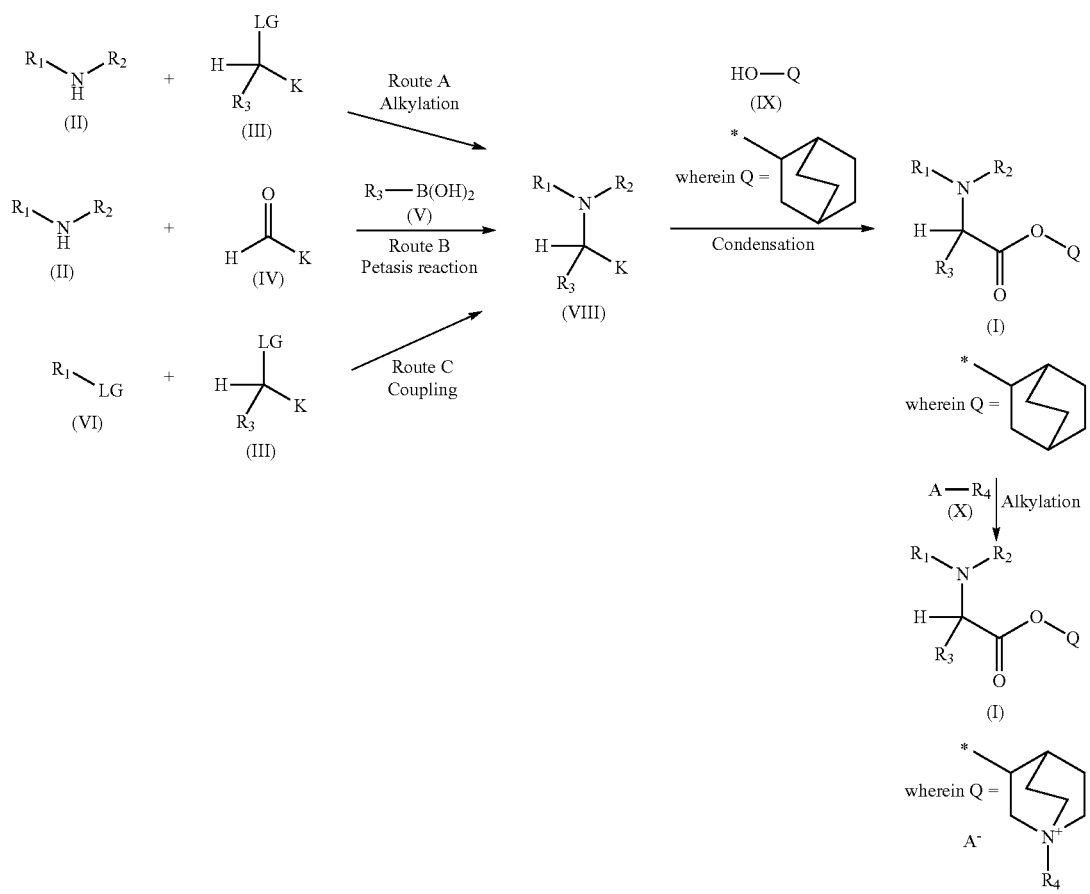

Procedure for the Preparation of Compounds of Formula (I).

According to a particular embodiment of the present invention, the compounds of general formula (I) may be prepared, for example, following synthetic pathways described in scheme 1. Compounds of general formula (VIII) may be for instance prepared according to three different routes: A, B or C.

According to Route A, compounds of general formula (VIII) may be prepared through the alkylation of an amine of formula (II) with a compound of general formula (III), in which LG is a suitable leaving group (e.g. an halide such as bromine) and K is a carboxyl group in an optionally protected form.

Typically, LG is a halide atom and, more preferably, it is a bromine atom. As far as K is concerned, it may be a carboxyl group either as such or in an optionally protected form, typically including carboxyalkyl ester groups (e.g. K=COO($C_1$-$C_6$)alkyl), preferably carboxymethyl (e.g. COOMe).

The alkylation reaction may be promoted by the presence of a base, for instance an amine selected from the group consisting of triethylamine, pyridine and 4-dimethylaminopyridine, either neat or in a suitable solvent (e.g. acetonitrile). This reaction is usually performed in a temperature range from about 0° C. to about 130° C. over a period of about 1 hour up to about 74 hours. The reaction may be conducted under conventional heating (using an oil bath) or under microwave heating. The reaction may be carried out in an open vessel or in a sealed tube.

According to Route B, compounds of general formula (VIII) may be prepared by means of a Petasis-Mannich reaction following one of the different procedures reported in literature (e.g.: Petasis N. A., Akritopoulou I., *Tetrahedron Lett.,* 1993, 34, 583; Follmann, M., *Synlett,* 2005, 6, 1009; Kausik K. N., *Tetrahedron Letters,* 2005, 46, 2025, all of which are incorporated herein by reference in their entireties), through, for instance, the reaction of an equimolar mixture of amine (II), glyoxylic acid (IV) and boronic acid (V) in a suitable solvent (e.g. dichloromethane, acetonitrile) and stirred. This reaction is usually performed in a temperature range from about 0° C. to about 110° C. over a period of about 1 hour up to about 74 hours. The reaction may be conducted under conventional heating (using an oil bath) or under microwave heating. The reaction may be carried out in an open vessel or in a sealed tube.

According to Route C, compounds of general formula (VI) and (VII) may react under the typical conditions of the aromatic nucleophilic substitution to afford compound (VIII).

Compounds of formula (I) wherein Q is

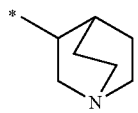

may then be prepared by coupling the alcohol (IX) with compounds of formula (VIII).

The operative conditions are chosen on the basis of the reactivity of the compound (VIII) over alcohol (IX) and of the compatibility of other groups being present in both reactants (for a general reference on the above reaction and operative conditions thereof see, for instance, Carey, F. A. and Sundeberg, R. J. Advanced Organic Chemistry, Third Edition (1990), Plenum Press, New York and London, pg 145, which is incorporated herein by reference in its entirety).

In particular, in the case K is a protected carboxyl group, the protecting group has to be first removed before the coupling reaction takes place. As such, for instance, in case K is a carboxyester moiety (e.g. K=COOMe), removal of the protecting group is carried out under hydrolysis conditions, typically in the presence of any suitable aqueous base selected from the group consisting of sodium, lithium and potassium hydroxide. The reaction is performed in any suitable solvent, for instance in the presence of tetrahydrofuran or dioxane at room temperature (RT) and over a period of about 1 hour up to about 36 hours.

Alternatively, when starting from a compound of formula (VIII) wherein K is carboxyl, standard amidation and peptide coupling conditions may be applied to obtain the compounds of formula (I) wherein Q is as defined above. The said conditions include, for instance, activating intermediate (VIII) by means of one or more equivalents of a commercially available condensing agent such as a carbodiimide (e.g. dicyclohexyl-carbodiimide (DCC) and the like) for example in the presence of N-hydroxybenzotriazole (HOBT) followed by reaction of the activated intermediate with alcohol (IX), results in the formation of compounds (I) wherein Q is as defined above. An organic base such as triethylamine may be also present in the reaction mixture. The activated intermediate may be either isolated, or pre-formed or generated in situ, and then properly reacted with the alcohol of formula (IX). Suitable solvents for the coupling reaction include, but are not limited to, halocarbon solvents (e.g. dichloromethane), tetrahydrofuran, dioxane and acetonitrile. The reaction proceeds at temperature ranging from about 0° C. up to about 170° C., for a time period in the range of about 1 hour up to about 72 hours. The reaction may be carried out under conventional heating (using an oil bath) or under microwave irradiation. The reaction may be conducted either in an open vessel or in a sealed tube.

Once obtained, compounds of general formula (I) wherein Q is as defined above, can be achieved either as single diastereoisomer or as a mixture of diasteroisomers. For instance, in the case alcohol (IX) features the R configuration, corresponding compound (I) can be obtained in both S—R or R—R configuration, as well as a mixture of diasteroisomers (R—R and S—R configuration).

The said mixture of diastereoisomers may be converted to compounds of formula (I) wherein Q is a group of formula (ii), or can be most conveniently resolved to give the two single diasteroisomers, which in turn may be converted to compounds of formula (I), wherein Q is as defined above. This separation can be accomplished by using procedures well known to those skilled in the art. These procedures include, but are not limited to, chromatography purification, preparative HPLC purification and crystallization. For example, the two diastereoisomers can be separated by flash chromatography on silica gel eluting with suitable solvents or mixture of solvents such as DCM, methanol and the like. In another process of the present invention separation of disteroisomers may be carried out by using a column filled with a chiral stationary phase, for example Chiralpack AY or Chiralcel OD or Chiralcel OZ, and eluting, for example, with acetonitrile and/or with mixtures of acetonitrile and an alcohol. Alternatively the separation of diasteroisomers may be most conveniently achieved by crystallization from an opportune solvent (e.g. ethyl ether), as a free base or after the formation of a suitable salt (e.g. (+)-tartaric acid).

The compounds of general formula (I) wherein Q is a group of formula (i), are then alkylated with an agent of general formula (I) to give compounds of general formula (I), wherein Q is a group of formula (ii).

This kind of reaction is largely described in literature under several different conditions. For instance, the reaction may be performed neat or in a suitable solvent selected from the group consisting of acetonitrile, DMF, DMSO, and tetrahydrofuran. The reaction typically proceeds at temperature range from about 0° C. up to about 170° C., for a time in the range of few minutes up to about 72 hours. The reaction may be carried out under conventional heating (using an oil bath) or under microwave irradiation. The reaction may be conducted either in an open vessel or in a sealed tube.

Compounds of general formula (I) wherein Q is a group of formula (ii), can be either considered as final products or can be further reacted to prepare other compounds of general formula (I). Thus, any suitable moiety of $R_1$, $R_2$, $R_3$, $R_4$, and $R_5$ group in general formula (I) could undergo a variety of reactions, to afford other final compounds of general formula (I).

Likewise, the optional salification of the compounds of formula (I) wherein Q is a group of formula (ii), may be carried out by properly converting any of the free acidic groups (e.g. carboxylic) or free amino groups into the corresponding pharmaceutically acceptable salts.

In this case too, the operative conditions being employed for the optional salification of the compounds of the invention are all within the ordinary knowledge of the skilled person.

As formerly reported, the compounds of formula (III) are known and, if not commercially available, may be readily prepared according to known methods, extensively reported in the literature.

For instance compounds of general formula (III) in which LG is a halogen such as a bromine, may be prepared by halogenation of the opportunely substituted phenyl acetic ester (for example following the procedure reported by Epstein, J. W. in *J. Med. Chem.*, 1981, 24/5, 481, which is incorporated herein by reference in its entirety. Alternatively, compounds of general formula (III) may be prepared starting from the appropriately substituted mandelic derivative, using procedures readily apparent to those skilled in the art (a survey of the suitable reactions is given by Larock, L. C., *Comprehensive Organic Transformation*, Second edition (1999), John Wiley & Son Inc, pg 689-700, which incorporated herein by reference in its entirety).

From all of the above, it should be clear to the skilled person that the above process, comprehensive of any variant thereof for the preparation of suitable compounds of formula (I) of the invention, may be conveniently modified so as to adapt the reaction conditions to the specific needs, for instance by choosing appropriate condensing agents, solvents and protective groups, as the case may be.

More in particular, functional groups being present in any of the compounds of formula (III), (IV), (VI) or (VIII) and which could give rise to unwanted side reactions and by-products, need to be properly protected before the condensation reaction takes place. Likewise, subsequent deprotection of those same protected groups may follow upon completion of the said reactions.

In the present invention, unless otherwise indicated, the term "protecting group", designates a protective group adapted to preserving the function of the group to which it is bound. Specifically, protective groups are used to preserve amino, hydroxyl or carboxyl functions.

Appropriate protective groups may thus include, for example, benzyl, benzyloxycarbonyl, alkyl or benzyl esters, or other substituents commonly used for the protection of such functions, which are all well known to those skilled in the art [see, for a general reference, T. W. Green; *Protective Groups in Organic Synthesis* (Wiley, N.Y. 1981), which is incorporated herein by reference in its entirety].

The present invention also provides pharmaceutical compositions of compounds of general formula (I) in admixture with one or more pharmaceutically acceptable carriers, for example those described in *Remington's Pharmaceutical Sciences Handbook*, XVII Ed., Mack Pub., N.Y., U.S.A., which is incorporated herein by reference in its entirety.

In the present invention, the terms active ingredient or active or compound are to be considered synonyms to be used interchangeably.

Administration of the compounds of the present invention may be accomplished according to patient needs, for example, orally, nasally, parenterally (subcutaneously, intravenously, intramuscularly, intrasternally and by infusion), by inhalation, rectally, vaginally, topically, locally, transdermally, and by ocular administration.

Various solid oral dosage forms can be used for administering compounds of the invention including such solid forms as tablets, gelcaps, capsules, caplets, granules, lozenges and bulk powders. The compounds of the present invention can be administered alone or combined with various pharmaceutically acceptable carriers, diluents (such as sucrose, mannitol, lactose, starches) and excipients known in the art, including but not limited to suspending agents, solubilizers, buffering agents, binders, disintegrants, preservatives, colorants, flavorants, lubricants and the like. Time release capsules, tablets and gels are also advantageous in administering the compounds of the present invention.

Various liquid oral dosage forms can also be used for administering compounds of the present invention, including aqueous and non-aqueous solutions, emulsions, suspensions, syrups, and elixirs. Such dosage forms can also contain suitable inert diluents known in the art such as water and suitable excipients known in the art such as preservatives, wetting agents, sweeteners, flavorants, as well as agents for emulsifying and/or suspending the compounds of the invention. The compounds of the present invention may be injected, for example, intravenously, in the form of an isotonic sterile solution. Other compositions are also possible.

Suppositories for rectal administration of the compounds of the present invention can be prepared by mixing the compound with a suitable excipient such as cocoa butter, salicylates, and polyethylene glycols.

Formulations for vaginal administration can be in the form of cream, gel, paste, foam, or spray formula containing, in addition to the active ingredient, such suitable carriers as are known in the art.

For topical administration the pharmaceutical composition can be in the form of creams, ointments, liniments, lotions, emulsions, suspensions, gels, solutions, pastes, powders, sprays, and drops suitable for administration to the skin, eye, ear or nose. Topical administration may also involve transdermal administration via means such as transdermal patches.

For the treatment of the diseases of the respiratory tract, the compounds according to the invention are preferably administered by inhalation. Inhalable compositions include inhalable powders, propellant-containing metering aerosols or propellant-free inhalable formulations.

For administration as a dry powder, single- or multi-dose inhalers known from the prior art may be utilized. In that case the powder may be filled in gelatine, plastic or other capsules, cartridges or blister packs or in a reservoir.

A diluent or carrier, generally non-toxic and chemically inert to the compounds of the present invention, e.g. lactose or any other additive suitable for improving the respirable fraction may be added to the powdered compounds of the invention.

Inhalation aerosols containing propellant gas such as hydrofluoroalkanes may contain the compounds of the invention either in solution or in dispersed form. The propellant-driven formulations may also contain other ingredients such as co-solvents, stabilizers and optionally other excipients.

The propellant-free inhalable formulations comprising the compounds of the invention may be in form of solutions or suspensions in an aqueous, alcoholic or hydroalcoholic medium, and they may be delivered by jet or ultrasonic nebulizers or by soft-mist nebulizers.

The compounds of the present invention may be administered as the sole active agent or in combination with other pharmaceutical active ingredients including those currently used in the treatment of respiratory disorders, e.g. beta2-agonists, corticosteroids, P38 MAP kinase inhibitors, IKK2, HNE inhibitors, PDE4 inhibitor, leukotriene modulators, NSAIDs, and mucus regulators.

The present invention also provides combinations of a compound of general formula (I) with a β2-agonist selected from the group consisting of GSK-642444, indacaterol, milveterol, arformoterol, salbutamol, levalbuterol, terbutaline, AZD-3199, BI-1744-CL, LAS-100977, bambuterol, isoproterenol, procaterol, clenbuterol, reproterol, fenoterol, and ASF-1020.

The present invention also provides combinations of a compound of general formula (I) with a corticosteroid selected from the group consisting of propionate, ciclesonide, mometasone furoate, and budesonide.

The present invention also provides combinations of a compound of general formula (I) with a P38 inhibitor selected from the group consisting of semapimod, talmapimod, pirfenidone, PH-797804, GSK-725, minokine, and losmapimod.

The present invention also provides combinations of a compound of general formula (I) with a IKK2 inhibitor.

The present invention also provides combinations of a compound of general formula (I) with a HNE inhibitor selected from the group consisting of AAT, ADC-7828, Aeriva, TAPI, AE-3763, KRP-109, AX-9657, POL-6014, AER-002, AGTC-0106, respriva, AZD-9668, zemaira, AAT IV, PGX-100, elafin, SPHD-400, prolastin C, and prolastin inhaled.

The present invention also provides combinations of a compound of general formula (I) with a PDE4 inhibitor selected from the group consisting of AN-2728, AN-2898, CBS-3595, apremilast, ELB-353, KF-66490, K-34, LAS-37779, IBFB-211913, AWD-12-281, cipamfylline, cilomilast, roflumilast, BAY19-8004 and SCH-351591, AN-6415, indus-82010, TPI-PD3, ELB-353, CC-11050, GSK-256066, oglemilast, OX-914, tetomilast, MEM-1414, and RPL-554.

The present invention also provides combinations of a compound of general formula (I) with a leukotriene modulator selected from the group consisting of montelukast, zafirlukast, and pranlukast.

The present invention also provides combinations of a compound of general formula (I) with a NSAID selected from the group consisting of ibuprofen and ketoprofen.

The present invention also provides combinations of a compound of general formula (I) with a mucus regulator selected from the group consisting of INS-37217, diquafosol, sibenadet, CS-003, talnetant, DNK-333, MSI-1956, and gefitinib.

The dosages of the compounds of the present invention depend upon a variety of factors including the particular disease to be treated, the severity of the symptoms, the route of administration, the frequency of the dosage interval, the particular compound utilized, the efficacy, toxicology profile, and pharmacokinetic profile of the compound. Advantageously, the compounds of formula (I) can be administered for example, at a dosage of 0.001 to 1000 mg/day, preferably 0.1 to 500 mg/day.

When the compounds of formula (I) are administered by inhalation route, they are preferably given at a dosage of 0.001 to 500 mg/day, preferably 0.1 to 200 mg/day.

The compounds of formula (I) may be administered for the prevention and/or treatment of any disease wherein M3 antagonists are active. Said disease include: diseases involving inflammation such as asthma and COPD, acute rhinitis; diseases involving the gastrointestinal tract such as peptic ulcer; diseases involving the cardiovascular system such as acute myocardial infarction; diseases involving the genitourinary tract such as renal colic; anticholinesterase and mushroom poisoning; uses in anesthesia; uses in ophthalmology.

They also include neurological and psychiatric disorders such as Parkinsonism (Parkinson's disease) and motion sickness.

Preferably the compounds of formula (I) may be administered for the prevention and/or treatment of respiratory diseases such as from mild to acute severe conditions of asthma and COPD.

Other respiratory diseases include bronchitis, bronchiolitis, bronchiectasis, acute nasoparyngitis, acute and chronic sinusitis, maxillary sinusitis, pharyngitis, tonsillitis, laryngitis, tracheitis, epiglottis, croup, chronic disease of tonsils and adenoids, hypertrophy of tonsils and adenoids, peritonsillar abscess, rhinitis, abscess or ulcer and nose, pneumonia, viral and bacterial pneumonia, bronchopneumonia, influenza, extrinsic allergic alveolitis, coal workers' pneumoconiosis, asbestosis, pneumoconiosis, pneumonopathy, respiratory conditions due to chemical fumes, vapors and other external agents, emphysema, pleurisy, pneumothorax, abscess of lung and mediastinum, pulmonary congestion and hypostasis, postinflammatory pulmonary fibrosis, other alveolar and parietoalveolar pneumonopathy, idiopathic fibrosing alveolitis, Hamman-Rich syndrome, atelectasis, ARDS, acute respiratory failure, mediastinitis.

Other features of the invention will become apparent in the course of the following descriptions of exemplary embodiments which are given for illustration of the invention and are not intended to be limiting thereof.

EXAMPLES

In the following examples:
I=intermediates
C=compounds

Example 1

Preparation of (3R)-3-(2-(6-methoxypyridin-3-yl)-2-(phenylamino)acetoxy)-1-(2-oxo-2-phenylethyl)-1-azoniabicyclo[2.2.2]octane trifluoroacetate (C3)

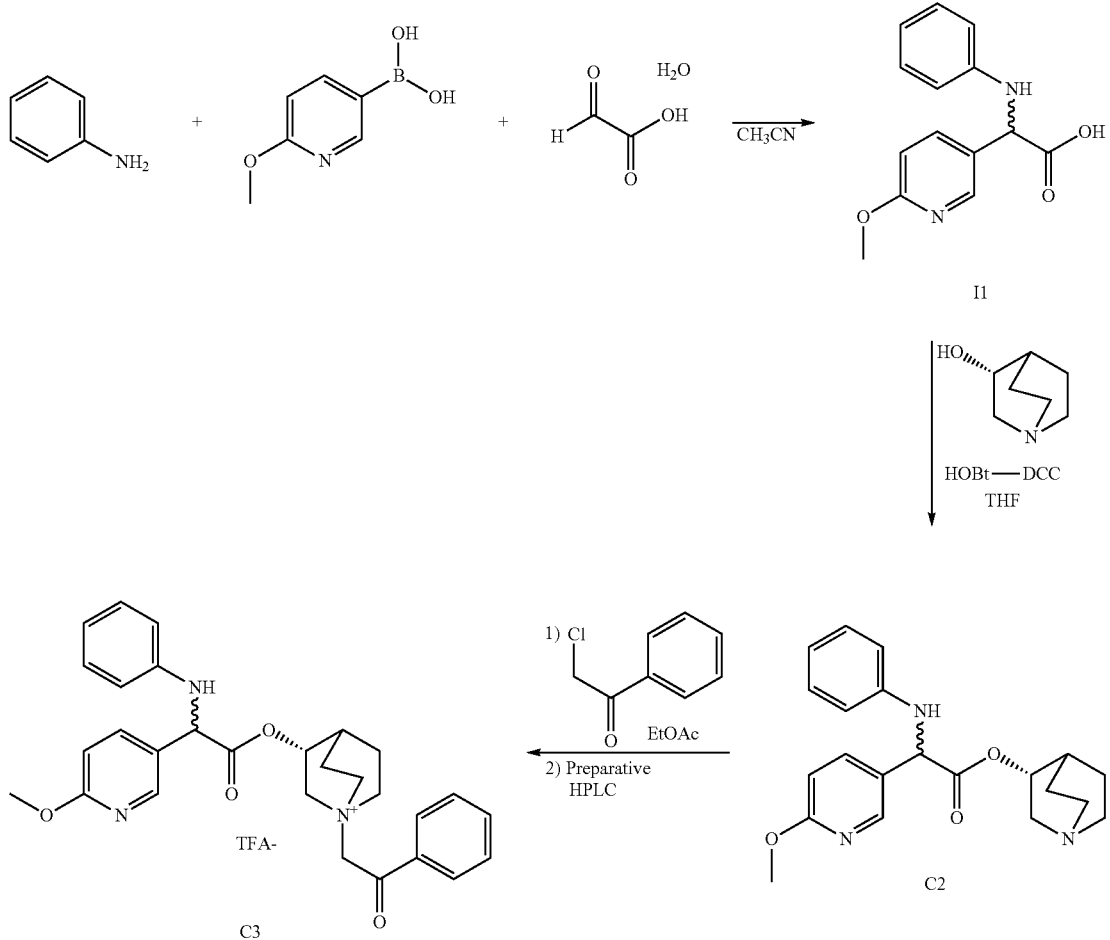

Scheme 2

Preparation of 2-(6-methoxypyridin-3-yl)-2-(phenylamino)acetic acid (I1)

A mixture of aniline (0.30 ml, 3.27 mmol), 6-methoxypyridin-3-ylboronic acid (500 mg, 3.27 mmol) and 2-oxoacetic acid hydrate (301 mg, 3.27 mmol) in acetonitrile (20 ml) was heated under microwave irradiation at 100° C. for 1 hour. The reaction mixture was evaporated to dryness, and the crude product was triturated with acetonitrile. The solid was collected by suction filtration to get 2-(6-methoxypyridin-3-yl)-2-(phenylamino)acetic acid (202 mg, 23% yield).

Preparation of (R)-quinuclidin-3-yl 2-(6-methoxypyridin-3-yl)-2-(phenylamino)acetate (C2)

A mixture of 2-(6-methoxypyridin-3-yl)-2-(phenylamino) acetic acid (I1) (100 mg, 0.39 mmol), (R)-quinuclidin-3-ol (59.1 mg, 0.46 mmol), HOBT (71.2 mg, 0.46 mmol) and DCC (96 mg, 0.46 mmol) was dissolved in dry THF (10 ml). The resulting reaction was stirred at room temperature overnight. Then solvent was removed under reduced pressure, and the residue was taken up with EtOAc and washed twice with 2M $K_2CO_3$. The organic phase was dried over $Na_2SO_4$, filtered and evaporated to dryness. The crude was purified by flash chromatography (DCM/MeOH=98/2) to obtain (R)-quinuclidin-3-yl 2-(6-methoxypyridin-3-yl)-2-(phenylamino)acetate (33 mg, 23% yield).

Preparation of (3R)-3-(2-(6-methoxypyridin-3-yl)-2-(phenylamino)acetoxy)-1-(2-oxo-2-phenylethyl)-1-azoniabicyclo[2.2.2]octane trifluoroacetate (C3)

2-Chloro-1-phenylethanone (13.9 mg, 0.09 mmol) was added to a solution of (R)—((R)-quinuclidin-3-yl) 2-phenyl-2-(phenylamino)acetate (C2) (60 mg, 0.18 mmol) in EtOAc (3 ml). The reaction mixture was stirred at room temperature overnight. EtOAc was evaporated, and the residue was triturated with $Et_2O$. The solid was collected by filtration and then purified by preparative HPLC to obtain (3R)-3-(2-(6-methoxypyridin-3-yl)-2-(phenylamino)acetoxy)-1-(2-oxo-2-phenylethyl)-1-azoniabicyclo[2.2.2]octane trifluoroacetate (26.4 mg, 49% yield).

$^1$H NMR (300 MHz, DMSO-$d_6$) δ ppm 8.33-8.39 (m, 1H), 7.92-8.04 (m, 2H), 7.88 (dd, 1H), 7.70-7.82 (m, 1H), 7.54-7.68 (m, 2H), 7.05-7.20 (m, 2H), 6.87 and 6.88 (d, 1H), 6.69-6.78 (m, 2H), 6.55-6.69 (m, 1H), 5.39 and 5.42 (s, 1H), 5.20-5.28 (m, 1H), 5.10 and 5.17 (s, 2H), 3.85 and 3.86 (s, 3H), 3.73-3.80 (m, 1H), 3.36-3.61 (m, 5H), 2.12-22 and 2.33-2.44 (m, 1H), 1.84-2.12 (m, 4H);

LC-MS (ESI POS): 486.19 (M+);

Example 2

Preparation of (3R)-3-(2-(2-acetylthiophen-3-ylamino)-2-phenylacetoxy)-1-(2-oxo-2-phenylethyl)-1-azoniabicyclo[2.2.2]octane trifluoroacetate (C6)

Scheme 3

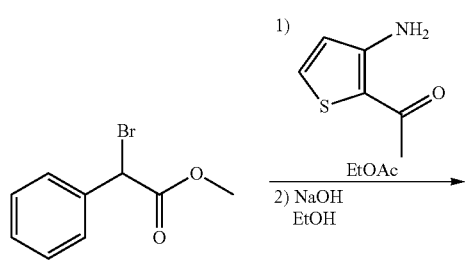

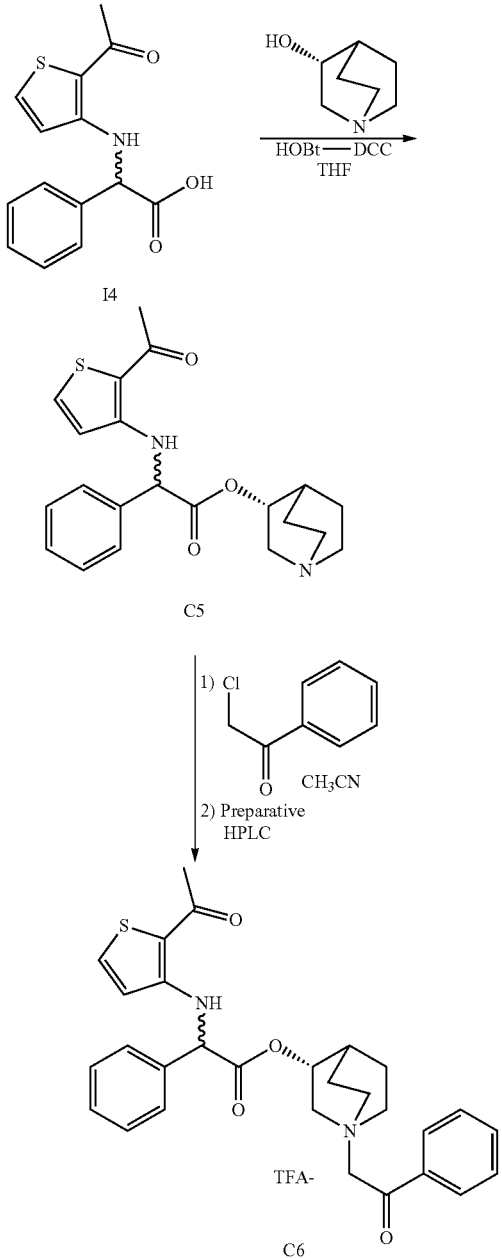

Preparation of 2-(2-acetylthiophen-3-ylamino)-2-phenylacetic acid (I4)

A solution of ethyl 2-bromo-2-phenylacetate (349 μl, 2.00 mmol) and 1-(3-aminothiophen-2-yl)ethanone (282 mg, 2.00 mmol) in acetonitrile (2 ml) was heated under microwave irradiation at 100° C. for 1 hour. Acetonitrile was evaporated, and the residue was dissolved in EtOH (2 ml), and sodium hydroxide (80.0 mg, 2.00 mmol) was added. The reaction mixture was stirred at room temperature for 24 hours, and then ethanol was evaporated under vacuum. The residue was taken up with water and washed with EtOAc. The pH of the aqueous phase was adjusted to 3 with HCl, and the aqueous phase was back-extracted with EtOAc. The organic phase was dried over $Na_2SO_4$, filtered and evaporated to dryness to obtain 2-(2-acetylthiophen-3-ylamino)-2-phenylacetic acid (188 mg, 34% yield), which was used in the next step without any further purification.

Preparation of (2-acetyl-thiophen-3-ylamino)-phenyl-acetic acid (R)-(1-aza-bicyclo[2.2.2]oct-3-yl) ester (C5)

A mixture of 2-(2-acetylthiophen-3-ylamino)-2-phenylacetic acid (I4) (188 mg, 0.68 mmol), (R)-quinuclidin-3-ol (104 mg, 0.82 mmol), HOBT (125 mg, 0.82 mmol) and DCC (169 mg, 0.82 mmol) in dry THF (8 ml) was stirred at room temperature overnight. THF was evaporated, and the crude product was taken up with EtOAc and washed twice with 2M $K_2CO_3$. The organic phase was dried ($Na_2SO_4$), filtered and evaporated to dryness. The crude product was purified by preparative HPLC. The fractions containing the product were combined and evaporated under vacuum. The residue was dissolved in 2M $K_2CO_3$ and extracted twice with EtOAc to obtain (2-acetyl-thiophen-3-ylamino)-phenyl-acetic acid (R)-(1-aza-bicyclo[2.2.2]oct-3-yl)ester (48 mg, 18% yield).

Preparation of (3R)-3-(2-(2-acetylthiophen-3-ylamino)-2-phenylacetoxy)-1-(2-oxo-2-phenylethyl)-1-azoniabicyclo[2.2.2]octane trifluoroacetate (C6)

2-Chloro-1-phenylethanone (19.3 mg, 0.12 mmol) was added to a solution of methyl (2-acetyl-thiophen-3-ylamino)-phenyl-acetic acid (R)-(1-aza-bicyclo[2.2.2]oct-3-yl)ester (C5) (35.7 mg, 0.09 mmol) in EtOAc (2 ml). The reaction mixture was stirred at room temperature overnight. Solvent was removed under reduced pressure. The crude product was purified by preparative HPLC to obtain (3R)-3-(2-(2-acetylthiophen-3-ylamino)-2-phenylacetoxy)-1-(2-oxo-2-phenylethyl)-1-azoniabicyclo[2.2.2]octane trifluoroacetate (42.1 mg, 55% yield).

$^1$H NMR (300 MHz, DMSO-$d_6$) δ ppm 9.01 and 9.04 (d, 1H), 7.91-8.07 (m, 2H), 7.72-7.81 (m, 1H), 7.70 and 7.71 (d, 1H), 7.56-7.67 (m, 2H), 7.28-7.54 (m, 5H), 6.74 and 6.75 (d, 1H), 5.68 and 5.74 (d, 1H), 5.21-5.35 (m, 1H), 5.12 and 5.17 (s, 2H), 3.94-4.25 (m, 1H), 3.29-3.88 (m, 5H), 2.34 (s, 3H), 2.15-2.25 and 2.38-2.46 (m, 1H), 1.43-2.15 (m, 4H);

LC-MS (ESI POS): 503.14 (M+).

Example 3

Preparation of (3R)-3-(2-(2-carbamoylthiophen-3-ylamino)-2-phenylacetoxy)-1-(2-oxo-2-phenylethyl)-1-azoniabicyclo[2.2.2]octane 2,2,2-trifluoroacetate (C9)

Scheme 4

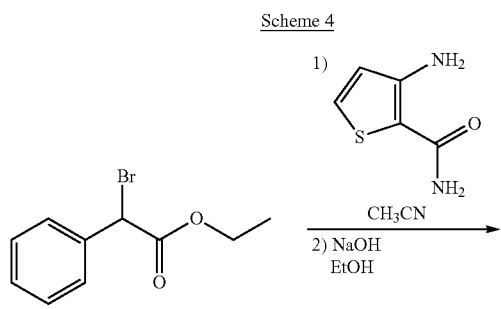

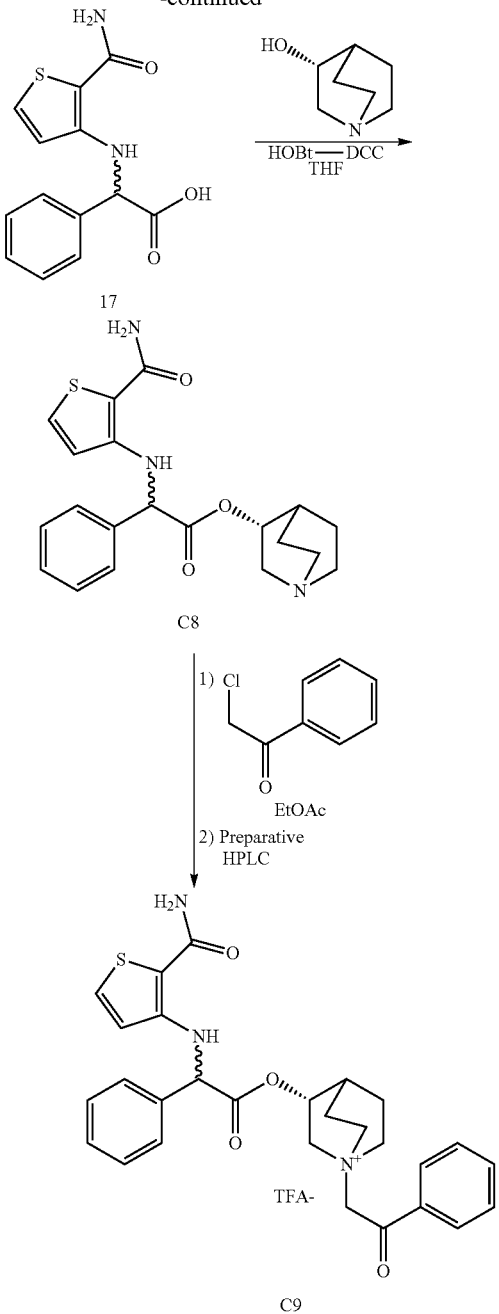

Preparation of 2-(2-carbamoylthiophen-3-ylamino)-2-phenylacetic acid (I7)

A solution of ethyl 2-bromo-2-phenylacetate (349 µl, 2.00 mmol) and 3-aminothiophene-2-carboxamide (284 mg, 2.00 mmol) in acetonitrile (2 ml) was heated under microwave irradiation at 100° C. for 1 hour. Acetonitrile was evaporated, and the residue was dissolved in EtOH (2 ml). Sodium hydroxide (80 mg, 2.00 mmol) was added, and the reaction mixture was stirred at room temperature for 24 hours. Then ethanol was evaporated, and the residue was taken up with water and washed with EtOAc. The pH of the aqueous phase was adjusted to 3 with HCl, and product was extracted with EtOAc. The organic phase was dried over $Na_2SO_4$, filtered and evaporated to dryness to obtain 2-(2-carbamoylthiophen- 3-ylamino)-2-phenylacetic acid (389 mg, 70% yield), which was used in the next step without any further purification.

Preparation of (R)-quinuclidin-3-yl 2-(2-carbamoylthiophen-3-ylamino)-2-phenylacetate (C8)

A mixture of 2-(2-carbamoylthiophen-3-ylamino)-2-phenylacetic acid (I7) (389 mg, 1.41 mmol), (R)-quinuclidin-3-ol (215 mg, 1.69 mmol), DCC (349 mg, 1.69 mmol) and HOBT (259 mg, 1.69 mmol) in dry THF (5 ml) was stirred at room temperature overnight. THF was evaporated, and the crude product was taken up with EtOAc and washed twice with 2M $K_2CO_3$. The organic phase was dried over $Na_2SO_4$, filtered and evaporated to dryness. The crude product was purified by preparative HPLC. The fractions with the product are combined and evaporated to dryness. The residue was dissolved in 2M $K_2CO_3$ and extracted twice with EtOAc to obtain (R)-quinuclidin-3-yl 2-(2-carbamoylthiophen-3-ylamino)-2-phenylacetate (32 mg, 6% yield).

Preparation of (3R)-3-(2-(2-carbamoylthiophen-3-ylamino)-2-phenylacetoxy)-1-(2-oxo-2-phenylethyl)-1-azoniabicyclo[2.2.2]octane 2,2,2-trifluoroacetate (C9)

2-Chloro-1-phenylethanone (12.8 mg, 0.08 mmol) was added to a solution of (R)-quinuclidin-3-yl 2-(2-carbamoylthiophen-3-ylamino)-2-phenylacetate (C8) (32 mg, 0.08 mmol) in EtOAc (2 ml). The reaction mixture was stirred at room temperature overnight, and then the solvent was removed under reduced pressure and the crude product was purified by preparative HPLC to obtain (3R)-3-(2-(2-carbamoylthiophen-3-ylamino)-2-phenylacetoxy)-1-(2-oxo-2-phenylethyl)-1-azoniabicyclo[2.2.2]octane 2,2,2-trifluoroacetate (24.3 mg, 47% yield).

$^1$H NMR (300 MHz, DMSO-$d_6$) δ ppm 8.44-8.62 (m, 1H) 7.89-8.03 (m, 2H) 7.69-7.82 (m, 1H) 7.54-7.67 (m, 2H) 7.29-7.54 (m, 5H) 6.96-7.11 (m, 1H) 6.65-6.79 (m, 1H) 5.49-5.70 (m, 1H) 5.03-5.37 (m, 3H) 4.00-4.23 (m, 1H) 3.66-3.83 (m, 5H) 2.39 (m, 1H) 1.50-2.16 (m, 4H);

LC-MS (ESI POS): 504.13 (M+).

Example 4

Preparation of (3R)-3-(2-(2-(methoxycarbonyl)thiophen-3-ylamino)-2-phenylacetoxy)-1-(2-oxo-2-(thiazol-2-yl)ethyl)-1-azoniabicyclo[2.2.2]octane trifluoroacetate (Diastereomer 1 of C12)

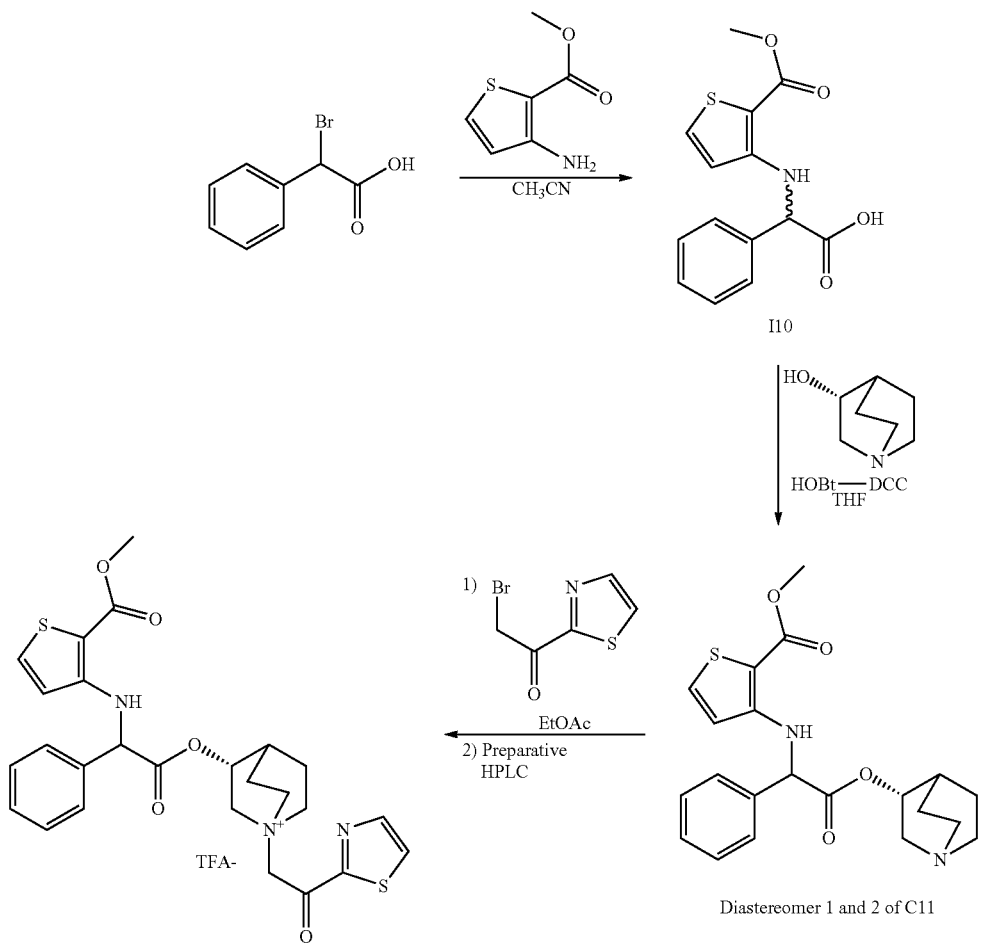

Scheme 5

Diastereomer 1 and 2 of C11

Diastereomer 1 and C12

Preparation of 2-(2-(methoxycarbonyl)thiophen-3-ylamino)-2-phenylacetic acid (I10)

A solution of ethyl 2-bromo-2-phenylacetic acid (600 mg, 2.79 mmol) and methyl 3-aminothiophene-2-carboxylate (438 mg, 2.79 mmol) in acetonitrile (20 ml) was heated under microwave irradiation at 100° C. for 1 hour. Acetonitrile was evaporated to dryness and the resulting residue was used in the next step without any further purification.

Preparation of methyl 3-(2-oxo-1-phenyl-2-((R)-quinuclidin-3-yloxy)ethylamino)thiophene-2-carboxylate (Diastereomer 1 and 2 of C11)

A mixture of 2-(2-(methoxycarbonyl)thiophen-3-ylamino)-2-phenylacetic acid (I10) (404 mg, 1.39 mmol), (R)-quinuclidin-3-ol (529 mg, 4.17 mmol), DCC (859 mg, 4.17 mmol) and HOBT (567 mg, 4.17 mmol) in dry THF (25 ml) was stirred at room temperature overnight. THF was evaporated, and the crude product was taken up with EtOAc and washed twice with 2M $K_2CO_3$. The organic phase was dried over $Na_2SO_4$, filtered and evaporated to dryness. The crude was purified by flash chromatography (DCM/MeOH=98/2 to 95/5) recovering diastereomer 1 of C11 (161 mg; 28% yield), and subsequently diastereomer 2 of C11 (127 g, 35% yield).

Diastereomer 1 of C11:
$^1$H NMR (300 MHz, DMSO-d6) ppm: 7.76 (d, 1H), 7.64 (d, 1H), 7.22-7.54 (m, 5H), 6.71 (d, 1H), 5.60 (d, 1H), 4.58-4.89 (m, 1H), 3.78 (s, 3H), 2.98 (ddd, 1H), 2.54-2.69 (m, 3H), 2.13-2.27 (m, 1H), 1.96-2.09 (m, 1H), 1.85-1.96 (m, 1H), 1.51-1.73 (m, 2H), 1.21-1.51 (m, 2H)
LC-MS (ESI POS): 401.1 (M+)

Diastereomer 2 of C11:
$^1$H NMR (300 MHz, DMSO-d6) ppm: 7.78 (d, 1H) 7.66 (d, 1H) 7.17-7.53 (m, 5H) 6.68 (d, 1H) 5.63 (d, 1H) 4.72-5.09 (m, 1H) 3.78 (s, 3H) 2.71-3.04 (m, 5H) 1.10-2.07 (m, 6H)
LC-MS (ESI POS): 401.1 (M+).

Preparation of (3R)-3-(2-(2-(methoxycarbonyl)thiophen-3-ylamino)-2-phenylacetoxy)-1-(2-oxo-2-(thiazol-2-yl)ethyl)-1-azoniabicyclo[2.2.2]octane trifluoroacetate (Diastereomer 1 of C12)

2-Bromo-1-(thiazol-2-yl)ethanone (18.4 mg, 0.09 mmol) was added to a solution of methyl 3-(2-oxo-1-phenyl-2-((R)-quinuclidin-3-yloxy)ethylamino)thiophene-2-carboxylate (diastereomer 1 of C11) (35.7 mg, 0.09 mmol) in EtOAc (2 ml). The reaction was stirred at room temperature overnight, and then the solvent was removed under reduced pressure. The crude was purified by preparative HPLC to obtain (3R)-3-(2-(2-(methoxycarbonyl)thiophen-3-ylamino)-2-phenylacetoxy)-1-(2-oxo-2-(thiazol-2-yl)ethyl)-1-azoniabicyclo[2.2.2]octane trifluoroacetate (16 mg, 28% yield).
$^1$H NMR (300 MHz, DMSO-$d_6$) ppm 8.38 (d, 1H) 8.23 (d, 1H) 7.76 (d, 1H) 7.66 (d, 1H) 7.28-7.58 (m, 5H) 6.73 (d, 1H) 5.66-5.75 (m, 1H) 5.25 (s, 1H) 5.14 (s, 2H) 4.00-4.19 (m, 1H) 3.78 (s, 3H) 3.63-3.75 (m, 3H) 3.41 (m, 2H) 2.33-2.46 (m, 1H) 1.85-2.13 (m, 4H);
LC-MS (ESI POS): 526.13 (M+).

Example 5

Preparation of (3R)-1-(2-(4-hydroxyphenyl)-2-oxoethyl)-3-(2-(2-(methoxycarbonyl)thiophen-3-ylamino)-2-phenylacetoxy)-1-azoniabicyclo[2.2.2]octane bromide (C13)

Scheme 6

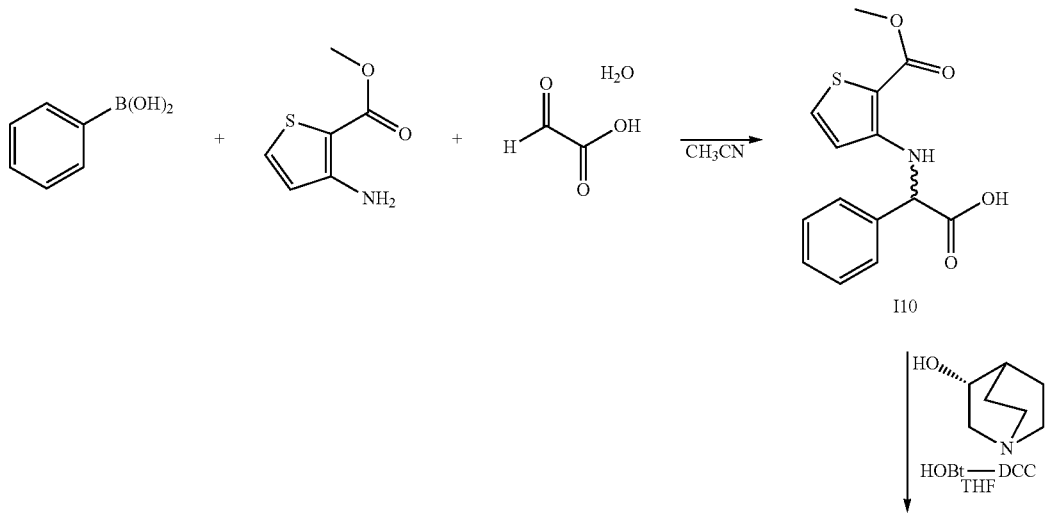

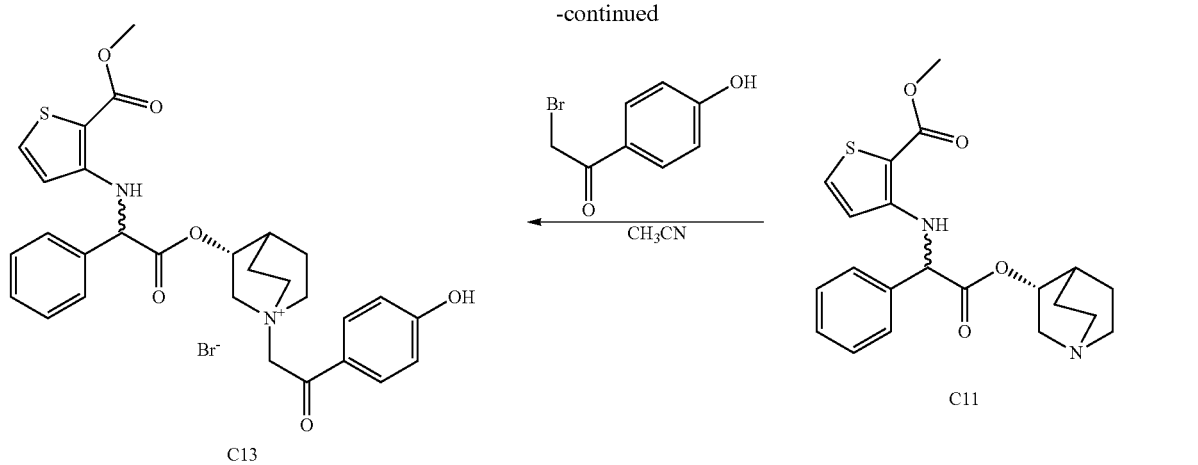

Alternative preparation of 2-(2-(methoxycarbonyl)thiophen-3-ylamino)-2-phenylacetic acid (I10)

A mixture of phenylboronic acid (286 mg, 2.35 mmol), methyl 3-aminothiophene-2-carboxylate (369 mg, 2.35 mmol), and 2-oxoacetic acid hydrate (216 mg, 2.35 mmol) in acetonitrile (20 ml) was stirred at room temperature for 2 hours. The reaction was filtered, and the precipitated was washed with little acetonitrile. The solution was concentrated under reduced pressure, and the precipitate was collected again by filtration, washing with little acetonitrile. The combined precipitates were dried under vacuum overnight to obtain 2-(2-(methoxycarbonyl)thiophen-3-ylamino)-2-phenylacetic acid (558 mg, 82% yield).

Alternative preparation of methyl 3-(2-oxo-1-phenyl-2-((R)-quinuclidin-3-yloxy)ethylamino)thiophene-2-carboxylate (C11)

A mixture of 2-(2-(methoxycarbonyl)thiophen-3-ylamino)-2-phenylacetic acid (I10) (700 mg, 2.40 mmol), 1H-benzo[d][1,2,3]triazol-1-ol (487 mg, 3.60 mmol), (R)-quinuclidin-3-ol (458 mg, 3.60 mmol), and DCC (744 mg, 3.60 mmol) in dry THF (20 ml) was stirred at room temperature overnight. THF was evaporated, the crude product was partitioned between DCM and 2M $K_2CO_3$. The organic phase was collected, dried over $Na_2SO_4$, filtered and evaporated to dryness. The crude was purified by flash-chromatography (DCM/MeOH=95/5) to obtain methyl 3-(2-oxo-1-phenyl-2-((R)-quinuclidin-3-yloxy)ethylamino)thiophene-2-carboxylate (302 mg, 31.4% yield).

Preparation of (3R)-1-(2-(4-hydroxyphenyl)-2-oxoethyl)-3-(2-(2-(methoxycarbonyl)thiophen-3-ylamino)-2-phenylacetoxy)-1-azoniabicyclo[2.2.2]octane bromide (C13)

2-Bromo-1-(4-hydroxyphenyl)ethanone (19.9 mg, 0.09 mmol) was added to a solution of methyl 3-(2-oxo-1-phenyl-2-((R)-quinuclidin-3-yloxy)ethylamino)thiophene-2-carboxylate (C11) (37 mg, 0.09 mmol) in acetonitrile (2 ml). The reaction mixture was stirred at room temperature overnight, and then $Et_2O$ (1 ml) was added and the product was collected by suction filtration to obtain (3R)-1-(2-(4-hydroxyphenyl)-2-oxoethyl)-3-(2-(2-(methoxycarbonyl)thiophen-3-ylamino)-2-phenylacetoxy)-1-azoniabicyclo[2.2.2]octane bromide (36.7 mg, 64.5% yield).

$^1$H NMR (300 MHz, DMSO-$d_6$) ppm 7.80-7.92 (m, 2H), 7.72-7.80 (m, 1H), 7.62-7.69 (m, 1H), 7.29-7.57 (m, 5H), 6.83-6.99 (m, 2H), 6.72 and 6.74 (d, 1H), 5.66 and 5.72 (d, 1H), 5.17-5.31 (m, 1H), 4.99 and 5.05 (s, 2H), 3.97-4.21 (m, 1H), 3.78 (s, 3H), 3.36-3.74 (m, 5H), 2.15-2.25 and 2.34-2.46 (m, 1H), 1.38-2.12 (m, 4H);

LC-MS (ESI POS): 535.39 (M+).

Example 6

Preparation of (3R)-3-(2-(2-(methoxycarbonyl)thiophen-3-ylamino)-2-phenylacetoxy)-1-(2-oxo-2-(thiophen-3-yl)ethyl)-1-azoniabicyclo[2.2.2]octane bromide (C14)

Scheme 7

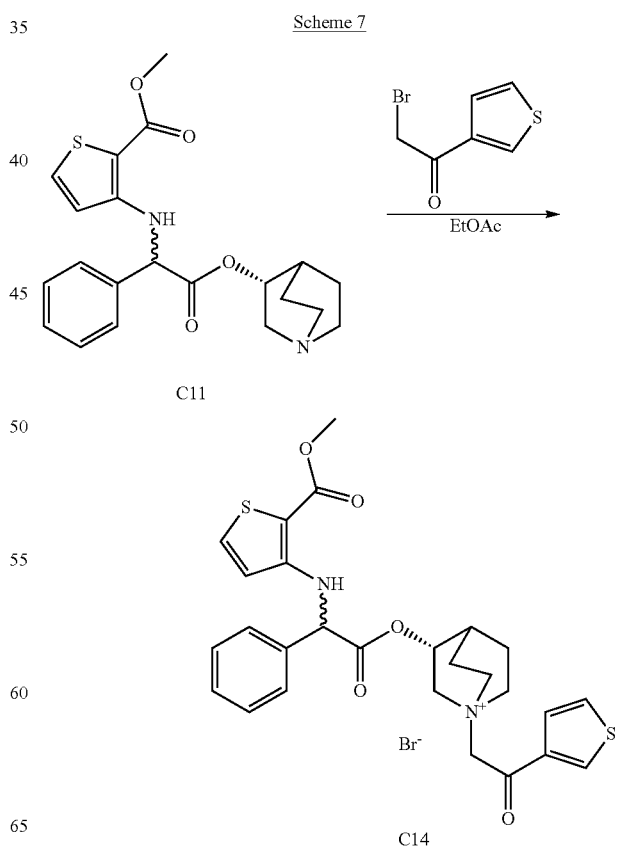

2-Bromo-1-(thiophen-3-yl)ethanone (25.6 mg, 0.12 mmol) was added to a solution of methyl 3-(2-oxo-1-phenyl-2-((R)-quinuclidin-3-yloxy)ethylamino)thiophene-2-carboxylate (C11) (50 mg, 0.12 mmol) in EtOAc (2 ml). The reaction mixture was stirred at room temperature overnight, and then the solvent was evaporated under vacuum. The residue was triturated with $Et_2O$ and then purified by preparative HPLC (Eluent: $CH_3CN/H_2O$) to obtain (3R)-3-(2-(2-(methoxycarbonyl)thiophen-3-ylamino)-2-phenylacetoxy)-1-(2-oxo-2-(thiophen-3-yl)ethyl)-1-azoniabicyclo[2.2.2]octane bromide (44.3 mg, 58.6% yield).

$^1$H NMR (300 MHz, DMSO-$d_6$) δ ppm 8.42-8.70 (m, 1H), 7.27-7.87 (m, 9H), 6.71 and 6.73 (d, 1H), 5.66 and 5.72 (d, 1H), 5.25 (br. s., 1H), 4.98 and 5.03 (s, 2H), 4.00-4.21 (m, 1H), 3.78 (s, 3H), 3.46-3.73 (m, 5H), 2.14-2.24 and 2.34-2.45 (m, 1H), 1.67-2.14 (m, 4H);

LC-MS (ESI POS): 525.33 (M+).

Example 7

Preparation of (3R)-3-(2-(2-(methoxycarbonyl)thiophen-3-ylamino)-2-phenylacetoxy)-1-(3-phenoxypropyl)-1-azoniabicyclo[2.2.2]octane bromide (C15)

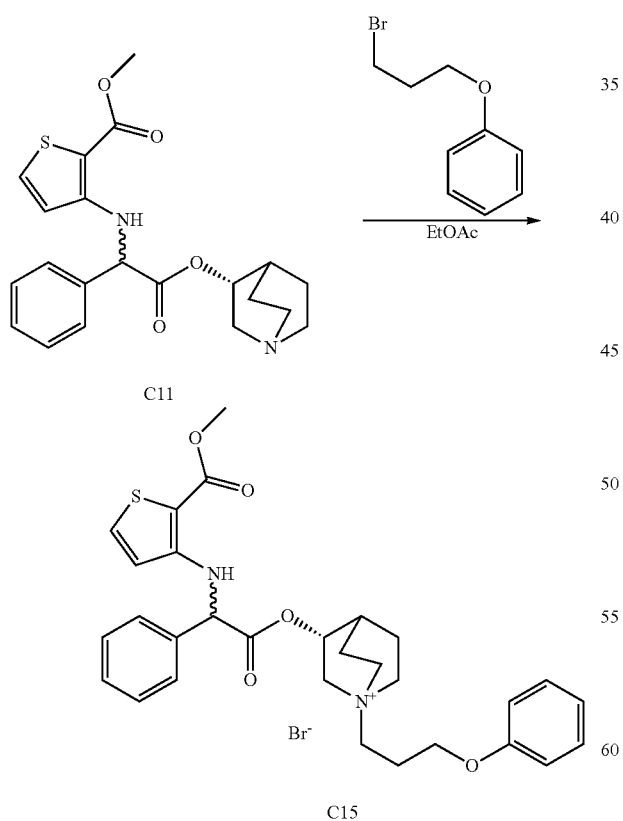

Scheme 8

C11

C15

(3-Bromopropoxy)benzene (19.7 μl, 0.12 mmol) was added to a solution of methyl 3-(2-oxo-1-phenyl-2-((R)-quinuclidin-3-yloxy)ethylamino)thiophene-2-carboxylate (C11) (50 mg, 0.12 mmol) in EtOAc (2 ml). The reaction mixture was stirred at room temperature overnight. The solvent was evaporated, and the residue was triturated with $Et_2O$ and then purified by preparative HPLC (Eluent: $CH_3CN/H_2O$) to obtain (3R)-3-(2-(2-(methoxycarbonyl)thiophen-3-ylamino)-2-phenylacetoxy)-1-(3-phenoxypropyl)-1-azoniabicyclo[2.2.2]octane bromide (25.3 mg, 32.9% yield).

$^1$H NMR (300 MHz, DMSO-$d_6$) δ ppm 7.78 and 7.83 (d, 1H), 7.61-7.71 (m, 1H), 7.21-7.57 (m, 6H), 6.83-7.03 (m, 4H), 6.65 and 6.73 (d, 1H), 5.59 and 5.68 (d, 1H), 5.02-5.26 (m, 1H), 3.82-4.19 (m, 4H), 3.78 (s, 3H), 3.34-3.73 (m, 5H), 2.81-3.14 (m, 1H), 1.43-2.43 (m, 7H);

LC-MS (ESI POS): 535.43 (M+).

Example 8

Preparation of (3R)-3-(2-(2-(methoxycarbonyl)thiophen-3-ylamino)-2-phenylacetoxy)-1-(2-oxo-2-(pyridin-2-yl)ethyl)-1-azoniabicyclo[2.2.2]octane 2,2,2-trifluoroacetate 2,2,2-trifluoroacetate anion (C16)

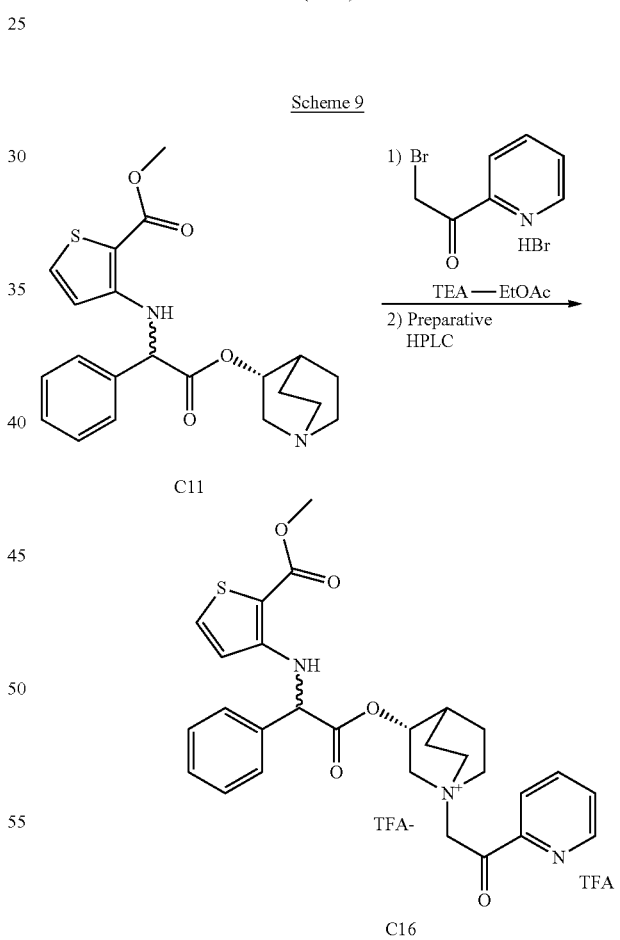

Scheme 9

C11

C16

2-Bromo-1-(pyridin-2-yl)ethanone hydrobromide (35.1 mg, 0.12 mmol) was added to a solution of methyl 3-(2-oxo-1-phenyl-2-((R)-quinuclidin-3-yloxy)ethylamino)thiophene-2-carboxylate (C11) (50 mg, 0.12 mmol) and TEA (17.4 μl, 0.12 mmol) in EtOAc (2 ml). The reaction mixture was stirred at room temperature for two days, and then the solvent was removed under vacuum. The crude product was triturated with Et₂O and filtered. The compound was further purified by preparative HPLC (Eluent: CH₃CN/H₂O) and then by preparative HPLC (Eluent: CH₃CN/H₂O/TFA) to obtain the title compound (15.3 mg, 16.4% yield).

¹H NMR (300 MHz, DMSO-d₆) δ ppm 8.66-8.83 (m, 1H), 7.94-8.25 (m, 2H), 7.70-7.87 (m, 2H), 7.61-7.70 (m, 1H), 7.28-7.57 (m, 5H), 6.72 and 6.74 (d, 1H), 5.67 and 5.72 (d, 1H), 5.24-5.30 (m, 1H), 5.22 and 5.29 (s, 2H), 4.01-4.25 (m, 1H), 3.78 (s, 3H), 3.51-3.92 (m, 5H), 2.16-2.24 and 2.33-2.46 (m, 1H), 1.40-2.13 (m, 4H);

LC-MS (ESI POS): 520.39 (M+).

Example 9

Preparation of (3R)-1-(4-fluorophenethyl)-3-(2-(2-(methoxycarbonyl)thiophen-3-ylamino)-2-phenylacetoxy)-1-azoniabicyclo[2.2.2]octane 2,2,2-trifluoroacetate (C17)

Scheme 10

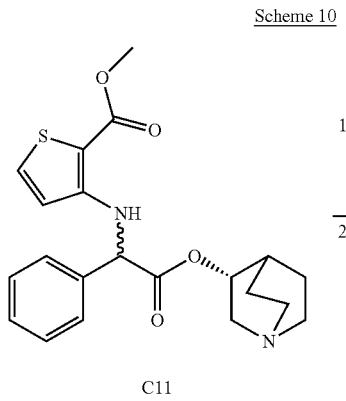

C11

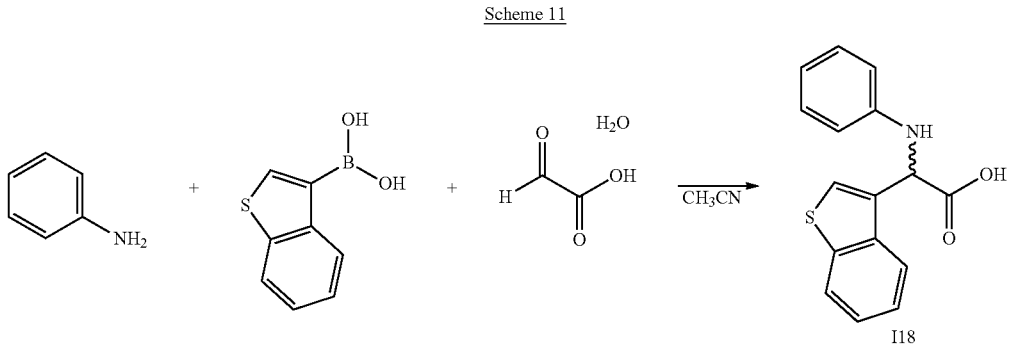

C17

1-(2-Bromoethyl)-4-fluorobenzene (25.4 μl, 0.12 mmol) was added to a solution of methyl 3-(2-oxo-1-phenyl-2-((R)-quinuclidin-3-yloxy)ethylamino)thiophene-2-carboxylate (C11) (50 mg, 0.12 mmol) in EtOAc (2 ml). The reaction mixture was stirred at room temperature overnight. The solvent was evaporated, and the residue was triturated with Et₂O. The compound was first purified by preparative HPLC (Eluent: CH₃CN/H₂O) and then by preparative HPLC (Eluent: CH₃CN/H₂O/TFA) to obtain (3R)-1-(4-fluorophenethyl)-3-(2-(2-(methoxycarbonyl)thiophen-3-ylamino)-2-phenylacetoxy)-1-azoniabicyclo[2.2.2]octane 2,2,2-trifluoroacetate (15 mg, 18.9% yield).

¹H NMR (300 MHz, DMSO-d₆) δ ppm 7.78 and 7.84 (d, 1H), 7.62-7.72 (m, 1H), 7.03-7.57 (m, 9H), 6.66 and 6.73 (d, 1H), 5.60 and 5.68 (d, 1H), 5.00-5.35 (m, 1H), 3.82-3.98 (m, 1H), 3.78 and 3.79 (s, 3H), 3.32-3.62 (m, 6H), 2.76-3.18 (m, 3H), 2.10-2.20 and 2.32-2.42 (m, 1H), 1.36-2.09 (m, 4H);

LC-MS (ESI POS): 523.39 (M+).

Example 10

Preparation of (3R)-3-(2-(benzo[b]thiophen-3-yl)-2-(phenylamino)acetoxy)-1-(2-oxo-2-(thiophen-2-yl)ethyl)-1-azoniabicyclo[2.2.2]octane bromide (C20)

Scheme 11

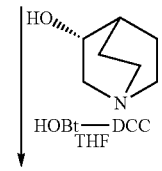

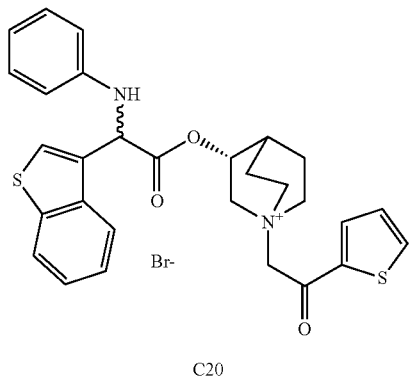

C20

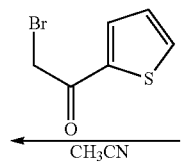

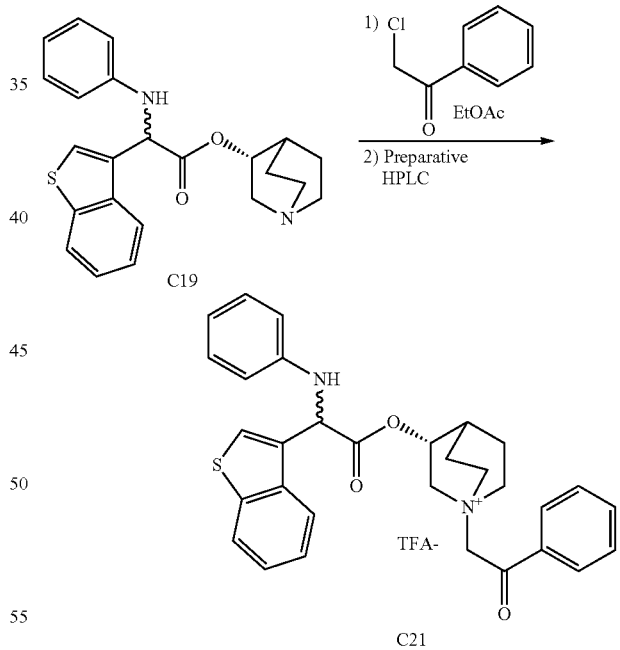

Preparation of 2-(benzo[b]thiophen-3-yl)-2-(phenylamino)acetic acid (I18)

Benzo[b]thiophen-3-ylboronic acid (387 mg, 2.17 mmol), aniline (202 mg, 2.17 mmol), and 2-oxoacetic acid hydrate (200 mg, 2.17 mmol) were dissolved in acetonitrile (12 ml) and then stirred at 100° C. under microwave irradiation for 1 hour. The solvent was evaporated, and the residue was dissolved in EtOAc and washed with sat.NaHCO$_3$. 2N HCl was added to the aqueous phase until pH was about 7, and the product was extracted with EtOAc. The organic phase was dried with Na$_2$SO$_4$, filtered and evaporated to obtain 2-(benzo[b]thiophen-3-yl)-2-(phenylamino)acetic acid (295 mg, 48% yield).

Preparation of (R)-quinuclidin-3-yl 2-(benzo[b]thiophen-3-yl)-2-(phenylamino)acetate (C19)

2-(Benzo[b]thiophen-3-yl)-2-(phenylamino)acetic acid (I18) (295 mg, 1.04 mmol), (R)-quinuclidin-3-ol (159 mg, 1.25 mmol), 1H-benzo[d][1,2,3]triazol-1-ol hydrate (191 mg, 1.25 mmol), and DCC (258 mg, 1.25 mmol) were dissolved in dry THF and stirred at room temperature for 15 hours. The solvent was evaporated, and the crude product was dissolved in EtOAc and washed with NaHCO$_3$, water and brine. The organic phase was dried with Na$_2$SO$_4$, filtered and evaporated under vacuum. The crude product was purified by flash chromatography (DCM/MeOH=9/1) to obtain (R)-quinuclidin-3-yl 2-(benzo[b]thiophen-3-yl)-2-(phenylamino) acetate (180 mg, 44% yield).

Preparation of (3R)-3-(2-(benzo[b]thiophen-3-yl)-2-(phenylamino)acetoxy)-1-(2-oxo-2-(thiophen-2-yl)ethyl)-1-azoniabicyclo[2.2.2]octane bromide (C20)

(R)-quinuclidin-3-yl 2-(benzo[b]thiophen-3-yl)-2-(phenylamino)acetate (C19) (90 mg, 0.23 mmol) was dissolved in EtOAc (3 ml), and 2-bromo-1-(thiophen-2-yl)ethanone (51.7 mg, 0.25 mmol) was added. The reaction mixture was stirred at room temperature overnight. The crude was purified by flash chromatography (DCM/MeOH=9/1) to obtain (3R)-3-(2-(benzo[b]thiophen-3-yl)-2-(phenylamino)acetoxy)-1-(2-oxo-2-(thiophen-2-yl)ethyl)-1-azoniabicyclo[2.2.2]octane bromide (50 mg, 36.5% yield).

$^1$H NMR (300 MHz, DMSO-d$_6$) ppm 8.21 (td, 1H) 7.99-8.18 (m, 3H) 7.89 (d, 1H) 7.30-7.54 (m, 3H) 7.12 (t, 2H) 6.71-6.91 (m, 2H) 6.63 (t, 1H) 6.35-6.52 (m, 1H) 5.69-5.92 (m, 1H) 5.14-5.35 (m, 1H) 4.81-5.09 (m, 2H) 3.98-4.24 (m, 1H) 3.79 (d, 1H) 3.54-3.67 (m, 3H) 3.12-3.42 (m, 1H) 2.30-2.42 (m, 1H) 1.52-2.12 (m, 4H);

LC-MS (ESI POS): 401.1 (M+).

Example 11

Preparation of (3R)-3-(2-(benzo[b]thiophen-3-yl)-2-(phenylamino)acetoxy)-1-(2-oxo-2-phenylethyl)-1-azoniabicyclo[2.2.2]octane trifluoroacetate (C21)

Scheme 12

2-Chloro-1-phenylethanone (39.0 mg, 0.25 mmol) was added to a solution of (R)-quinuclidin-3-yl 2-(benzo[b]thiophen-3-yl)-2-(phenylamino)acetate (C19) (90 mg, 0.23 mmol) in EtOAc (3 ml). The reaction mixture was stirred at room temperature overnight. The solvent was evaporated, and the crude product was purified by preparative HPLC to obtain (3R)-3-(2-(benzo[b]thiophen-3-yl)-2-(phenylamino)acetoxy)-1-(2-oxo-2-phenylethyl)-1-azoniabicyclo[2.2.2]octane trifluoroacetate (37.2 mg, 26% yield).

¹H NMR (300 MHz, DMSO-d₆) ppm 8.08-8.24 (m, 1H) 7.85-8.08 (m, 4H) 7.69-7.84 (m, 1H) 7.56-7.69 (m, 2H) 7.34-7.54 (m, 2H) 7.12 (t, 2H) 6.81 (dd, 2H) 6.63 (t, 1H) 6.30-6.55 (m, 1H) 5.74-5.91 (m, 1H) 5.18-5.34 (m, 1H) 5.15 (s, 1H) 5.06 (s, 1H) 4.00-4.17 (m, 1H) 3.80 (d, 1H) 3.43-3.70 (m, 3H) 3.23-3.43 (m, 1H) 2.37 (t, 1H) 1.50-2.17 (m, 4H);

LC-MS (ESI POS): 401.1 (M+).

Example 12

Preparation of (R)-3-(2-(benzo[b]thiophen-3-yl)-2-(phenylamino)acetoxy)-1-(2-(4-hydroxyphenyl)-2-oxoethyl)-1-azoniabicyclo[2.2.2]octane bromide (C22)

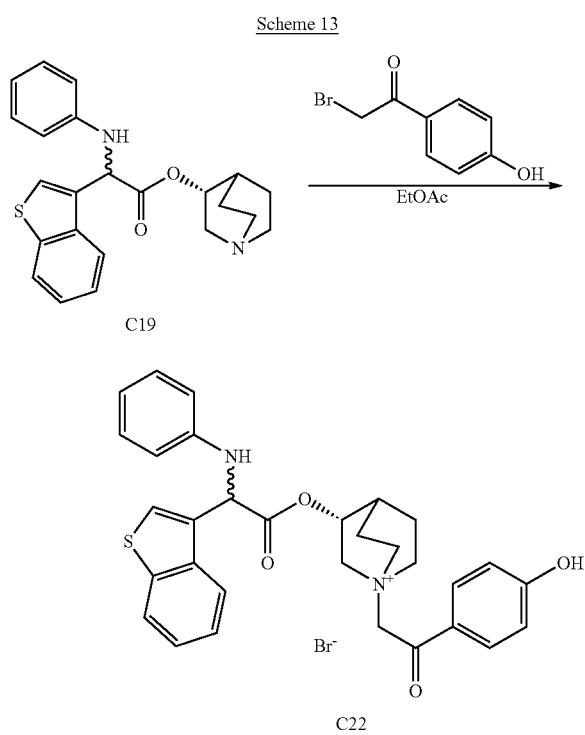

2-Bromo-1-(4-hydroxyphenyl)ethanone (54.8 mg, 0.25 mmol) was added portionwise to a solution of (R)-quinuclidin-3-yl 2-(benzo[b]thiophen-3-yl)-2-(phenylamino)acetate (C19) (100 mg, 0.25 mmol) in EtOAc (2 ml). The reaction mixture was stirred at room temperature overnight. The precipitate was filtered and washed with ethylacetate and then it was triturated with CH₃CN to obtain (R)-3-(2-(benzo[b]thiophen-3-yl)-2-(phenylamino)acetoxy)-1-(2-(4-hydroxyphenyl)-2-oxoethyl)-1-azoniabicyclo[2.2.2]octane bromide (101 mg, 65.3% yield).

¹H NMR (300 MHz, DMSO-d₆) δ ppm 9.84-11.39 (m, 1H), 8.07-8.21 (m, 1H), 7.97-8.07 (m, 1H), 7.76-7.95 (m, 3H), 7.34-7.54 (m, 2H), 7.02-7.20 (m, 2H), 6.85-6.96 (m, 2H), 6.72-6.85 (m, 2H), 6.53-6.68 (m, 1H), 6.46 (d, 1H), 5.65-6.02 (m, 1H), 5.15-5.37 (m, 1H), 4.82-5.09 (m, 1H), 3.98-4.20 (m, 1H), 3.43-3.88 (m, 5H), 2.01-2.13 and 2.33-2.42 (m, 1H), 1.32-2.03 (m, 4H);

LC-MS (ESI POS): 527.24 (M+).

Example 13

Preparation of (R)-3-(2-(benzo[b]thiophen-3-yl)-2-(phenylamino)acetoxy)-1-(2-oxo-2-(pyridin-2-ylamino)ethyl)-1-azoniabicyclo[2.2.2]octane chloride (C23)

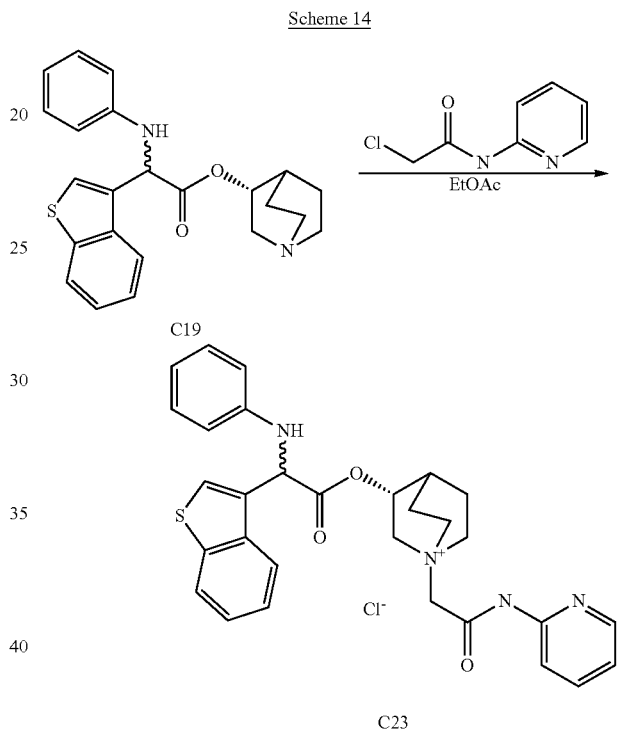

2-Chloro-N-(pyridin-2-yl)acetamide (43.5 mg, 0.25 mmol) was added portion-wise to a solution of (R)-quinuclidin-3-yl 2-(benzo[b]thiophen-3-yl)-2-(phenylamino)acetate (C19) (100 mg, 0.25 mmol) in EtOAc (2 ml). The reaction mixture was stirred at room temperature overnight. The solvent was evaporated, and the residue was purified by preparative HPLC (Eluent: CH₃CN, H₂O). The product was triturated with i-Pr₂O, filtered and dried under vacuum at room temperature to obtain (R)-3-(2-(benzo[b]thiophen-3-yl)-2-(phenylamino)acetoxy)-1-(2-oxo-2-(pyridin-2-ylamino)ethyl)-1-azoniabicyclo[2.2.2]octane chloride (31 mg, 21.6% yield).

¹H NMR (300 MHz, DMSO-d₆) δ ppm 11.04 and 11.10 (s, 1H), 8.32-8.45 (m, 1H), 8.07-8.18 (m, 1H), 7.96-8.07 (m, 2H), 7.82-7.95 (m, 1H), 7.90 (s, 1H), 7.34-7.50 (m, 2H), 7.22 (ddd, 1H), 7.03-7.17 (m, 2H), 6.71-6.87 (m, 2H), 6.61 (t, 1H), 6.47 (d, 1H), 5.76-5.86 (m, 1H), 5.10-5.32 (m, 1H), 4.20 and 4.30 (s, 2H), 3.97-4.12 (m, 1H), 3.43-3.90 (m, 4H), 3.09-3.25 (m, 1H), 2.03-2.12 and 2.30-2.40 (m, 1H), 1.32-2.02 (m, 4H);

LC-MS (ESI POS): 527.24 (M+).

Example 14

Preparation of (R)-3-(2-(benzo[b]thiophen-3-yl)-2-(phenylamino)acetoxy)-1-(2-oxo-2-(thiophen-3-yl)ethyl)-1-azoniabicyclo[2.2.2]octane bromide (C24)

Example 15

Preparation of (R)-3-(2-(benzo[b]thiophen-3-yl)-2-(phenylamino)acetoxy)-1-(2-oxo-2-(thiazol-2-yl)ethyl)-1-azoniabicyclo[2.2.2]octane bromide (C25)

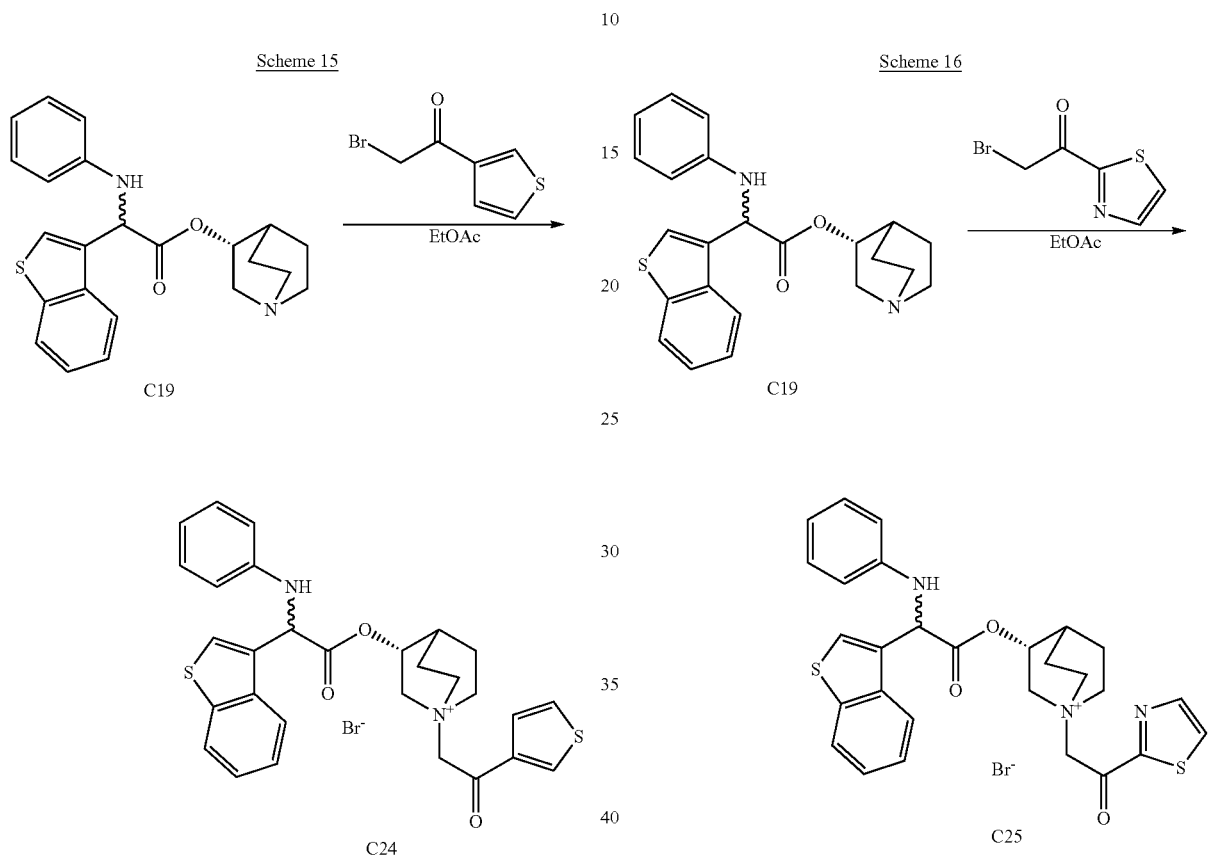

2-Bromo-1-(thiophen-3-yl)ethanone (52.2 mg, 0.25 mmol) was added portion-wise to a solution of (R)-quinuclidin-3-yl 2-(benzo[b]thiophen-3-yl)-2-(phenylamino)acetate (C19) (100 mg, 0.25 mmol) in EtOAc (2 ml). The reaction was stirred at room temperature for 3 hours. The precipitate was filtered, washed with EtOAc and purified by preparative HPLC (Eluent: CH$_3$CN, H$_2$O) to obtain (R)-3-(2-(benzo[b]thiophen-3-yl)-2-(phenylamino)acetoxy)-1-(2-oxo-2-(thiophen-3-yl)ethyl)-1-azoniabicyclo[2.2.2]octane bromide (32 mg, 21.0% yield).

$^1$H NMR (300 MHz, DMSO-d$_6$) δ ppm 8.59 and 8.64 (dd, 1H), 8.11 and 8.15 (d, 1H), 8.03 (d, 1H), 7.89 and 7.91 (s, 1H), 7.74 (dd, 1H), 7.54 and 7.58 (dd, 1H), 7.34-7.52 (m, 2H), 7.04-7.20 (m, 2H), 6.75-6.91 (m, 2H), 6.56-6.70 (m, 1H), 6.46 (d, 1H), 5.74-5.89 (m, 1H), 5.16-5.32 (m, 1H), 4.77-5.06 (m, 1H), 3.95-4.21 (m, 1H), 3.32-3.86 (m, 5H), 2.05-2.13 and 2.31-2.42 (m, 1H), 1.31-2.02 (m, 4H);

LC-MS (ESI POS): 516.98 (M+).

2-Bromo-1-(thiazol-2-yl)ethanone (52.5 mg, 0.25 mmol) was added portion-wise to a solution of (R)-quinuclidin-3-yl 2-(benzo[b]thiophen-3-yl)-2-(phenylamino)acetate (C19) (100 mg, 0.25 mmol) in EtOAc (2 ml). The reaction mixture was stirred at room temperature overnight. The precipitate was filtered, washed with EtOAc and purified by preparative HPLC (Eluent: CH$_3$CN, H$_2$O) to obtain (R)-3-(2-(benzo[b]thiophen-3-yl)-2-(phenylamino)acetoxy)-1-(2-oxo-2-(thiazol-2-yl)ethyl)-1-azoniabicyclo[2.2.2]octane bromide (42 mg, 27.5% yield).

$^1$H NMR (300 MHz, DMSO-d$_6$) δ ppm 8.35-8.43 (m, 1H), 8.23 and 8.25 (d, 1H), 8.07-8.17 (m, 1H), 7.98-8.07 (m, 1H), 7.90 and 7.91 (s, 1H), 7.35-7.54 (m, 2H), 7.02-7.20 (m, 2H), 6.73-6.88 (m, 2H), 6.56-6.70 (m, 1H), 6.46 (d, 1H), 5.77-5.87 (m, 1H), 5.20-5.29 (m, 1H), 4.92-5.20 (m, 1H), 3.97-4.23 (m, 1H), 3.32-3.90 (m, 5H), 2.05-2.16 and 2.30-2.42 (m, 1H), 1.31-2.04 (m, 4H);

LC-MS (ESI POS): 518.21 (M+).

Example 16

Preparation of (R)—((R)-quinuclidin-3-yl) 2-(benzo[b]thiophen-3-yl)-2-(phenylamino)acetate (Diastereomer 1 of C19) and (S)—((R)-quinuclidin-3-yl) 2-(benzo[b]thiophen-3-yl)-2-(phenylamino)acetate (Diastereomer 2 of C19)

Scheme 17

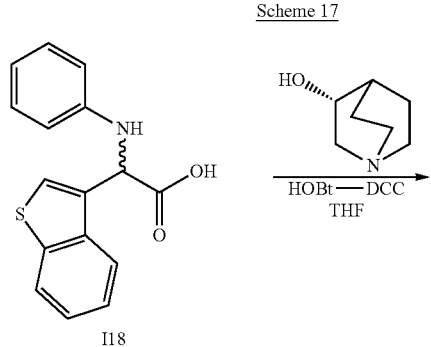

A solution of 2-(benzo[b]thiophen-3-yl)-2-(phenylamino)acetic acid (I18) (2.75 g, 9.71 mmol), 1H-benzo[d][1,2,3]triazol-1-ol hydrate (1.78 g, 11.6 mmol), and N,N'-methanediylidenedicyclohexanamine (2.40 g, 11.6 mmol) in dry THF (80 ml) was stirred at r.t. for 1 hour. (R)-quinuclidin-3-ol (1.48 g, 11.6 mmol) was added, and stirring was continued overnight. The solvent was evaporated, and the residue was portioned between EtOAc and sat. NaHCO$_3$; the organic layer was washed with brine, dried over Na$_2$SO$_4$, filtered and evaporated. The residue was purified by flash chromatography (CH$_3$CN/MeOH=75/25+0.2% NH$_4$OH) to collect first (R)—((R)-quinuclidin-3-yl) 2-(benzo[b]thiophen-3-yl)-2-(phenylamino)acetate (1.1 g, 28.9% yield, diastereomer 1 of C19), then (R)-quinuclidin-3-yl 2-(benzo[b]thiophen-3-yl)-2-(phenylamino)acetate (1.1 g, 28.9% yield, mixture of diastereomers) and finally (S)—((R)-quinuclidin-3-yl) 2-(benzo[b]thiophen-3-yl)-2-(phenylamino)acetate (0.4 g, 10.5% yield, diastereomer 2 of C19).

Diastereomer 1 of C19: $^1$H NMR (300 MHz, DMSO-d$_6$) δ ppm 8.06-8.20 (m, 1H), 7.95-8.06 (m, 1H), 7.86 (s, 1H), 7.33-7.50 (m, 2H), 7.01-7.16 (m, 2H), 6.73-6.85 (m, 2H), 6.55-6.67 (m, 1H), 6.38 (d, 1H), 5.72 (d, 1H), 4.61-4.76 (m, 1H), 2.92 (ddd, 1H), 2.55-2.70 (m, 3H), 1.94-2.18 (m, 2H), 1.80-1.94 (m, 1H), 1.31-1.62 (m, 3H), 1.03-1.31 (m, 1H);

LC-MS (ESI POS): 393.00 (M+).

Diastereomer 2 of C19: $^1$H NMR (300 MHz, DMSO-d$_6$) □ ppm 8.13 (dd, 1H), 7.92-8.06 (m, 1H), 7.83 (s, 1H), 7.43 (m, 2H), 6.95-7.18 (m, 2H), 6.67-6.85 (m, 2H), 6.49-6.66 (m, 1H), 6.37 (d, 1H), 5.71 (d, 1H), 4.55-4.93 (m, 1H), 2.98-3.16 (m, 1H), 2.53-2.61 (m, 4H), 2.32-2.48 (m, 1H), 1.59-1.71 (m, 1H), 1.28-1.58 (m, 3H), 0.89-1.15 (m, 1H);

LC-MS (ESI POS): 393.22 (M+).

Example 17

Preparation of (R)-3-((R)-2-(benzo[b]thiophen-3-yl)-2-(phenylamino)acetoxy)-1-(2-oxo-2-(thiophen-2-yl)ethyl)-1-azoniabicyclo[2.2.2]octane chloride (Diastereomer 1 of C20)

Scheme 18

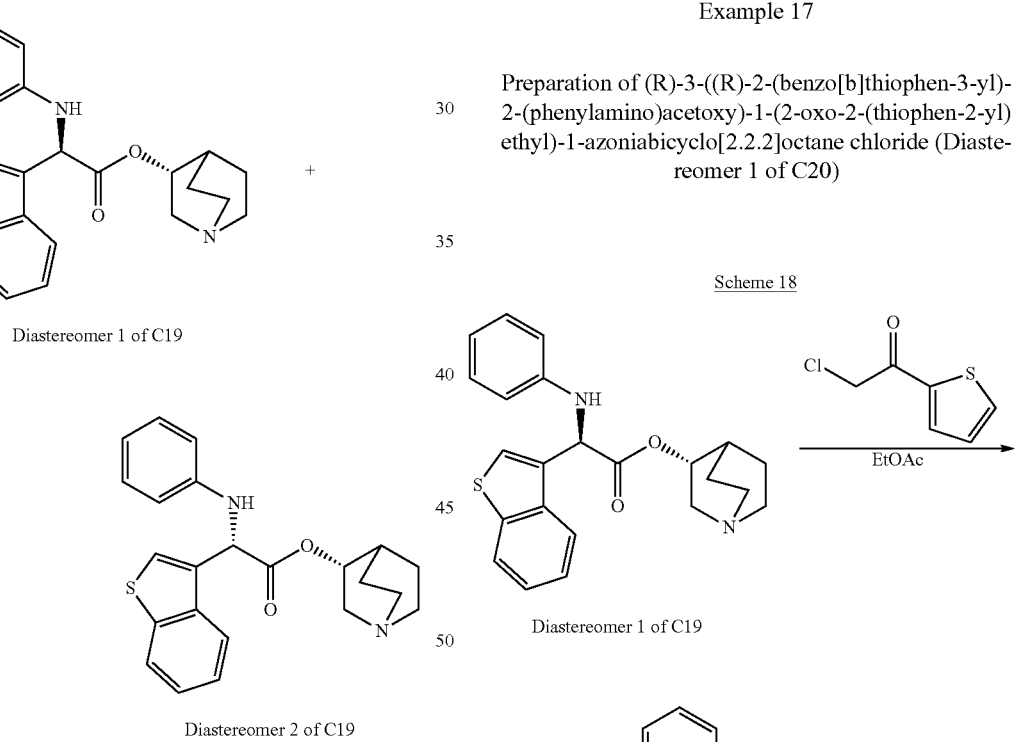

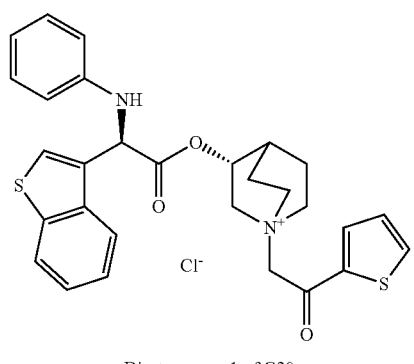

Diastereomer 1 of C20

2-Chloro-1-(thiophen-2-yl)ethanone (32.7 mg, 0.20 mmol) was added to a solution of (R)—((R)-quinuclidin-3-yl) 2-(benzo[b]thiophen-3-yl)-2-(phenylamino)acetate (diastereomer 1 of C19) (80 mg, 0.20 mmol) in EtOAc (3 ml). The reaction was stirred at r.t. overnight. Diethylether (10 ml) was added, and the precipitate was collected and dried under vacuum to obtain (R)-3-((R)-2-(benzo[b]thiophen-3-yl)-2-(phenylamino)acetoxy)-1-(2-oxo-2-(thiophen-2-yl)ethyl)-1-azoniabicyclo[2.2.2]octane chloride (101 mg, 90% yield).

$^1$H NMR (300 MHz, DMSO-d$_6$) δ ppm 8.21 (dd, 1H), 7.98-8.15 (m, 3H), 7.91 (s, 1H), 7.37-7.56 (m, 2H), 7.35 (dd, 1H), 7.01-7.19 (m, 2H), 6.82 (m, 2H), 6.57-6.68 (m, 1H), 6.49 (d, 1H), 5.83 (d, 1H), 5.17-5.32 (m, 1H), 5.00 (s, 2H), 3.94-4.21 (m, 1H), 3.46-3.78 (m, 4H), 3.33-3.44 (m, 1H), 2.31-2.39 (m, 1H), 1.65-2.14 (m, 4H);

LC-MS (ESI POS): 517.19 (M+).

Example 18

Preparation of (R)-3-((R)-2-(benzo[b]thiophen-3-yl)-2-(phenylamino)acetoxy)-1-(2-oxo-2-phenylethyl)-1-azoniabicyclo[2.2.2]octane chloride (Diastereomer 1 of C21)

of C19) (250 mg, 0.64 mmol) in CH$_3$CN (3 ml). The reaction mixture was stirred at r.t. overnight, and then the solvent was evaporated and the residue was triturated with Et$_2$O. The crude was purified by preparative HPLC (Eluent: CH$_3$CN/H$_2$O), to obtain (R)-3-((R)-2-(benzo[b]thiophen-3-yl)-2-(phenylamino)acetoxy)-1-(2-oxo-2-phenylethyl)-1-azoniabicyclo[2.2.2]octane chloride (210 mg, 60.3% yield).

$^1$H NMR (300 MHz, DMSO-d$_6$) δ ppm 8.12 (d, 1H), 8.04 (d, 1H), 7.92-8.00 (m, 2H), 7.90 (s, 1H), 7.71-7.81 (m, 1H), 7.55-7.67 (m, 2H), 7.46-7.53 (m, 1H), 7.37-7.46 (m, 1H), 7.06-7.19 (m, 2H), 6.75-6.88 (m, 2H), 6.58-6.69 (m, 1H), 6.48 (d, 1H), 5.84 (d, 1H), 5.17-5.36 (m, 1H), 4.96-5.16 (m, 2H), 3.98-4.20 (m, 1H), 3.45-3.74 (m, 4H), 3.33-3.45 (m, 1H), 2.32-2.42 (m, 1H), 1.69-2.22 (m, 4H);

LC-MS (ESI POS): 511.11 (M+).

Example 19

Preparation of (R)-3-((S)-2-(benzo[b]thiophen-3-yl)-2-(phenylamino)acetoxy)-1-(2-oxo-2-(thiophen-2-yl)ethyl)-1-azoniabicyclo[2.2.2]octane chloride (Diastereomer 2 of C20)

Scheme 19

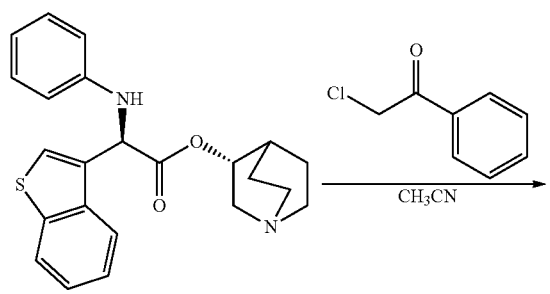

Diastereomer 1 of C19

Scheme 20

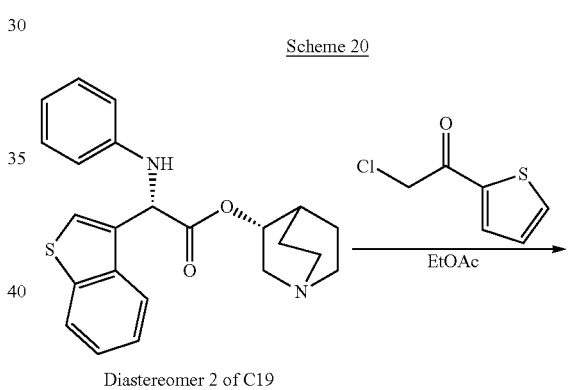

Diastereomer 2 of C19

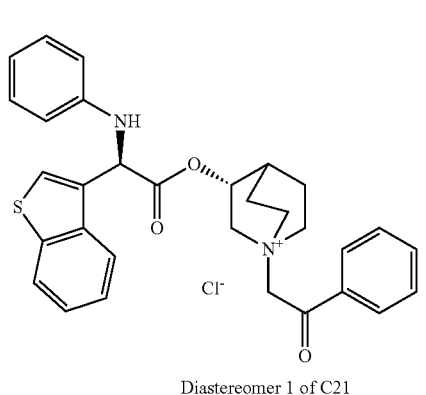

Diastereomer 1 of C21

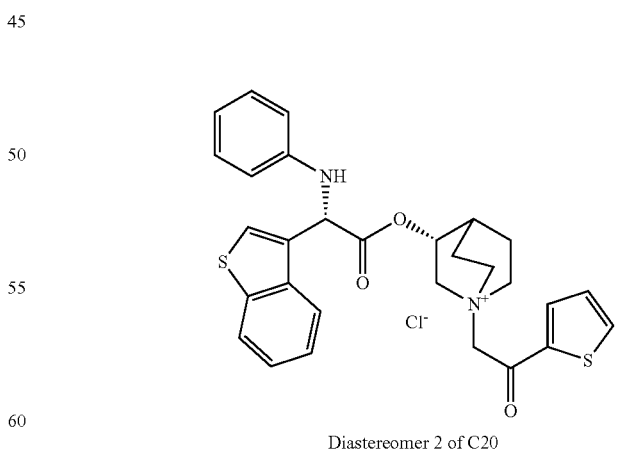

Diastereomer 2 of C20

2-Chloro-1-phenylethanone (98 mg, 0.64 mmol) was added to a solution of (R)—((R)-quinuclidin-3-yl) 2-(benzo[b]thiophen-3-yl)-2-(phenylamino)acetate (diastereomer 1

To a solution of (S)—((R)-quinuclidin-3-yl) 2-(benzo[b]thiophen-3-yl)-2-(phenylamino)acetate (diastereomer 2 of C19) (62 mg, 0.16 mmol) in ethyl acetate (3 ml), was added 2-chloro-1-(thiophen-2-yl)ethanone (25.4 mg, 0.16 mmol), and the reaction mixture was stirred at r.t. overnight. Diethyl ether (10 ml) was added, and the precipitate was filtered and dried under vacuum to obtain (R)-3-((S)-2-(benzo[b]thiophen-3-yl)-2-(phenylamino)acetoxy)-1-(2-oxo-2-(thiophen-2-yl)ethyl)-1-azoniabicyclo[2.2.2]octane chloride (75 mg, 86% yield).

$^1$H NMR (300 MHz, DMSO-d$_6$) δ ppm 8.22 (dd, 1H), 8.15 (dd, 1H), 8.10 (dd, 1H), 8.03 (dd, 1H), 7.92 (s, 1H), 7.38-7.63 (m, 2H), 7.36 (dd, 1H), 7.00-7.20 (m, 2H), 6.72-6.90 (m, 2H), 6.63 (t, 1H), 6.49 (d, 1H), 5.75-5.84 (m, 1H), 5.15-5.40 (m, 1H), 4.89-5.15 (m, 2H), 4.12 (dd, 1H), 3.82 (d, 1H), 3.45-3.72 (m, 4H), 2.03-2.14 (m, 1H), 1.78-2.03 (m, 2H), 1.56-1.77 (m, 1H), 1.29-1.56 (m, 1H);

LC-MS (ESI POS): 517.21 (M+).

Example 20

Preparation of (R)-3-((S)-2-(benzo[b]thiophen-3-yl)-2-(phenylamino)acetoxy)-1-(2-oxo-2-phenylethyl)-1-azoniabicyclo[2.2.2]octane chloride (Diastereomer 2 of C21)

Scheme 21

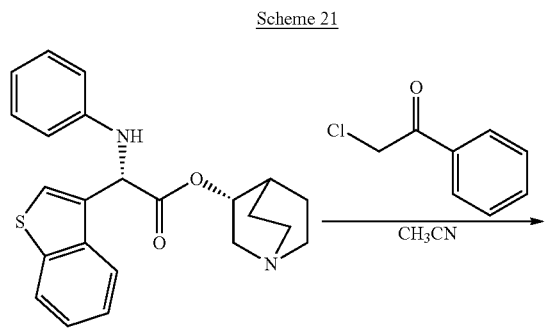

Diastereomer 2 of C19

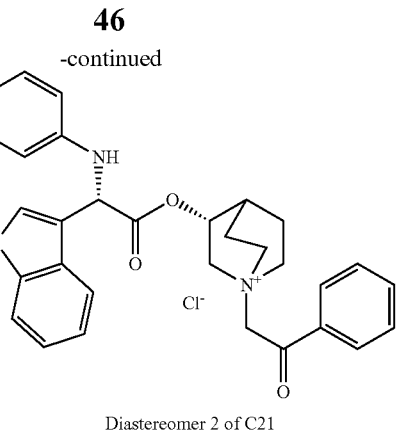

Diastereomer 2 of C21

A solution of (S)—((R)-quinuclidin-3-yl) 2-(benzo[b]thiophen-3-yl)-2-(phenylamino)acetate (diastereomer 2 of C19) (230 mg, 0.586 mmol) and 2-chloro-1-phenylethanone (91 mg, 0.586 mmol) in dry CH$_3$CN (2 ml) was stirred at r.t. for 24 hours. Then the solvent was evaporated and the residue was purified by preparative HPLC (Eluent: CH$_3$CN/H$_2$O) to obtain (R)-3-((S)-2-(benzo[b]thiophen-3-yl)-2-(phenylamino)acetoxy)-1-(2-oxo-2-phenylethyl)-1-azoniabicyclo[2.2.2]octane chloride (102 mg, 31.8% yield).

$^1$H NMR (300 MHz, DMSO-d$_6$) δ ppm 8.16 (d, 1H), 7.96-8.09 (m, 3H), 7.93 (s, 1H), 7.68-7.84 (m, 1H), 7.54-7.68 (m, 2H), 7.25-7.54 (m, 2H), 6.96-7.24 (m, 2H), 6.71-6.92 (m, 2H), 6.56-6.71 (m, 1H), 6.49 (d, 1H), 5.68-5.94 (m, 1H), 5.22-5.38 (m, 1H), 5.01-5.21 (m, 2H), 4.12 (dd, 1H), 3.83 (d, 1H), 3.47-3.74 (m, 4H), 2.03-2.17 (m, 1H), 1.79-2.03 (m, 2H), 1.56-1.79 (m, 1H), 1.31-1.55 (m, 1H);

LC-MS (ESI POS): 511.26 (M+).

Example 21

Preparation of (3R)-3-(2-(benzo[b]thiophen-7-yl)-2-(phenylamino)acetoxy)-1-(2-oxo-2-phenylethyl)-1-azoniabicyclo[2.2.2]octane chloride (C28)

Scheme 22

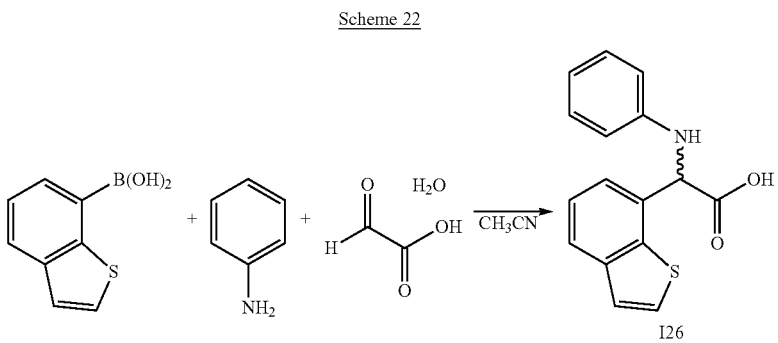

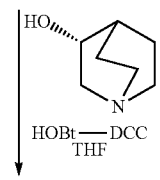

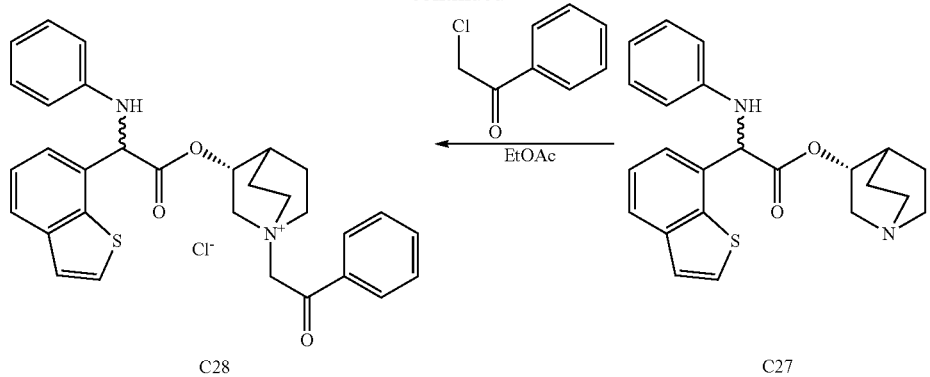

Preparation of 2-(benzo[b]thiophen-7-yl)-2-(phenylamino)acetic acid (I26)

A mixture of benzo[b]thiophen-7-ylboronic acid (300 mg, 1.68 mmol), aniline (157 mg, 1.68 mmol), and 2-oxoacetic acid hydrate (155 mg, 1.68 mmol) in CH₃CN (20 ml) was stirred at room temperature for 2 hours. The solvent was evaporated and the crude was purified by flash chromatography (DCM/MeOH=9/1) to obtain 2-(benzo[b]thiophen-7-yl)-2-(phenylamino)acetic acid (303 mg, 63.5% yield).

Preparation of (R)-quinuclidin-3-yl 2-(benzo[b]thiophen-7-yl)-2-(phenylamino)acetate (C27)

A mixture of 2-(benzo[b]thiophen-7-yl)-2-(phenylamino) acetic acid (I26) (303 mg, 1.07 mmol), (R)-quinuclidin-3-ol (136 mg, 1.07 mmol), DCC (221 mg, 1.07 mmol) and HOBT (164 mg, 1.07 mmol) in THF (20 ml) was stirred at r.t. for three days. THF was evaporated, and the crude product was taken up with EtOAc and washed twice with 2M K₂CO₃, and then with brine. The organic phase was dried over Na₂SO₄, filtered and evaporated to dryness. The crude was purified by flash chromatography (EtOAc/MeOH=9/1 to EtOAc/MeOH=9/1+0.5% NH₄OH) to obtain (R)-quinuclidin-3-yl 2-(benzo[b]thiophen-7-yl)-2-(phenylamino)acetate (180 mg, 42.9% yield).

Preparation of (3R)-3-(2-(benzo[b]thiophen-7-yl)-2-(phenylamino)acetoxy)-1-(2-oxo-2-phenylethyl)-1-azoniabicyclo[2.2.2]octane chloride (C28)

2-Chloro-1-phenylethanone (35.4 mg, 0.23 mmol) was added to a solution of (R)-quinuclidin-3-yl 2-(benzo[b]thiophen-7-yl)-2-(phenylamino)acetate (C27) (90 mg, 0.23 mmol) in EtOAc (3 ml). The reaction was stirred at room temperature overnight. The solvent was removed under vacuum and the crude was triturated with Et₂O. The compound was purified by preparative HPLC (Eluent: CH₃CN/H₂O) to obtain (3R)-3-(2-(benzo[b]thiophen-7-yl)-2-(phenylamino)acetoxy)-1-(2-oxo-2-phenylethyl)-1-azoniabicyclo[2.2.2]octane chloride (26.6 mg, 21.2% yield).

¹H NMR (300 MHz, DMSO-d₆) δ ppm 7.86-8.08 (m, 4H), 7.69-7.84 (m, 2H), 7.54-7.69 (m, 3H), 7.39-7.54 (m, 2H), 6.98-7.18 (m, 2H), 6.68-6.79 (m, 2H), 6.56-6.66 (m, 1H), 6.53 (d, 1H), 5.49-5.66 (m, 1H), 5.22-5.34 (m, 1H), 4.85-5.22 (m, 1H), 3.97-4.28 (m, 1H), 3.32-3.91 (m, 5H), 2.04-2.13 and 2.34-2.45 (m, 1H), 1.23-2.01 (m, 4H);

LC-MS (ESI POS): 511.26 (M+).

Example 22

Preparation of (3R)-3-(2-(benzo[b]thiophen-7-yl)-2-(phenylamino)acetoxy)-1-(2-oxo-2-(thiophen-2-yl)ethyl)-1-azoniabicyclo[2.2.2]octane chloride (C29)

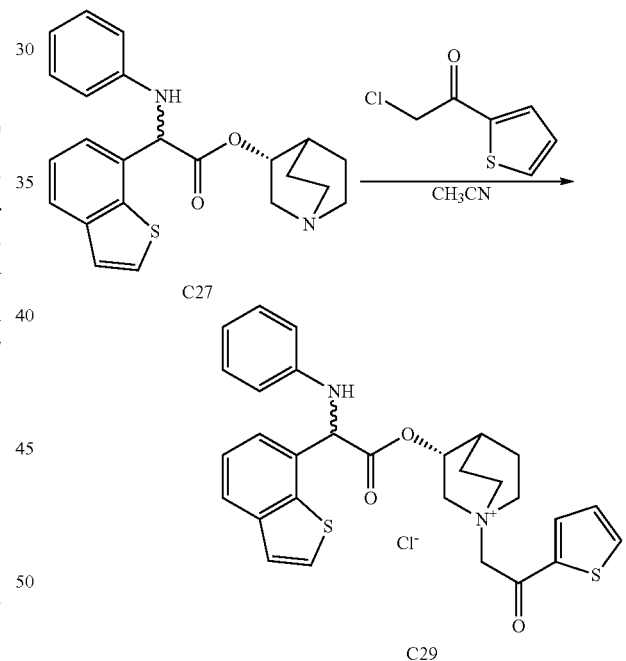

2-Chloro-1-(thiophen-2-yl)ethanone (36.8 mg, 0.23 mmol) was added to a solution of (R)-quinuclidin-3-yl 2-(benzo[b]thiophen-7-yl)-2-(phenylamino)acetate (C27) (90 mg, 0.23 mmol) in acetonitrile (3 ml). The reaction was stirred at r.t. overnight. The solvent was removed under vacuum, and the crude product was triturated with Et₂O. The compound was first purified by preparative HPLC (Eluent: CH₃CN/H₂O) and then by flash chromatography (DCM/MeOH=95/5) to obtain (3R)-3-(2-(benzo[b]thiophen-7-yl)-2-(phenylamino)acetoxy)-1-(2-oxo-2-(thiophen-2-yl)ethyl)-1-azoniabicyclo[2.2.2]octane chloride (20 mg, 16% yield).

$^1$H NMR (300 MHz, DMSO-$d_6$) δ ppm 8.15-8.30 (m, 1H), 8.05 (d, 1H), 7.84-7.93 (m, 1H), 7.78 (d, 1H), 7.51 (d, 1H), 7.39-7.63 (m, 2H), 7.34 (dd, 1H), 6.98-7.13 (m, 2H), 6.66-6.77 (m, 2H), 6.56-6.64 (m, 1H), 6.53 (d, 1H), 5.42-5.68 (m, 1H), 5.17-5.38 (m, 1H), 4.74-5.14 (m, 1H), 3.96-4.26 (m, 1H), 3.29-3.92 (m, 5H), 2.33-2.44 (m, 1H), 1.32-2.16 (m, 4H);

LC-MS (ESI POS): 517.19 (M+).

Example 23

Preparation of (3R)-3-(2-(benzo[b]thiophen-2-yl)-2-(phenylamino)acetoxy)-1-(2-oxo-2-phenylethyl)-1-azoniabicyclo[2.2.2]octane 2,2,2-trifluoroacetate (C32)

Preparation of (R)-quinuclidin-3-yl 2-(benzo[b]thiophen-2-yl)-2-(phenylamino)acetate (C31)

A mixture of 2-(benzo[b]thiophen-2-yl)-2-(phenylamino)acetic acid (I30) (796 mg, 2.81 mmol), (R)-quinuclidin-3-ol (429 mg, 3.37 mmol), HOBT (516 mg, 3.37 mmol), and DCC (696 mg, 3.37 mmol) in THF (30 ml) was stirred at r.t. overnight. THF was evaporated, and the crude product was partitioned between EtOAc and 1M $K_2CO_3$. The organic phase was dried over $Na_2SO_4$, filtered and evaporated to dryness. The crude product was purified by flash chromatography (DCM/MeOH=98/2) to obtain (R)-quinuclidin-3-yl 2-(benzo[b]thiophen-2-yl)-2-(phenylamino)acetate (361 mg, 32.7% yield).

Scheme 24

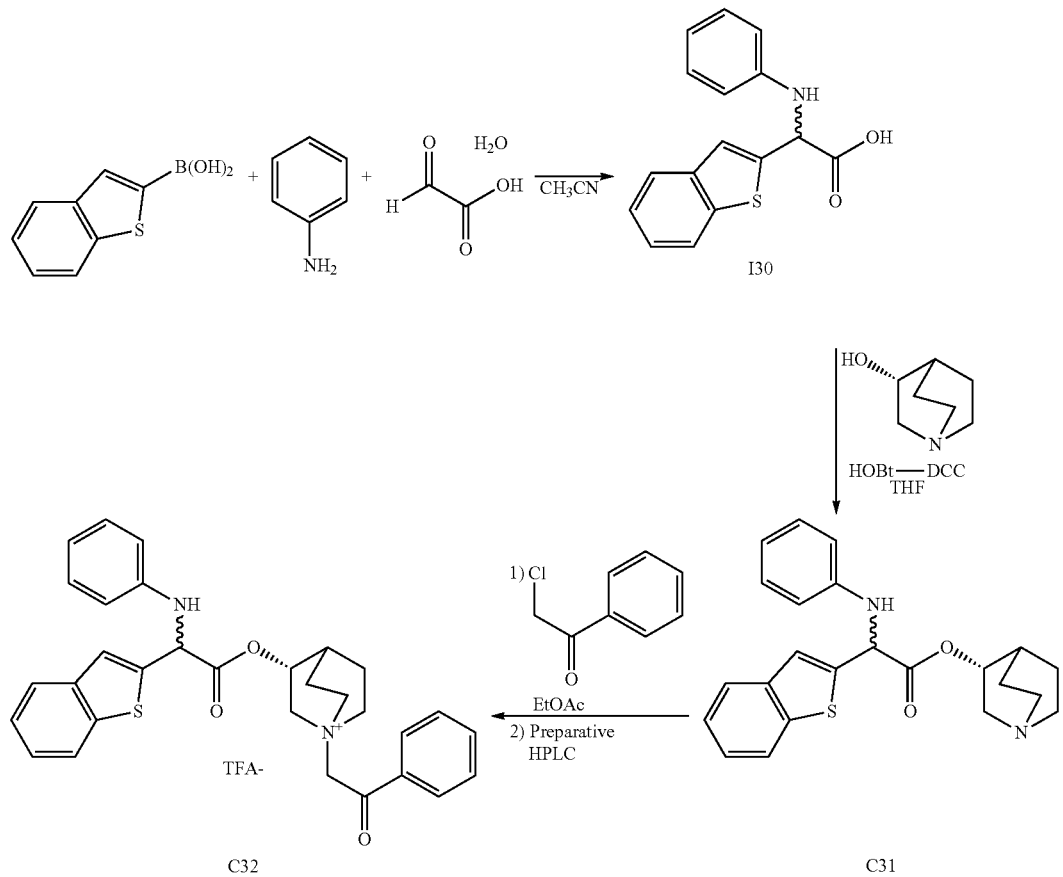

Preparation of 2-(benzo[b]thiophen-2-yl)-2-(phenylamino)acetic acid (I30)

A mixture of benzo[b]thiophen-2-ylboronic acid (500 mg, 2.81 mmol), aniline (240 µl, 2.81 mmol), and 2-oxoacetic acid hydrate (259 mg, 2.81 mmol) in acetonitrile (20 ml) was stirred at room temperature for three days. The solvent was evaporated to dryness and the crude was used as such in the next step.

Preparation of (3R)-3-(2-(benzo[b]thiophen-2-yl)-2-(phenylamino)acetoxy)-1-(2-oxo-2-phenylethyl)-1-azoniabicyclo[2.2.2]octane 2,2,2-trifluoroacetate (C32)

2-Chloro-1-phenylethanone (59.1 mg, 0.38 mmol) was added to a solution (R)-quinuclidin-3-yl 2-(benzo[b]thiophen-2-yl)-2-(phenylamino)acetate (C31) (150 mg, 0.38 mmol) in EtOAc (5 ml) and the reaction was stirred at r.t. for 20 hours. EtOAc was removed under vacuum and the solid was triturated with $Et_2O$ (2 ml). The compound was purified by preparative HPLC to obtain (3R)-3-(2-(benzo[b]thiophen-2-yl)-2-(phenylamino)acetoxy)-1-(2-oxo-2-phenylethyl)-1-azoniabicyclo[2.2.2]octane 2,2,2-trifluoroacetate (42.8 mg, 17.9% yield).

$^1$H NMR (300 MHz, DMSO-d$_6$) δ ppm 7.90-8.06 (m, 3H), 7.81-7.89 (m, 1H), 7.69-7.81 (m, 1H), 7.53-7.67 (m, 3H), 7.29-7.45 (m, 2H), 7.05-7.19 (m, 2H), 6.77-6.89 (m, 2H), 6.61-6.72 (m, 1H), 6.55 (br. s., 1H), 5.79 and 5.82 (s, 1H), 5.26-5.43 (m, 1H), 5.13 and 5.17 (s, 2H), 4.01-4.27 (m, 1H), 3.53-3.87 (m, 5H), 2.23-2.33 and 2.35-2.45 (m, 1H), 1.72-2.21 (m, 4H);

LC-MS (ESI POS): 511.21 (M+).

Example 24

Preparation of (3R)-3-(2-(benzo[b]thiophen-2-yl)-2-(phenylamino)acetoxy)-1-(2-oxo-2-(thiazol-2-yl)ethyl)-1-azoniabicyclo[2.2.2]octane 2,2,2-trifluoroacetate (C33)

Scheme 25

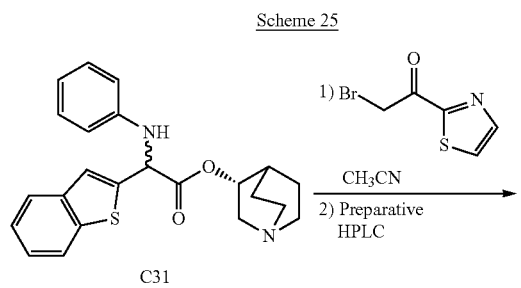

2-Bromo-1-(thiazol-2-yl)ethanone (42.0 mg, 0.20 mmol) was added to a solution of (R)-quinuclidin-3-yl 2-(benzo[b]thiophen-2-yl)-2-(phenylamino)acetate (C31) (80 mg, 0.20 mmol) in acetonitrile (2 ml). The reaction was stirred at r.t. overnight, and then a second portion of 2-bromo-1-(thiazol-2-yl)ethanone (12.6 mg, 0.06 mmol) was added and the stirring was kept for additional 4 hours. The solvent was evaporated, and the crude product was triturated with Et$_2$O and then purified by preparative HPLC to obtain (3R)-3-(2-(benzo[b]thiophen-2-yl)-2-(phenylamino)acetoxy)-1-(2-oxo-2-(thiazol-2-yl)ethyl)-1-azoniabicyclo[2.2.2]octane 2,2,2-trifluoroacetate (24 mg, 18.6% yield).

$^1$H NMR (300 MHz, DMSO-d$_6$) δ ppm 8.38 and 8.39 (d, 1H), 8.23 and 8.24 (d, 1H), 7.89-8.00 (m, 1H), 7.77-7.89 (m, 1H), 7.52-7.66 (m, 1H), 7.29-7.46 (m, 2H), 7.00-7.20 (m, 2H), 6.80-6.91 (m, 2H), 6.60-6.71 (m, 1H), 6.55 (br. s., 1H), 5.78 and 5.81 (s, 1H), 5.24-5.35 (m, 1H), 5.15 and 5.19 (s, 2H), 4.10-4.27 (m, 1H), 3.41-3.88 (m, 5H), 2.23-2.31 and 2.36-2.45 (m, 1H), 1.73-2.17 (m, 4H);

LC-MS (ESI POS): 518.18 (M+).

Example 25

Preparation of (3R)-3-(2-(benzo[b]thiophen-3-yl)-2-(methyl(phenyl)amino)acetoxy)-1-(2-oxo-2-phenylethyl)-1-azoniabicyclo[2.2.2]octane chloride (C36)

Scheme 26

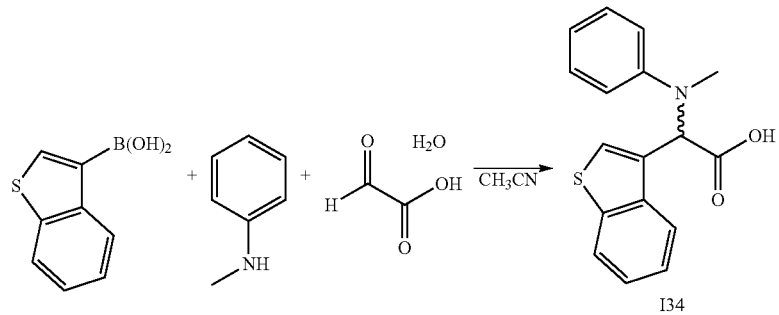

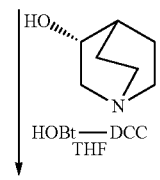

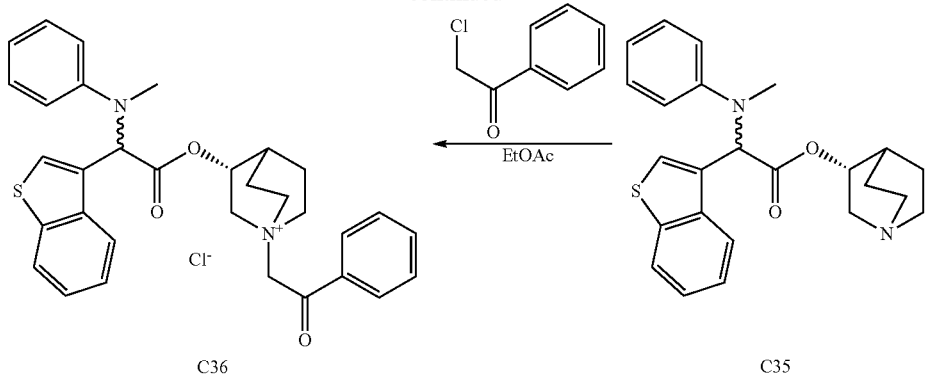

C36                  C35

Preparation of 2-(benzo[b]thiophen-3-yl)-2-(methyl(phenyl)amino)acetic acid (I34)

A mixture of benzo[b]thiophen-3-ylboronic acid (300 mg, 1.68 mmol), N-methylaniline (184 µl, 1.68 mmol) and 2-oxoacetic acid hydrate (155 mg, 1.65 mmol) in acetonitrile (20 ml) was stirred at room temperature for 2 hours. The solvent was removed under reduced pressure, and the crude product was purified by flash chromatography (DCM/MeOH=95/5) to obtain 2-(benzo[b]thiophen-3-yl)-2-(methyl(phenyl)amino)acetic acid (351 mg, 70% yield).

Preparation of (R)-quinuclidin-3-yl 2-(benzo[b]thiophen-3-yl)-2-(methyl(phenyl)amino)acetate (C35)

A mixture of 2-(benzo[b]thiophen-3-yl)-2-(methyl(phenyl)amino)acetic acid (I34) (351 mg, 1.18 mmol), (R)-quinuclidin-3-ol (180 mg, 1.42 mmol), DCC (292 mg, 1.42 mmol), and HOBT (217 mg, 1.42 mmol) in dry THF (20 ml) was stirred at room temperature overnight. The solvent was evaporated, and the crude product was portioned between EtOAc and 2M $K_2CO_3$. The organic phase was washed with 2M $K_2CO_3$ and brine, dried over $Na_2SO_4$, filtered and evaporated to dryness. The crude product was purified by flash chromatography (MeCN/MeOH=8/2+0.2% $NH_4OH$) to obtain (R)-quinuclidin-3-yl 2-(benzo[b]thiophen-3-yl)-2-(methyl(phenyl)amino)acetate (224 mg, 46.7% yield).

Preparation of (3R)-3-(2-(benzo[b]thiophen-3-yl)-2-(methyl(phenyl)amino)acetoxy)-1-(2-oxo-2-phenylethyl)-1-azoniabicyclo[2.2.2]octane chloride (C36)

2-Chloro-1-phenylethanone (42.6 mg, 0.27 mmol) was added to solution of (R)-quinuclidin-3-yl 2-(benzo[b]thiophen-3-yl)-2-(methyl(phenyl)amino)acetate (C35) (112 mg, 0.27 mmol) in acetonitrile (3 ml). The reaction was stirred at room temperature for 3 hours, and then the solvent was evaporated under vacuum. The residue was triturated with $Et_2O$, filtered and dried to obtain (3R)-3-(2-(benzo[b]thiophen-3-yl)-2-(methyl(phenyl)amino)acetoxy)-1-(2-oxo-2-phenylethyl)-1-azoniabicyclo[2.2.2]octane chloride (112.2 mg, 72.6% yield).

$^1$H NMR (300 MHz, DMSO-$d_6$) δ ppm 7.94-8.17 (m, 3H), 7.82-7.94 (m, 1H), 7.70-7.82 (m, 1H), 7.55-7.67 (m, 3H), 7.21-7.48 (m, 4H), 7.06 (dd, 2H), 6.80 (td, 1H), 6.28 and 6.30 (s, 1H), 5.30 (s, 2H), 5.21-5.61 (m, 1H), 4.05-4.39 (m, 1H), 3.49-3.89 (m, 5H), 2.72 and 2.74 (s, 3H), 2.22-2.43 (m, 1H), 1.94-2.16 (m, 2H), 1.70-1.94 (m, 1H), 1.37-1.70 (m, 1H);
LC-MS (ESI POS): 525.15 (M+).

Example 26

Preparation of (3R)-3-(2-(benzo[b]thiophen-3-yl)-2-(benzylamino)acetoxy)-1-(2-oxo-2-phenylethyl)-1-azoniabicyclo[2.2.2]octane 2,2,2-trifluoroacetate 2,2,2-trifluoroacetate anion (C39)

Scheme 27

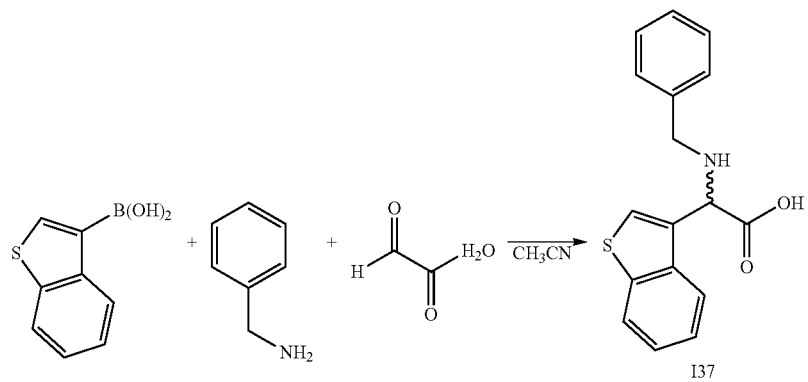

I37

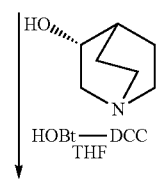

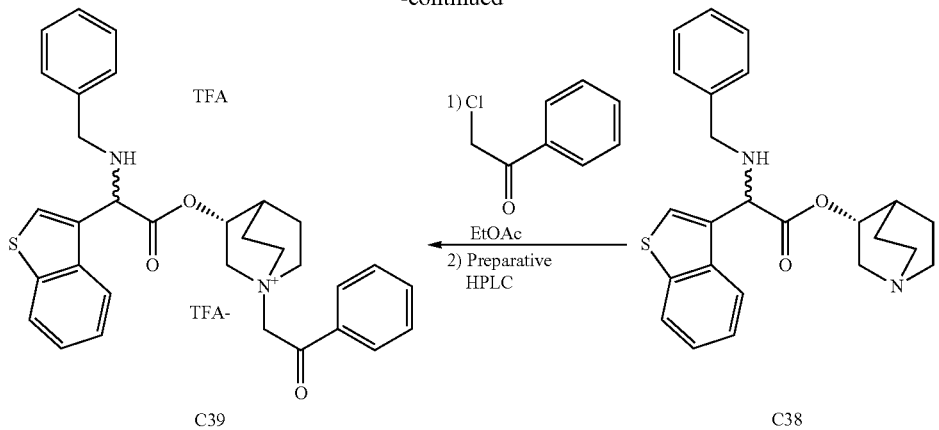

Preparation of 2-(benzo[b]thiophen-3-yl)-2-(benzylamino)acetic acid (I37)

A mixture of benzo[b]thiophen-3-ylboronic acid (300 mg, 1.68 mmol), phenylmethanamine (184 μl, 1.68 mmol) and 2-oxoacetic acid hydrate (155 mg, 1.68 mmol) in acetonitrile (20 ml) was stirred at room temperature for 2 hours. The solvent was removed and crude was triturated with $Et_2O$/$CH_3CN$ (9/1) to obtain 2-(benzo[b]thiophen-3-yl)-2-(benzylamino)acetic acid (303 mg, 60.5% yield).

Preparation of (R)-quinuclidin-3-yl 2-(benzo[b]thiophen-3-yl)-2-(benzylamino)acetate (C38)

A mixture of 2-(benzo[b]thiophen-3-yl)-2-(benzylamino)acetic acid (I37) (303 mg, 1.02 mmol), (R)-quinuclidin-3-ol (156 mg, 1.22 mmol), DCC (252 mg, 1.22 mmol), and HOBT (187 mg, 1.22 mmol) in dry THF (20 ml) was stirred at room temperature overnight. The solvent was evaporated, and the crude product was partitioned between EtOAc and 2M $K_2CO_3$. The organic phase was washed with 2M $K_2CO_3$ and brine, dried over $Na_2SO_4$, filtered and evaporated to dryness. The crude product was purified by flash chromatography ($CH_3CN$/MeOH=8/2+0.2% $NH_4OH$) to obtain (R)-quinuclidin-3-yl 2-(benzo[b]thiophen-3-yl)-2-(benzylamino)acetate (53 mg, 12.8% yield).

Preparation of (3R)-3-(2-(benzo[b]thiophen-3-yl)-2-(benzylamino)acetoxy)-1-(2-oxo-2-phenylethyl)-1-azoniabicyclo[2.2.2]octane 2,2,2-trifluoroacetate 2,2,2-trifluoroacetate anion (C39)

2-Chloro-1-phenylethanone (20.1 mg, 0.13 mmol) was added to a solution of (R)-quinuclidin-3-yl 2-(benzo[b]thiophen-3-yl)-2-(benzylamino)acetate (C38) (53 mg, 0.13 mmol) in $CH_3CN$ (3 ml). The reaction was stirred at r.t. for 5 hours, and then a second portion of 2-chloro-1-phenylethanone (6.05 mg, 0.04 mmol) was added and stirring was continued overnight. Then reaction was heated under microwave irradiation at 80° C. for 30 minutes. The solvent was evaporated and the crude was purified by preparative HPLC to obtain (3R)-3-(2-(benzo[b]thiophen-3-yl)-2-(benzylamino)acetoxy)-1-(2-oxo-2-phenylethyl)-1-azoniabicyclo[2.2.2]octane 2,2,2-trifluoroacetate 2,2,2-trifluoroacetate anion (34.1 mg, 34.7% yield).

$^1$H NMR (300 MHz, DMSO-$d_6$) δ ppm 8.01-8.16 (m, 3H), 7.87-8.01 (m, 2H), 7.69-7.82 (m, 1H), 7.30-7.68 (m, 9H), 5.52-5.96 (m, 1H), 5.24-5.45 (m, 1H), 5.09 and 5.14 (s, 2H), 3.95-4.39 (, 3H), 3.74-3.85 (m, 1H), 3.15-3.52 (m, 4H), 2.11-2.23 and 2.33-2.43 (m, 1H), 1.09-2.10 (m, 4H);

LC-MS (ESI POS): 525.25 (M+).

Example 27

Preparation of (3R)-3-(2-(benzo[b]thiophen-3-yl)-2-(3-fluorophenylamino)acetoxy)-1-(2-oxo-2-phenyl-ethyl)-1-azoniabicyclo[2.2.2]octane 2,2,2-trifluoro-acetate (C42)

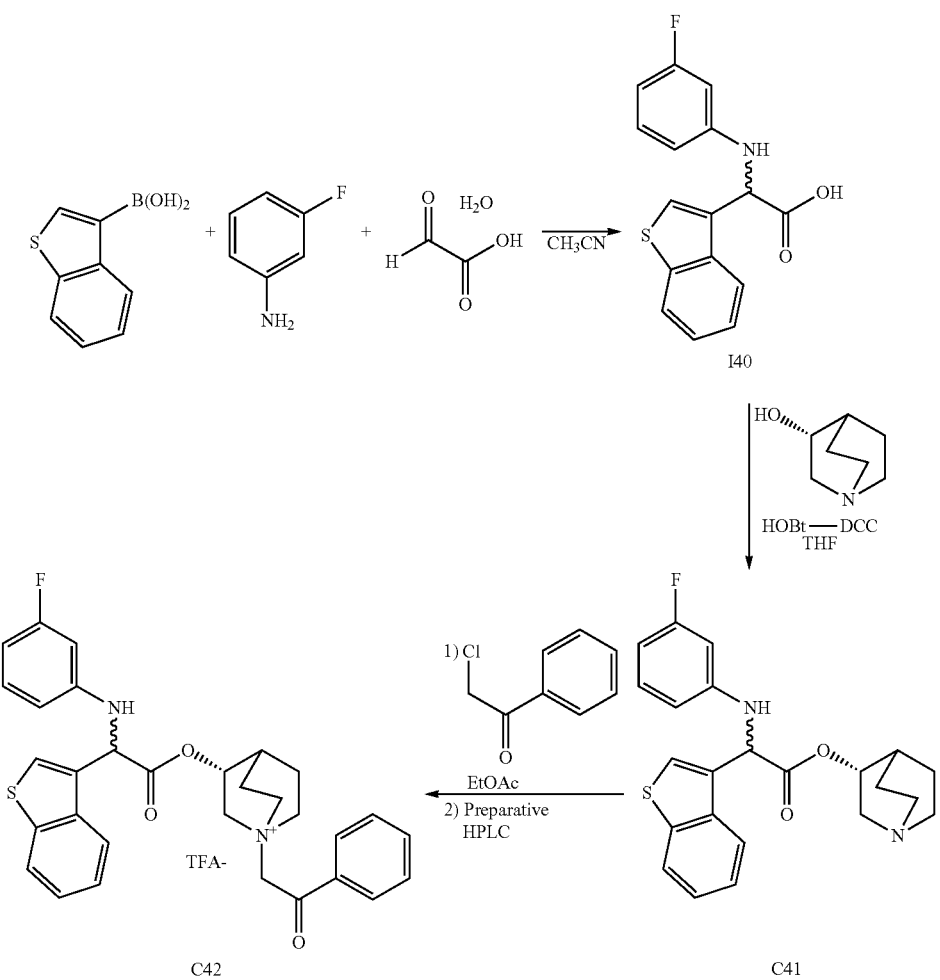

Scheme 28

Preparation of 2-(benzo[b]thiophen-3-yl)-2-(3-fluorophenylamino)acetic acid (I40)

A mixture of benzo[b]thiophen-3-ylboronic acid (400 mg, 2.25 mmol), 3-fluoroaniline (217 µl, 2.25 mmol), and 2-oxoacetic acid hydrate (207 mg, 2.25 mmol) in acetonitrile (20 ml) was stirred at room temperature for 4 hours. The solvent was removed under vacuum and the crude was used as such in the next step.

Preparation of (R)-quinuclidin-3-yl 2-(benzo[b]thiophen-3-yl)-2-(3-fluorophenylamino)acetate (C41)

A mixture of 2-(benzo[b]thiophen-3-yl)-2-(3-fluorophenylamino)acetic acid (I40) (677 mg, 2.25 mmol), (R)-quinuclidin-3-ol (343 mg, 2.70 mmol), HOBT (413 mg, 2.70 mmol), and DCC (556 mg, 2.70 mmol) in THF (20 ml) was stirred at room temperature overnight. THF was evaporated, and the crude product was partitioned between EtOAc and 1M K₂CO₃. The organic phase was dried over Na₂SO₄, filtered and evaporated to dryness. The crude product was purified by flash chromatography (DCM/MeOH=98/2 to 95/5) to obtain (R)-quinuclidin-3-yl 2-(benzo[b]thiophen-3-yl)-2-(3-fluorophenylamino)acetate (421 mg, 45.6% yield over two steps).

Preparation of (3R)-3-(2-(benzo[b]thiophen-3-yl)-2-(3-fluorophenylamino)acetoxy)-1-(2-oxo-2-phenyl-ethyl)-1-azoniabicyclo[2.2.2]octane 2,2,2-trifluoro-acetate (C42)

2-Chloro-1-phenylethanone (39.5 mg, 0.26 mmol) was added to a solution of (R)-quinuclidin-3-yl 2-(benzo[b]thiophen-3-yl)-2-(3-fluorophenylamino)acetate (C41) (105 mg, 0.26 mmol) in EtOAc (3 ml). The reaction was stirred at r.t. overnight, and then a second portion of 2-chloro-1-phenylethanone (11.9 mg, 0.07 mmol) was added and reaction was stirred at r.t. for additional 4 hours. EtOAc was evaporated, and the crude product was triturated with $Et_2O$ (2 ml). The compound was first purified by preparative HPLC and then by flash chromatography (DCM/MeOH=97/3 to 94/6) to obtain (3R)-3-(2-(benzo[b]thiophen-3-yl)-2-(3-fluorophenylamino)acetoxy)-1-(2-oxo-2-phenylethyl)-1-azoniabicyclo[2.2.2]octane 2,2,2-trifluoroacetate (45 mg; 27.4% yield).

$^1$H NMR (300 MHz, DMSO-$d_6$) δ ppm 8.09-8.20 (m, 1H), 7.86-8.08 (m, 4H), 7.36-7.82 (m, 5H), 7.02-7.19 (m, 1H), 6.71-6.90 (m, 1H), 6.55-6.69 (m, 2H), 6.32-6.47 (m, 1H), 5.86 (m, 1H), 5.23-5.34 (m, 1H), 5.08 and 5.15 (s, 2H), 3.98-4.24 (m, 1H), 3.78-3.88 (m, 1H), 3.28-3.65 (m, 4H), 2.05-2.15 and 2.31-2.44 (m, 1H), 1.31-2.04 (m, 4H);

LC-MS (ESI POS): 529.21 (M+).

Example 28

Preparation of (3R)-3-(2-(benzo[b]thiophen-3-yl)-2-(2-ethylphenylamino)acetoxy)-1-(2-oxo-2-phenylethyl)-1-azoniabicyclo[2.2.2]octane bromide (C45)

µl, 2.81 mmol) was added. The mixture was stirred at r.t. for 72 hours. The solvent was evaporated and the crude was used in the next step without any further purification.

Preparation of (R)-quinuclidin-3-yl 2-(benzo[b]thiophen-3-yl)-2-(2-ethylphenylamino)acetate (C44)

A mixture of 2-(benzo[b]thiophen-3-yl)-2-(2-ethylphenylamino)acetic acid (I43) (875 mg, 2.81 mmol), HOBT (430 mg, 2.81 mmol), and DCC (1.16 g, 5.62 mmol) in THF (28 ml) was stirred at r.t. for 30 minutes. Then (R)-quinuclidin-3-ol (715 mg, 5.62 mmol) was added, and the reaction mixture was stirred at r.t. overnight. The solvent was evaporated, and the crude product was partitioned between EtOAc and sat. $Na_2CO_3$. The organic phase was dried over sodium sulphate, filtered and evaporated to dryness. The crude was purified by flash chromatography (EtOAc/MeOH=3/1) to collect (R)-quinuclidin-3-yl 2-(benzo[b]thiophen-3-yl)-2-(2-ethylphenylamino)acetate (86 mg, 7.3% yield over two steps)

Scheme 29

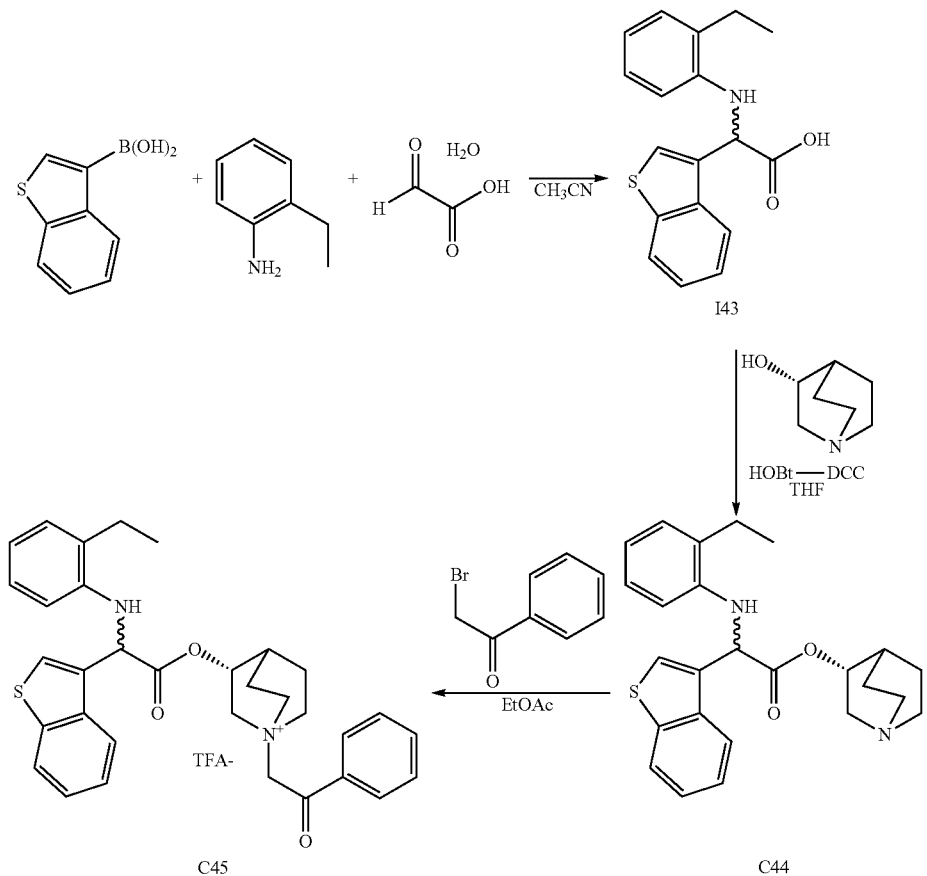

C45

C44

Preparation of 2-(benzo[b]thiophen-3-yl)-2-(2-ethylphenylamino)acetic acid (I43)

Benzo[b]thiophen-3-ylboronic acid (500 mg, 2.81 mmol) and 2-oxoacetic acid hydrate (259 mg, 2.81 mmol) were dissolved in acetonitrile (20 ml), and then 2-ethylaniline (346

Preparation of (3R)-3-(2-(benzo[b]thiophen-3-yl)-2-(2-ethylphenylamino)acetoxy)-1-(2-oxo-2-phenylethyl)-1-azoniabicyclo[2.2.2]octane bromide (C45)

A mixture of 2-bromo-1-phenylethanone (44.8 mg, 0.22 mmol) and (R)-quinuclidin-3-yl 2-(benzo[b]thiophen-3-yl)-

2-(2-ethylphenylamino)acetate (C44) (86 mg, 0.20 mmol) in EtOAc (3 ml) was heated under microwave irradiation at 100° C. for 1 hour. 2-Bromo-1-phenylethanone (44.8 mg, 0.22 mmol) was added, and the mixture was heated at 100° C. under microwave irradiation for an additional hour. The solvent was evaporated, and the crude product was triturated with Et$_2$O to collect (3R)-3-(2-(benzo[b]thiophen-3-yl)-2-(2-ethylphenylamino)acetoxy)-1-(2-oxo-2-phenylethyl)-1-azoniabicyclo[2.2.2]octane bromide (44.6 mg, 35.2% yield).

$^1$H NMR (300 MHz, DMSO-d$_6$) δ ppm 8.11-8.19 (m, 1H), 8.00-8.08 (m, 1H), 7.91-7.97 (m, 2H), 7.90 (s, 1H), 7.70-7.81 (m, 1H), 7.56-7.65 (m, 2H), 7.49 (td, 1H), 7.38-7.46 (m, 1H), 7.06 (dd, 1H), 6.99 (td, 1H), 6.65 (td, 1H), 6.59 (dd, 1H), 5.90 (d, 1H), 5.35 (d, 1H), 5.21-5.32 (m, 1H), 4.92-5.12 (m, 2H), 3.92-4.15 (m, 1H), 3.44-3.74 (m, 4H), 3.31-3.38 (m, 1H), 2.62 (q, 2H), 2.33-2.43 (m, 1H), 1.73-2.17 (m, 4H), 1.20 (t, 3H);

LC-MS (ESI POS): 539.20 (M+).

Example 29

Preparation of (3R)-3-(2-(benzo[b]thiophen-3-yl)-2-(3-methoxyphenylamino)acetoxy)-1-(2-oxo-2-phenylethyl)-1-azoniabicyclo[2.2.2]octane 2,2,2-trifluoroacetate (C48)

Preparation of 2-(benzo[b]thiophen-3-yl)-2-(3-methoxyphenylamino)acetic acid (I46)

A mixture of 3-methoxyaniline (400 mg, 3.25 mmol), benzo[b]thiophen-3-ylboronic acid (578 mg, 3.25 mmol), and 2-oxoacetic acid hydrate (299 mg, 3.25 mmol) in acetonitrile (30 ml) was stirred at room temperature overnight. The solvent was removed under vacuum and the crude was used us such in the next step.

Preparation of (R)-quinuclidin-3-yl 2-(benzo[b]thiophen-3-yl)-2-(3-methoxyphenylamino)acetate (C47)

A mixture of 2-(benzo[b]thiophen-3-yl)-2-(3-methoxyphenylamino)acetic acid (I46) (1.02 g, 3.25 mmol), (R)-quinuclidin-3-ol (496 mg, 3.90 mmol), DCC (805 mg, 3.90 mmol), and HOBT (597 mg, 3.90 mmol) in dry THF (30 ml) was stirred at r.t. overnight. THF was evaporated, and the crude product was taken up with EtOAc and washed twice with 1M K$_2$CO$_3$ and then with brine. The organic phase was dried over Na$_2$SO$_4$, filtered and evaporated to dryness. The crude product was purified by flash chromatography (DCM/MeOH=98/2 to 95/5) to obtain (R)-quinuclidin-3-yl 2-(benzo[b]thiophen-3-yl)-2-(3-methoxyphenylamino)acetate (213 mg, 15.5% yield over two steps).

Scheme 30

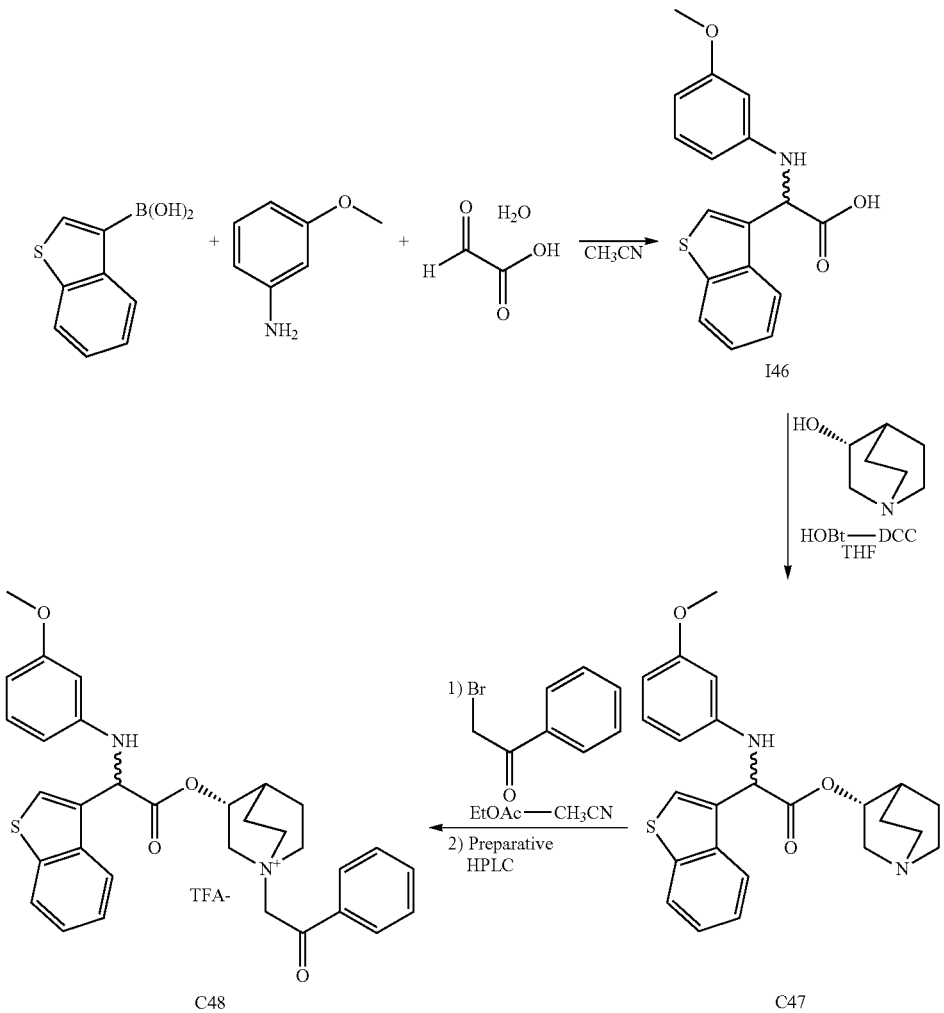

Preparation of (3R)-3-(2-(benzo[b]thiophen-3-yl)-2-(3-methoxyphenylamino)acetoxy)-1-(2-oxo-2-phenylethyl)-1-azoniabicyclo[2.2.2]octane 2,2,2-trifluoroacetate (C48)

(R)-quinuclidin-3-yl 2-(benzo[b]thiophen-3-yl)-2-(3-methoxyphenylamino)acetate (C47) (110 mg, 0.26 mmol) was dissolved in a mixture of ethyl acetate (2 ml) and acetonitrile (1 ml). 2-Bromo-1-phenylethanone (57.0 mg, 0.29 mmol) was added portion-wise, and the mixture was stirred at r.t. for three days. The solvent was removed in vacuo, and the residue was triturated with Et₂O. The product was purified by preparative HPLC to obtain (3R)-3-(2-(benzo[b]thiophen-3-yl)-2-(3-methoxyphenylamino)acetoxy)-1-(2-oxo-2-phenylethyl)-1-azoniabicyclo[2.2.2]octane 2,2,2-trifluoroacetate (50.28 mg, 29.5% yield).

$^1$H NMR (300 MHz, DMSO-$d_6$) δ ppm 8.07-8.21 (m, 1H), 7.84-8.07 (m, 4H), 7.69-7.81 (m, 1H), 7.56-7.69 (m, 2H), 7.46-7.52 (m, 1H), 7.36-7.46 (m, 1H), 7.02 (t, 1H), 6.49 (br. s., 1H), 6.33-6.45 (m, 2H), 6.15-6.27 (m, 1H), 5.80 and 5.83 (s, 1H), 5.20-5.37 (m, 1H), 5.06 and 5.14 (s, 2H), 3.72-4.21 (m, 2H), 3.65 and 3.66 (s, 3H), 3.27-3.63 (m, 4H), 2.06-2.15 and 2.32-0.42 (m, 1H), 1.32-2.06 (m, 4H);

LC-MS (ESI POS): 541.13 (M+).

Example 30

Preparation of (3R)-3-(2-(benzo[b]thiophen-3-yl)-2-(3-(ethoxycarbonyl)phenylamino)acetoxy)-1-(2-oxo-2-phenylethyl)-1-azoniabicyclo[2.2.2]octane 2,2,2-trifluoroacetate (C51)

Scheme 31

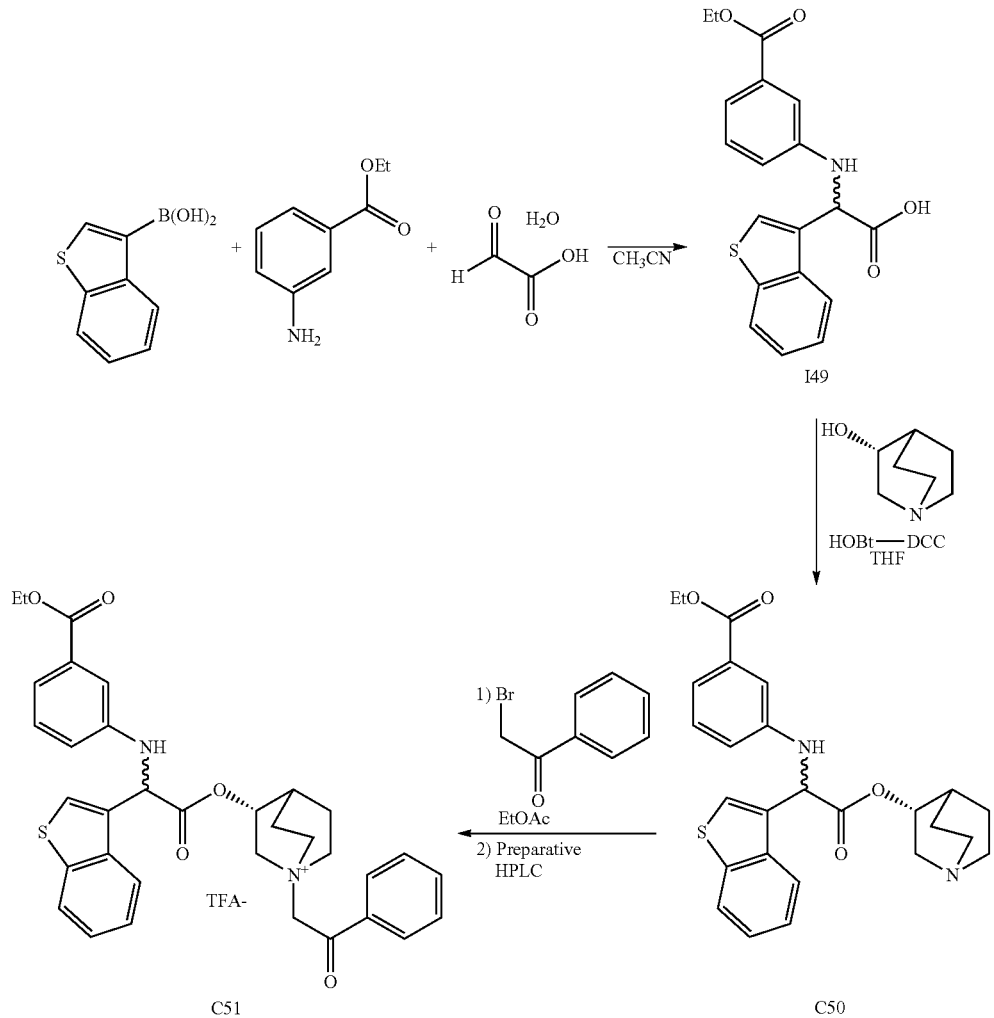

Preparation of 2-(benzo[b]thiophen-3-yl)-2-(3-(ethoxycarbonyl)phenylamino)acetic acid (I49)

To a solution of benzo[b]thiophen-3-ylboronic acid (500 mg, 2.81 mmol) and 2-oxoacetic acid hydrate (259 mg, 2.81 mmol) in acetonitrile (20 ml), was added ethyl 3-aminobenzoate (419 μl, 2.81 mmol). The reaction was stirred at r.t. for 72 hours, and then the solvent was evaporated under vacuum. The residue was used in the next step without any further purification.

Preparation of ethyl 3-(1-(benzo[b]thiophen-3-yl)-2-oxo-2-((R)-quinuclidin-3-yloxy)ethylamino)benzoate (C50)

2-(Benzo[b]thiophen-3-yl)-2-(3-(ethoxycarbonyl)phenylamino)acetic acid (I49) (998 mg, 2.81 mmol), HOBT (430 mg, 2.81 mmol), and DCC (1159 mg, 5.62 mmol) were dissolved in THF (28 ml). The mixture was stirred at r.t. for 30 minutes, and then (R)-quinuclidin-3-ol (714 mg, 5.62 mmol) was added. The resulting reaction mixture was stirred at r.t. overnight. The solvent was evaporated, and the crude product was partitioned between EtOAc and sat. Na$_2$CO$_3$. The organic phase was dried over sodium sulfate, filtered and evaporated to dryness. The crude product was purified by flash chromatography (DCM/MeOH=95/5) to collect ethyl 3-(1-(benzo[b]thiophen-3-yl)-2-oxo-2-((R)-quinuclidin-3-yloxy)ethylamino)benzoate (222 mg, 17.0% yield over two steps).

Preparation of (3R)-3-(2-(benzo[b]thiophen-3-yl)-2-(3-(ethoxycarbonyl)-phenylamino)acetoxy)-1-(2-oxo-2-phenylethyl)-1-azoniabicyclo[2.2.2]octane 2,2,2-trifluoroacetate (C51)

To a solution of ethyl 3-(1-(benzo[b]thiophen-3-yl)-2-oxo-2-((R)-quinuclidin-3-yloxy)ethylamino)benzoate (C50) (110 mg, 0.24 mmol) in ethyl acetate (2 ml), was added 2-bromo-1-phenylethanone (51.8 mg, 0.26 mmol), and the reaction was stirred at r.t. for three days. The solvent was removed in vacuo, and the crude product was triturated with Et$_2$O and then purified by preparative HPLC to obtain (3R)-3-(2-(benzo[b]thiophen-3-yl)-2-(3-(ethoxycarbonyl)phenylamino)acetoxy)-1-(2-oxo-2-phenylethyl)-1-azoniabicyclo[2.2.2]octane 2,2,2-trifluoroacetate (28.9 mg, 17.5% yield).

$^1$H NMR (300 MHz, DMSO-d$_6$) δ ppm 8.10-8.22 (m, 1H), 7.87-8.09 (m, 4H), 7.67-7.83 (m, 1H), 7.55-7.67 (m, 2H), 7.37-7.54 (m, 3H), 7.18-7.31 (m, 2H), 7.01-7.14 (m, 1H), 6.88 (br. s., 1H), 5.89 and 5.91 (s, 1H), 5.20-5.34 (m, 1H), 5.08 and 5.15 (s, 2H), 4.22 and 4.26 (q, 2H), 3.30-4.17 (m, 6H), 2.08-2.17 and 2.32-2.43 (m, 1H), 1.42-2.07 (m, 4H), 1.25 and 1.28 (t, 3H);

LC-MS (ESI POS): 583.21 (M+).

Example 31

Preparation of (R)-3-(2-(6-(benzyloxy)pyridin-3-yl)-2-(phenylamino)acetoxy)-1-(2-oxo-2-phenylethyl)-1-azoniabicyclo[2.2.2]octane 2,2,2-trifluoroacetate (Diastereomer 1 of C54)

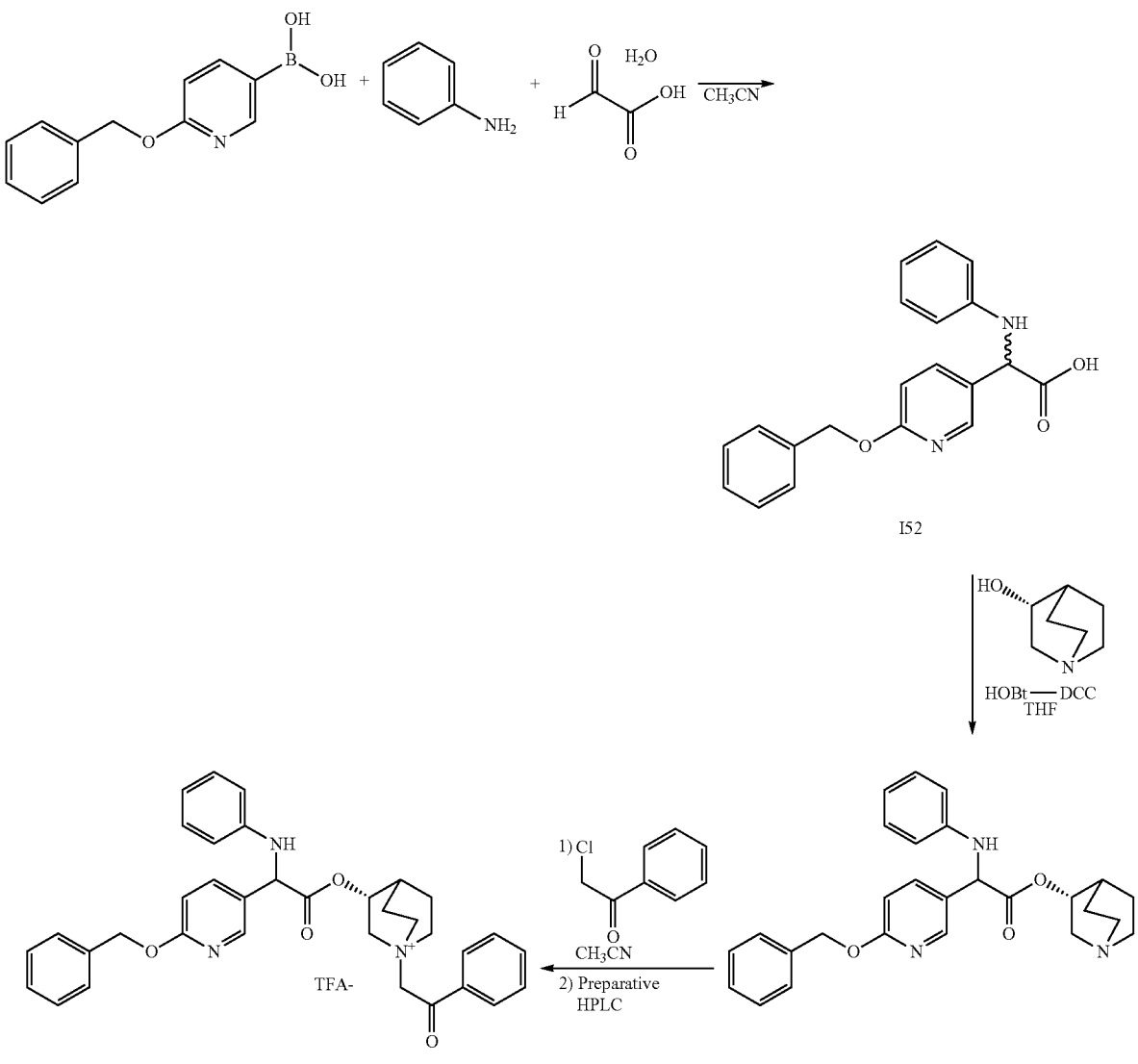

Scheme 32

Diastereomer 1 of C54

Preparation of 2-(6-(benzyloxy)pyridin-3-yl)-2-(phenylamino)acetic acid (I52)

To a suspension of 2-oxoacetic acid hydrate (0.40 g, 4.37 mmol) and aniline (0.40 ml, 4.37 mmol) in acetonitrile (25 ml), was added 6-(benzyloxy)pyridin-3-ylboronic acid (1.00 g, 4.37 mmol), and the reaction mixture was refluxed for 2 hours. The solvent was evaporated, and the resulting dark brown oil was purified by flash chromatography (DCM/MeOH=97/3) to obtain 2-(6-(benzyloxy)pyridin-3-yl)-2-(phenylamino)acetic acid (460 mg, 31.5% yield).

Preparation of (R)-quinuclidin-3-yl 2-(6-(benzyloxy) pyridin-3-yl)-2-(phenylamino)acetate (Diastereomer 1 and 2 of C53)

To a solution of 2-(6-(benzyloxy)pyridin-3-yl)-2-(phenylamino)acetic acid (I52) (460 mg, 1.38 mmol) in THF (20 ml), were added DCC (341 mg, 1.65 mmol), 1H-benzo[d][1,2,3]triazol-1-ol (223 mg, 1.65 mmol), and (R)-quinuclidin-3-ol (210 mg, 1.65 mmol). The resulting reaction mixture was stirred at room temperature for 15 hours, and then the solvent was evaporated. DCM is added, the insoluble was filtered off and the organic phase was washed twice with $Na_2CO_3$ and brine, dried over $Na_2SO_4$ and evaporated. The crude product was purified by flash chromatography (DCM/MeOH=95/5 to 97/3), recovering first diastereomer 1 of C53 (71 mg, 12% yield), then a mixture of diastereomers of C53 (84 mg, 14% yield) and finally diastereomer 2 of C53 (21 mg, 4% yield).

Preparation of (R)-3-(2-(6-(benzyloxy)pyridin-3-yl)-2-(phenylamino)acetoxy)-1-(2-oxo-2-phenylethyl)-1-azoniabicyclo[2.2.2]octane 2,2,2-trifluoroacetate (Diastereomer 1 of C54)

2-Chloro-1-phenylethanone (24.7 mg, 0.16 mmol) was added to a solution of (R)-quinuclidin-3-yl 2-(6-(benzyloxy)pyridin-3-yl)-2-(phenylamino)acetate (diastereomer 1 of C53) (71.0 mg, 0.16 mmol) in EtOAc (4 ml). The reaction was stirred at room temperature overnight. The solvent was evaporated, and the crude product was purified by preparative HPLC to obtain (R)-3-(2-(6-(benzyloxy)pyridin-3-yl)-2-(phenylamino)acetoxy)-1-(2-oxo-2-phenylethyl)-1-azoniabicyclo[2.2.2]octane 2,2,2-trifluoroacetate (43.1 mg, 40% yield).

$^1$H NMR (300 MHz, DMSO-$d_6$) ppm 8.38 (d, 1H) 7.85-8.06 (m, 3H) 7.75 (t, 1H) 7.59 (t, 2H) 7.29-7.49 (m, 5H) 7.11 (dd, 2H) 6.95 (d, 1H) 6.75 (d, 2H) 6.62 (t, 1H) 5.44 (s, 1H) 5.36 (s, 2H) 5.19-5.29 (m, 1H) 5.11 (s, 2H) 4.06 (m, 1H) 3.30-3.78 (m, 5H) 2.33-2.44 (m, 1H) 1.79-2.18 (m, 4H);

LC-MS (ESI POS): 562.26 (M+).

Example 32

Preparation of (3R)-3-(2-(6-hydroxypyridin-3-yl)-2-(phenylamino)acetoxy)-1-(2-oxo-2-phenylethyl)-1-azoniabicyclo[2.2.2]octane 2,2,2-trifluoroacetate (C55)

Scheme 33

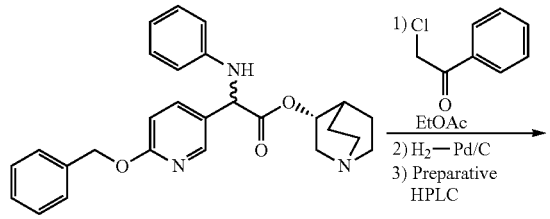

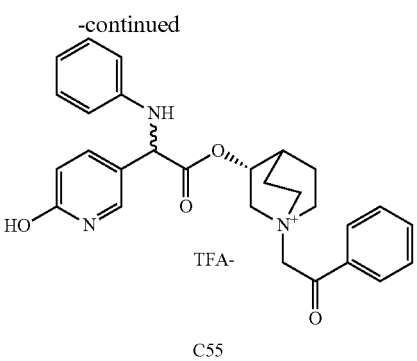

C55

2-Chloro-1-phenylethanone (29.3 mg, 0.12 mmol) was added to a solution of (R)-quinuclidin-3-yl 2-(6-(benzyloxy)pyridin-3-yl)-2-(phenylamino)acetate (C53) (84 mg, 0.19 mmol, mixture of diastereomers) in EtOAc (4 ml). The reaction was stirred at room temperature overnight, and then a catalytic amount of 10% Pd/C (about 10 mg) and 37% HCl (0.50 ml) were added, and the reaction was hydrogenated at 20 psi for 2 hours. Pd/C is removed by filtration, and the clear solution was evaporated to dryness. The crude was purified by preparative HPLC to obtain (3R)-3-(2-(6-hydroxypyridin-3-yl)-2-(phenylamino)acetoxy)-1-(2-oxo-2-phenylethyl)-1-azoniabicyclo[2.2.2]octane chloride (20.3 mg, 18% yield).

$^1$H NMR (300 MHz, DMSO-$d_6$) ppm 11.25-11.95 (m, 1H) 7.91-8.08 (m, 2H) 7.71-7.85 (m, 1H) 7.52-7.71 (m, 5H) 7.12 (dd, 2H) 6.72 (d, 2H) 6.63 (t, 1H) 6.38 (d, 1H) 5.20-5.28 (m, 1H) 5.18 (d, 3H) 4.06-4.18 (m, 1H) 3.48-3.82 (m, 5H) 2.18-2.26 (m, 1H) 1.75-2.10 (m, 4H);

LC-MS (ESI POS): 472.16 (M+).

Example 33

Preparation of (R)-3-(2-(6-(benzyloxy)pyridin-3-yl)-2-(phenylamino)acetoxy)-1-(2-oxo-2-phenylethyl)-1-azoniabicyclo[2.2.2]octane 2,2,2-trifluoroacetate (C54)

Scheme 34

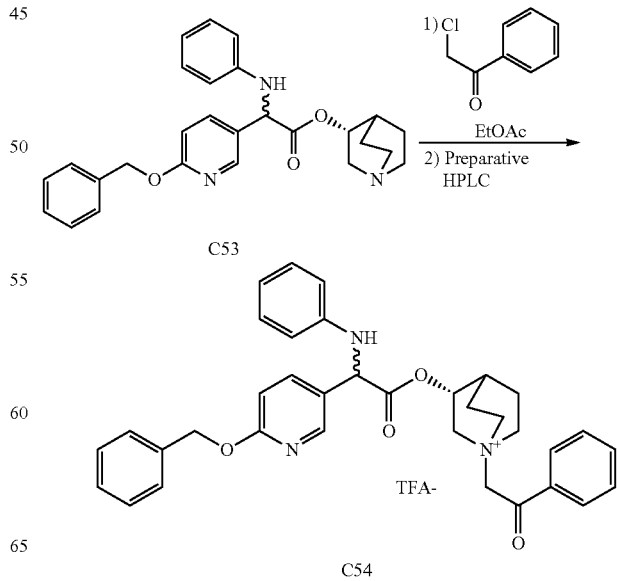

2-Chloro-1-phenylethanone (8 mg, 0.05 mmol) was added to a solution of (R)-quinuclidin-3-yl 2-(6-(benzyloxy)pyridin-3-yl)-2-(phenylamino)acetate (C53) (22 mg, 0.05 mmol) in EtOAc (2 ml). The reaction mixture was stirred at room temperature overnight. The solvent was evaporated, and the crude product was purified by preparative HPLC to obtain (R)-3-(2-(6-(benzyloxy)pyridin-3-yl)-2-(phenylamino)acetoxy)-1-(2-oxo-2-phenylethyl)-1-azoniabicyclo[2.2.2]octane 2,2,2-trifluoroacetate (14.5 mg, 43% yield).

$^1$H NMR (300 MHz, DMSO-$d_6$) ppm 8.38 (d, 1H) 7.85-8.11 (m, 3H) 7.77 (t, 1H) 7.62 (t, 2H) 7.21-7.51 (m, 5H) 7.11 (dd, 2H) 6.93 (d, 1H) 6.74 (d, 2H) 6.62 (t, 1H) 6.40 (s, 1H) 5.40 (s, 1H) 5.36 (s, 2H) 5.24 (s, 1H) 5.17 (s, 2H) 4.12 (dd, 1H) 3.76-3.88 (m, 5H) 2.09-2.22 (m, 1H) 1.91-2.08 (m, 2H) 1.73-1.89 (m, 1H) 1.53-1.73 (m, 1H);
LC-MS (ESI POS): 562.21 (M+).

Example 34

Preparation of (3R)-3-(2-(4-methoxyphenylamino)-2-(thiophen-3-yl)acetoxy)-1-(2-oxo-2-phenylethyl)-1-azoniabicyclo[2.2.2]octane 2,2,2-trifluoroacetate (C58)

Preparation of 2-(4-methoxyphenylamino)-2-(thiophen-3-yl)acetic acid (I56)

A mixture of thiophen-3-ylboronic acid (339 mg, 2.65 mmol), 2-oxoacetic acid hydrate (244 mg, 2.65 mmol), and 4-methoxyaniline (326 mg, 2.65 mmol) was heated under microwave irradiation at 100° C. for 1 hour. The precipitate was recovered and washed sequentially with acetonitrile, DCM and Et$_2$O. The compound was dried under vacuum at 40° C. to obtain 2-(4-methoxyphenylamino)-2-(thiophen-3-yl)acetic acid (540 mg, 77% yield).

Preparation of (R)-quinuclidin-3-yl 2-(4-methoxyphenylamino)-2-(thiophen-3-yl)acetate (C57)

A mixture of 2-(4-methoxyphenylamino)-2-(thiophen-3-yl)acetic acid (I56) (544 mg, 2.01 mmol), (R)-quinuclidin-3-ol (614 mg, 4.83 mmol), DCC (511 mg, 2.47 mmol), and HOBT (380 mg, 2.48 mmol) in dry THF (160 ml) was stirred at room temperature overnight. The solvent was evaporated, Scheme 35

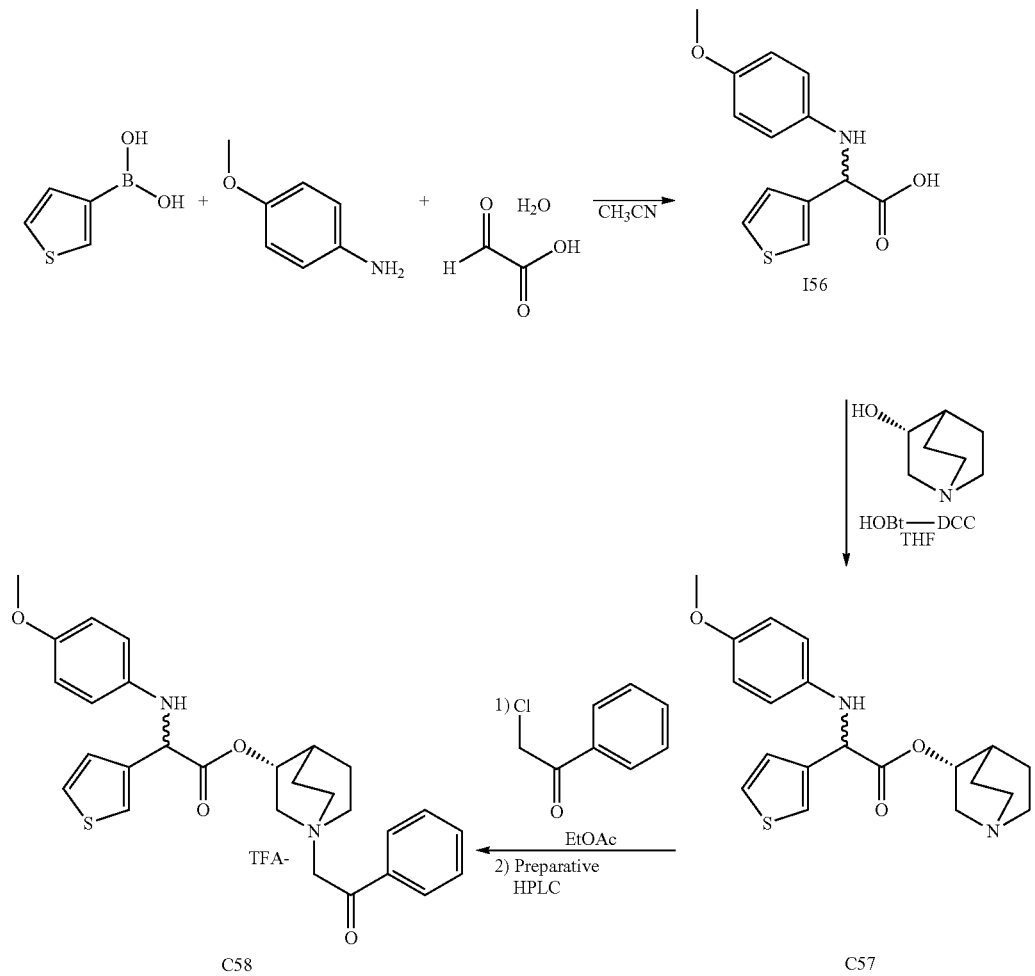

and the residue was partitioned between EtOAc and 2M NaHCO$_3$. The organic phase was further washed with 2M NaHCO$_3$ and brine, dried over Na$_2$SO$_4$ and evaporated. The residue was purified by flash chromatography (DCM/MeOH=95/5 to 7/3) to obtain (R)-quinuclidin-3-yl 2-(4-methoxyphenylamino)-2-(thiophen-3-yl)acetate (40 mg, 5% yield).

Preparation of (3R)-3-(2-(4-methoxyphenylamino)-2-(thiophen-3-yl)acetoxy)-1-(2-oxo-2-phenylethyl)-1-azoniabicyclo[2.2.2]octane 2,2,2-trifluoroacetate (C58)

A mixture of (R)-quinuclidin-3-yl 2-(4-methoxyphenylamino)-2-(thiophen-3-yl)acetate (C57) (40 mg, 0.11 mmol) and 2-chloro-1-phenylethanone (16.6 mg, 0.11 mmol) in EtOAc (5 ml) was stirred at room temperature overnight. The solvent was evaporated, and the residue was purified by preparative HPLC to obtain (3R)-3-(2-(4-methoxyphenylamino)-2-(thiophen-3-yl)acetoxy)-1-(2-oxo-2-phenylethyl)-1-azoniabicyclo[2.2.2]octane 2,2,2-trifluoroacetate (33 mg, 51% yield).

$^1$H NMR (300 MHz, DMSO-d$_6$) ppm 7.90-8.06 (m, 2H) 7.71-7.84 (m, 1H) 7.52-7.70 (m, 4H) 7.28 (dd, 1H) 6.65-6.81 (m, 4H) 5.40 (d, 1H) 5.05-5.30 (m, 3H) 4.02-4.18 (m, 1H) 3.62 (s, 3H) 3.39-3.70 (m, 5H) 2.35 (d, 1H) 1.50-2.14 (m, 4H);

LC-MS (ESI POS): 562.21 (M+).

Example 35

Preparation of (R)-3-(2-(2-(methoxycarbonyl)thiophen-3-ylamino)-2-(6-methoxypyridin-3-yl)acetoxy)-1-(2-oxo-2-phenylethyl)-1-azoniabicyclo[2.2.2]octane 2,2,2-trifluoroacetate (Diastereomer 1 of C61)

Scheme 36

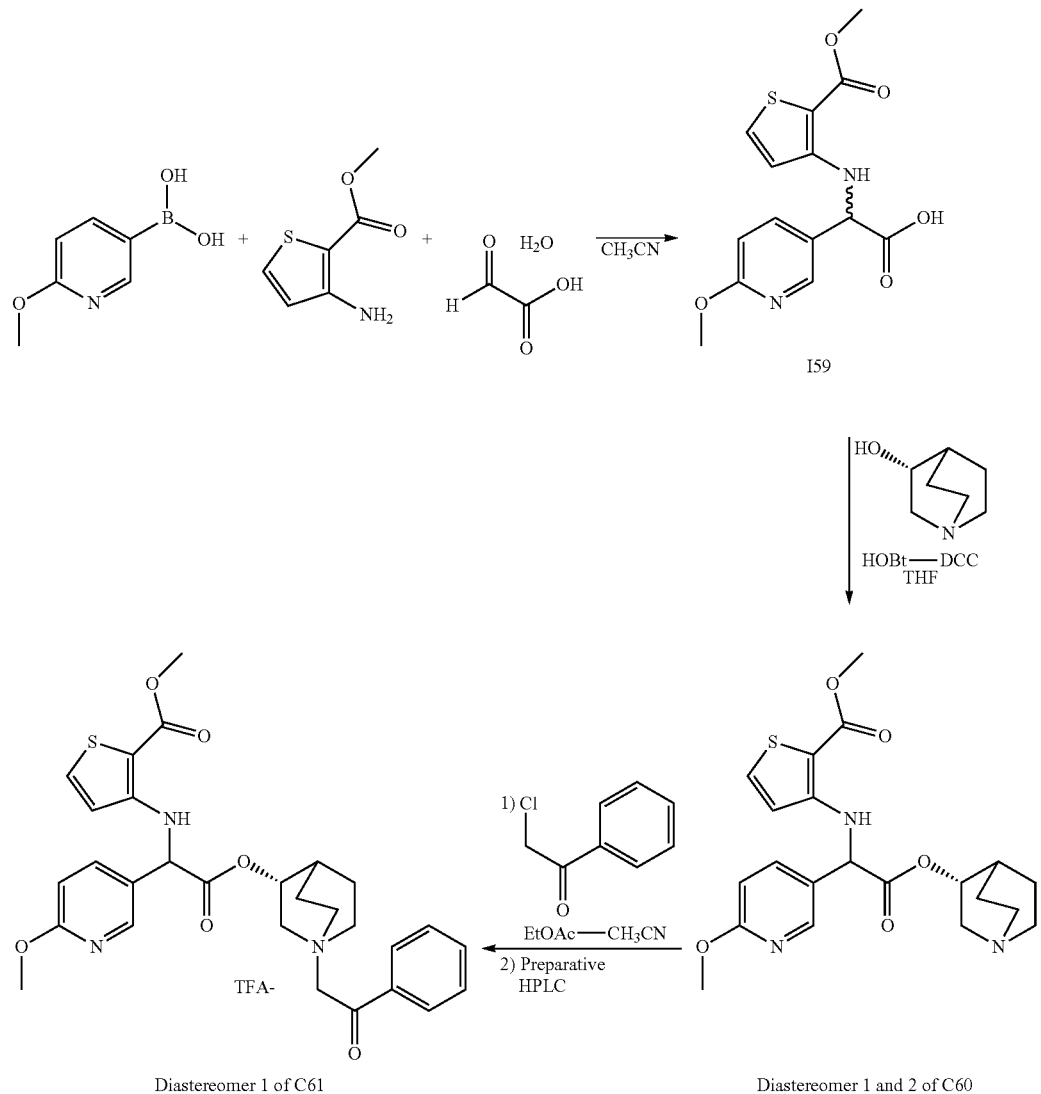

Diastereomer 1 of C61

Diastereomer 1 and 2 of C60

Preparation of 2-(2-(methoxycarbonyl)thiophen-3-ylamino)-2-(6-methoxypyridin-3-yl)acetic acid (I159)

To a suspension of 2-oxoacetic acid hydrate (156 mg, 1.70 mmol) and methyl 3-aminothiophene-2-carboxylate (267 mg, 1.70 mmol) in acetonitrile (15 ml), was added 6-methoxypyridin-3-ylboronic acid (260 mg, 1.70 mmol). The reaction mixture was refluxed for 2 hours and the solvent was evaporated to obtain 2-(2-(methoxycarbonyl)thiophen-3-ylamino)-2-(6-methoxypyridin-3-yl)acetic acid (548 mg, 100% yield). The product was used in the next step without any further purification.

Preparation of (R)-methyl 3-(1-(6-methoxypyridin-3-yl)-2-oxo-2-(quinuclidin-3-yloxy)ethylamino)thiophene-2-carboxylate (Diastereomer 1 and 2 of C60)

To a solution of 2-(2-(methoxycarbonyl)thiophen-3-ylamino)-2-(6-methoxypyridin-3-yl)acetic acid (I59) (548 mg, 1.70 mmol) in THF (20 ml), were added N,N'-methanediylidenedicyclohexanamine (421 mg, 2.04 mmol), 1H-benzo[d][1,2,3]triazol-1-ol (276 mg, 2.04 mmol), and (R)-quinuclidin-3-ol (259 mg, 2.04 mmol). The reaction mixture was stirred at room temperature for 15 hours, and then the solvent was evaporated. The residue was taken up with DCM, and the insoluble was removed by filtration. The organic phase was washed twice with Na$_2$CO$_3$ and then brine, dried over Na$_2$SO$_4$, filtered and evaporated. The crude product was purified by flash chromatography (DCM/MeOH=95/5) collecting first diastereomer 1 of C60 (140 mg, 19 yield) and then a mixture of diastereomers 1 and 2 of C60 (100 mg, 14% yield).

Preparation of (R)-3-(2-(2-(methoxycarbonyl)thiophen-3-ylamino)-2-(6-methoxypyridin-3-yl)acetoxy)-1-(2-oxo-2-phenylethyl)-1-azoniabicyclo[2.2.2]octane 2,2,2-trifluoroacetate (Diastereomer 1 of C61)

To a solution of (R)-methyl 3-(1-(6-methoxypyridin-3-yl)-2-oxo-2-(quinuclidin-3-yloxy)ethylamino)thiophene-2-carboxylate (diastereomer 1 of C60) (60 mg, 0.14 mmol) in EtOAc (3 ml) and acetonitrile (3 ml), was added 2-chloro-1-phenylethanone (23.6 mg, 0.15 mmol), and the reaction was stirred at room temperature for 15 hours. Then the solvent was evaporated, and the crude product was purified by preparative HPLC to obtain (R)-3-(2-(2-(methoxycarbonyl)thiophen-3-ylamino)-2-(6-methoxypyridin-3-yl)acetoxy)-1-(2-oxo-2-phenylethyl)-1-azoniabicyclo[2.2.2]octane 2,2,2-trifluoroacetate (48 mg, 52% yield).

$^1$H NMR (300 MHz, DMSO-d$_6$) ppm 8.33 (d, 1H) 7.89-8.05 (m, 2H) 7.52-7.83 (m, 6H) 6.88 (d, 1H) 6.77 (d, 1H) 5.72-5.81 (m, 1H) 5.22-5.36 (m, 1H) 5.13 (s, 2H) 3.97-4.17 (m, 1H) 3.85 (s, 3H) 3.78 (s, 3H) 3.36-3.75 (m, 5H) 2.40-2.47 (m, 1H) 1.83-2.21 (m, 4H);

LC-MS (ESI POS): 550.18 (M+).

Example 36

Preparation of (R)-3-(2-(2-(methoxycarbonyl)thiophen-3-ylamino)-2-(6-methoxypyridin-3-yl)acetoxy)-1-(2-oxo-2-(thiazol-2-yl)ethyl)-1-azoniabicyclo[2.2.2]octane 2,2,2-trifluoroacetate (Diastereomer 1 of C62)

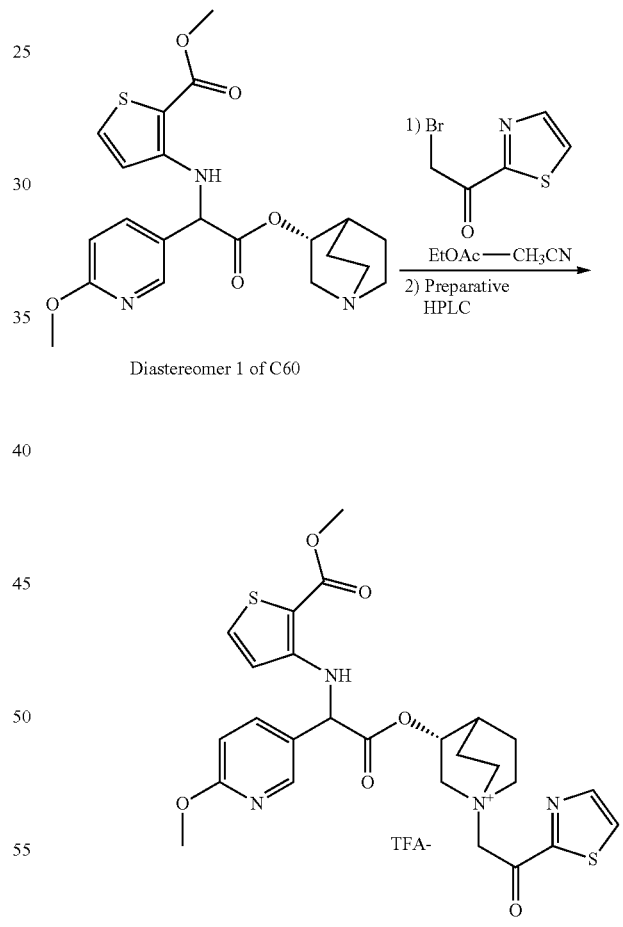

Scheme 37

Diastereomer 1 of C60

Diastereomer 1 of C62

To a solution of (R)-methyl 3-(1-(6-methoxypyridin-3-yl)-2-oxo-2-(quinuclidin-3-yloxy)ethylamino)thiophene-2-carboxylate (diastereomer 1 of C60) (60 mg, 0.14 mmol) in EtOAc (3 ml) and acetonitrile (3 ml), was added 2-bromo-1-(thiazol-2-yl)ethanone (31.5 mg, 0.15 mmol), and the reaction mixture was stirred at room temperature for 15 hours.

The solvent was evaporated, and the crude product was purified by preparative HPLC to obtain (R)-3-(2-(2-(methoxycarbonyl)thiophen-3-ylamino)-2-(6-methoxypyridin-3-yl)acetoxy)-1-(2-oxo-2-(thiazol-2-yl)ethyl)-1-azoniabicyclo[2.2.2]octane 2,2,2-trifluoroacetate (47 mg, 50% yield).

$^1$H NMR (300 MHz, DMSO-$d_6$) ppm 8.38 (d, 1H) 8.32 (d, 1H) 8.23 (d, 1H) 7.63-7.82 (m, 3H) 6.87 (d, 1H) 6.76 (d, 1H) 5.65-5.79 (m, 1H) 5.23-5.33 (m, 1H) 5.16 (s, 2H) 4.04-4.17 (m, 1H) 3.86 (s, 3H) 3.78 (s, 3H) 3.37-3.75 (m, 5H) 2.39-2.47 (m, 1H) 1.85-2.17 (m, 4H);

LC-MS (ESI POS): 557.09 (M+).

Example 37

Preparation of (3R)-3-(2-(2-(methoxycarbonyl)thiophen-3-ylamino)-2-(6-methoxypyridin-3-yl)acetoxy)-1-(2-oxo-2-(thiophen-2-yl)ethyl)-1-azoniabicyclo[2.2.2]octane 2,2,2-trifluoroacetate (C63)

Scheme 38

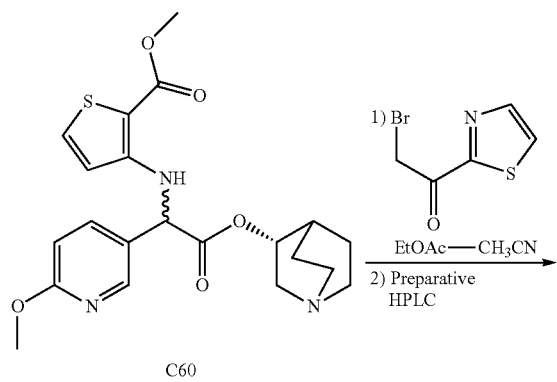

C60

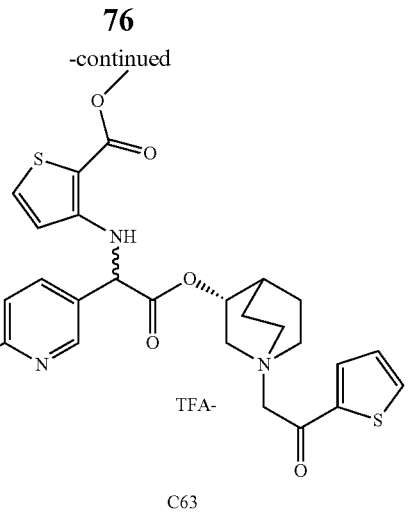

C63

To a solution of methyl 3-(1-(6-methoxypyridin-3-yl)-2-oxo-2-((R)-quinuclidin-3-yloxy)ethylamino)thiophene-2-carboxylate (C60) (60 mg, 0.14 mmol) in EtOAc (3 ml) and acetonitrile (3 ml), is added 2-bromo-1-(thiophen-2-yl)ethanone (31.4 mg, 0.15 mmol), and the reaction was stirred at room temperature for 15 hours. The solvent was evaporated, and the crude product was purified by preparative HPLC to obtain (3R)-3-(2-(2-(methoxycarbonyl)thiophen-3-ylamino)-2-(6-methoxypyridin-3-yl)acetoxy)-1-(2-oxo-2-(thiophen-2-yl)ethyl)-1-azoniabicyclo[2.2.2]octane 2,2,2-trifluoroacetate (57 mg, 61% yield).

$^1$H NMR (300 MHz, DMSO-d6) ppm 8.27-8.38 (m, 1H) 8.15-8.27 (m, 1H) 7.96-8.12 (m, 1H) 7.61-7.86 (m, 3H) 7.24-7.41 (m, 1H) 6.86 (d, 1H) 6.76 (dd, 1H) 5.70 (d, 1H) 5.14-5.36 (m, 1H) 4.87-5.12 (m, 2H) 4.00 (br. s., 1H) 3.85 (s, 3H) 3.78 (s, 3H) 3.37-3.75 (m, 5H) 2.37-2.46 (m, 1H) 1.57-2.14 (m, 4H)

LC-MS (ESI POS): 556.12 (M+).

Example 38

Preparation of (3R)-3-(2-(3-(ethoxycarbonyl)phenylamino)-2-(6-methoxypyridin-3-yl)acetoxy)-1-(2-oxo-2-phenylethyl)-1-azoniabicyclo[2.2.2]octane chloride (C66)

Scheme 39

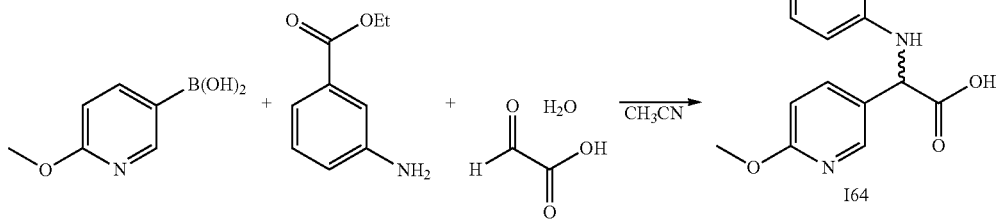

I64

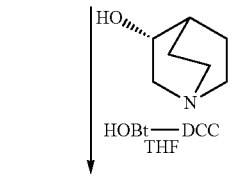

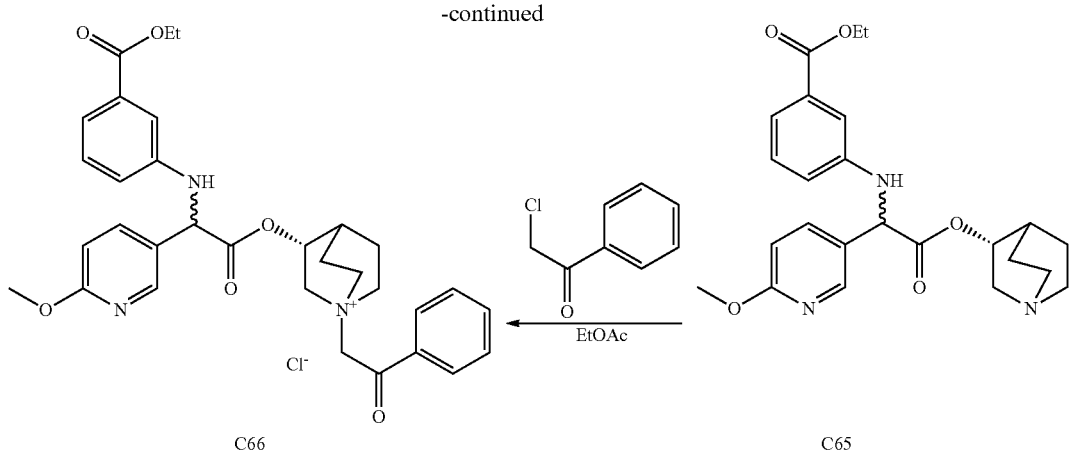

Preparation of 2-(3-(ethoxycarbonyl)phenylamino)-2-(6-methoxypyridin-3-yl)acetic acid (I64)

A mixture of 6-methoxypyridin-3-ylboronic acid (1.2 g, 7.84 mmol), ethyl 3-aminobenzoate (1.29 g, 7.84 mmol), and 2-oxoacetic acid hydrate (723 mg, 7.84 mmol) in acetonitrile (70 ml) was stirred at room temperature overnight. The solvent was evaporated under vacuum, and the crude product was purified by flash chromatography (DCM/MeOH=9/1) to obtain 2-(3-(ethoxycarbonyl)phenylamino)-2-(6-methoxypyridin-3-yl)acetic acid (0.95 g, 38% yield).

Preparation of ethyl 3-(1-(6-methoxypyridin-3-yl)-2-oxo-2-((R)-quinuclidin-3-yloxy)ethylamino)benzoate (C65)

A mixture of 2-(3-(ethoxycarbonyl)phenylamino)-2-(6-methoxypyridin-3-yl)acetic acid (I64) (951 mg, 2.51 mmol), (R)-quinuclidin-3-ol (694 mg, 5.47 mmol), HOBT (837 mg, 5.47 mmol), and DCC (1.13 g, 5.47 mmol) in dry THF (35 ml) was stirred at room temperature overnight. The solvent was evaporated, and the crude product was partitioned between DCM and 2M $K_2CO_3$. The organic phase was dried over $Na_2SO_4$, filtered and evaporated to dryness. The crude product was purified by flash chromatography (DMC/MeOH=97/3 to 95/5) to obtain ethyl 3-(1-(6-methoxypyridin-3-yl)-2-oxo-2-((R)-quinuclidin-3-yloxy)ethylamino)benzoate (348 mg, 27.5% yield).

Preparation of (3R)-3-(2-(3-(ethoxycarbonyl)phenylamino)-2-(6-methoxypyridin-3-yl)acetoxy)-1-(2-oxo-2-phenylethyl)-1-azoniabicyclo[2.2.2]octane chloride (C66)

2-Chloro-1-phenylethanone (17.6 mg, 0.11 mmol) was added to a solution of ethyl 3-(1-(6-methoxypyridin-3-yl)-2-oxo-2-((R)-quinuclidin-3-yloxy)ethylamino)benzoate (C65) (50 mg, 0.11 mmol) in EtOAc (2 ml). The reaction mixture was stirred at room temperature overnight, and then the solvent was evaporated to dryness. The residue was triturated with $Et_2O$ and then purified by preparative HPLC (Eluent: $CH_3CN/H_2O$) to obtain (3R)-3-(2-(3-(ethoxycarbonyl)phenylamino)-2-(6-methoxypyridin-3-yl)acetoxy)-1-(2-oxo-2-phenylethyl)-1-azoniabicyclo[2.2.2]octane chloride (26.3 mg, 38.9% yield).

$^1$H NMR (300 MHz, DMSO-$d_6$) δ ppm 8.38 (t, 1H), 7.85-8.04 (m, 3H), 7.71-7.82 (m, 1H), 7.55-7.69 (m, 2H), 7.37 (br. s., 1H), 7.17-7.28 (m, 2H), 7.01 (dt, 1H), 6.88 (dd, 1H), 6.80 and 6.85 (d, 1H), 5.48 and 5.51 (d, 1H), 5.21-5.30 (m, 1H), 5.17 and 5.22 (br. s., 2H), 4.20-4.36 (m, 2H), 3.97-4.24 (m, 1H), 3.86 (s, 3H), 3.44-3.80 (m, 5H), 2.16-2.24 and 2.34-2.41 (m, 1H), 1.56-2.15 (m, 4H), 1.27 and 1.30 (t, 3H);
LC-MS (ESI POS): 558.46 (M+).

Example 39

Preparation of (3R)-3-(2-(3-(ethoxycarbonyl)phenylamino)-2-(6-methoxypyridin-3-yl)acetoxy)-1-(2-oxo-2-(thiophen-2-yl)ethyl)-1-azoniabicyclo[2.2.2]octane chloride (C67)

Scheme 40

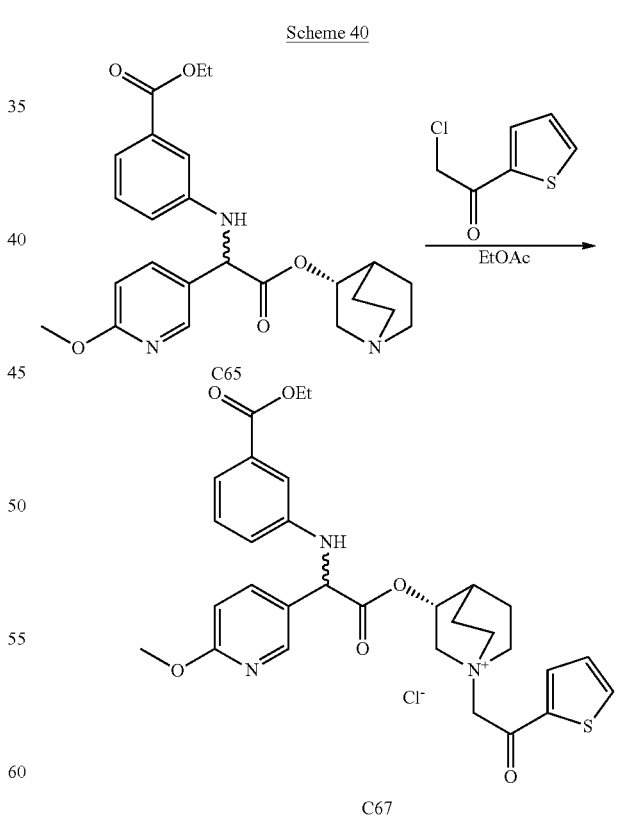

2-Chloro-1-(thiophen-2-yl)ethanone (18.3 mg, 0.11 mmol) was added to a solution of ethyl 3-(1-(6-methoxypyridin-3-yl)-2-oxo-2-((R)-quinuclidin-3-yloxy)ethylamino)benzoate (C65) (50 mg, 0.11 mmol) in EtOAc (2 ml). The reaction was stirred at room temperature overnight. The solvent was evaporated, and the residue was triturated with Et$_2$O, filtered and dried. The product was purified by flash-chromatography (DCM/MeOH=97/3 to 9/1) to obtain (3R)-3-(2-(3-(ethoxycarbonyl)phenylamino)-2-(6-methoxypyridin-3-yl)acetoxy)-1-(2-oxo-2-(thiophen-2-yl)ethyl)-1-azoniabicyclo[2.2.2]octane chloride (41.6 mg, 60.9% yield).

$^1$H NMR (300 MHz, DMSO-d$_6$) δ ppm 8.37 (t, 1H), 8.19-8.25 (m, 1H), 8.04-8.12 (m, 1H), 7.86-7.93 (m, 1H), 7.30-7.41 (m, 2H), 7.17-7.29 (m, 2H), 6.96-7.05 (m, 1H), 6.87 (d, 1H), 6.79 and 6.84 (d, 1H), 5.46 and 5.49 (d, 1H), 5.16-5.28 (m, 1H), 5.04 and 5.08 (s, 2H), 4.21-4.37 (m, 2H), 3.97-4.19 (m, 1H), 3.85 and 3.86 (s, 3H), 3.46-3.83 (m, 5H), 2.13-2.24 and 2.31-2.41 (m, 1H), 1.58-2.14 (m, 4H), 1.29 and 1.30 (t, 3H);

LC-MS (ESI POS): 564.39 (M+).

Example 40

Preparation of (3R)-3-(2-(3-(ethoxycarbonyl)phenylamino)-2-(6-methoxypyridin-3-yl)acetoxy)-1-(2-(4-hydroxyphenyl)-2-oxoethyl)-1-azoniabicyclo[2.2.2]octane bromide (C68)

Scheme 41

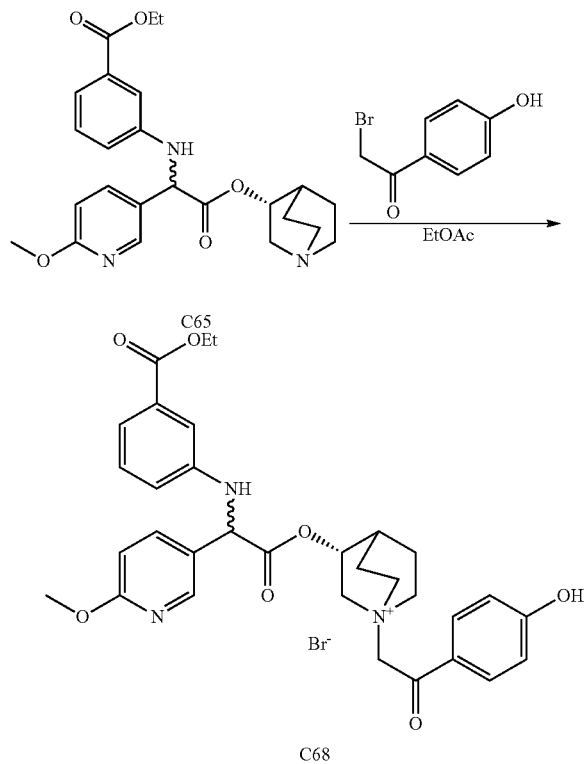

2-Bromo-1-(4-hydroxyphenyl)ethanone (24.5 mg, 0.11 mmol) was added to a solution of ethyl 3-(1-(6-methoxypyridin-3-yl)-2-oxo-2-((R)-quinuclidin-3-yloxy)ethylamino)benzoate (C65) (50 mg, 0.11 mmol) in EtOAc (2 ml). The reaction was stirred at room temperature overnight. The solvent was evaporated, and the residue was triturated with Et$_2$O, filtered and dried. The product was purified by flash-chromatography (DCM/MeOH=97/3 to 9/1) to obtain (3R)-3-(2-(3-(ethoxycarbonyl)phenylamino)-2-(6-methoxypyridin-3-yl)acetoxy)-1-(2-(4-hydroxyphenyl)-2-oxoethyl)-1-azoniabicyclo[2.2.2]octane bromide (37.3 mg, 50.1% yield).

$^1$H NMR (300 MHz, DMSO-d$_6$) δ ppm 10.74 (br. s., 1H), 8.38 (t, 1H), 7.78-7.95 (m, 3H), 7.36 (s, 1H), 7.18-7.30 (m, 2H), 6.96-7.06 (m, 1H), 6.84-6.96 (m, 3H), 6.77 and 6.80 (d, 1H), 5.46 and 5.49 (d, 1H), 5.15-5.30 (m, 1H), 5.01 and 5.06 (s, 2H), 4.24 and 4.27 (q, 2H), 4.00-4.18 (m, 1H), 3.85 and 3.86 (s, 3H), 3.44-3.81 (m, 5H), 2.13-2.23 and 2.32-2.41 (m, 1H), 1.60-2.13 (m, 4H), 1.28 and 1.30 (t, 3H);

LC-MS (ESI POS): 574.43 (M+).

Example 41

Preparation of (3R)-3-(2-(3-(ethoxycarbonyl)phenylamino)-2-(6-methoxypyridin-3-yl)acetoxy)-1-(2-oxo-2-(thiazol-2-yl)ethyl)-1-azoniabicyclo[2.2.2]octane bromide (C69)

Scheme 42

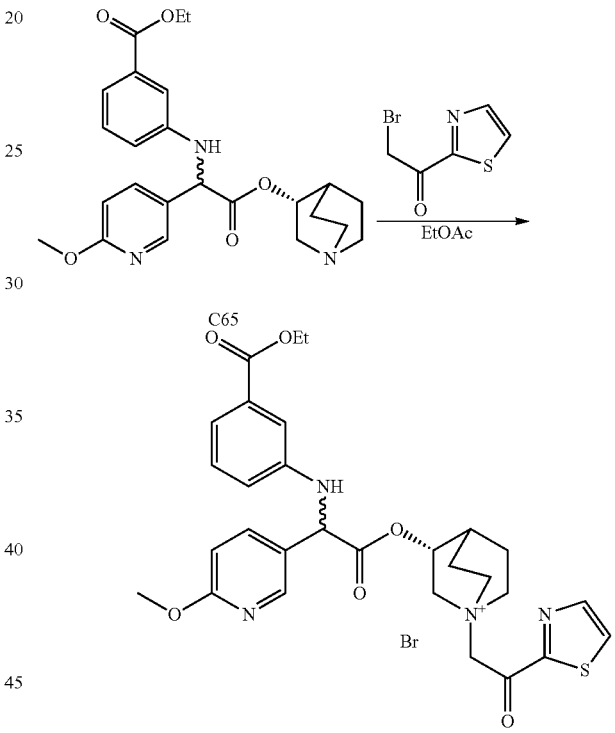

2-Bromo-1-(thiazol-2-yl)ethanone (23.4 mg, 0.11 mmol) was added to a solution of ethyl 3-(1-(6-methoxypyridin-3-yl)-2-oxo-2-((R)-quinuclidin-3-yloxy)ethylamino)benzoate (C65) (50 mg, 0.11 mmol) in EtOAc (2 ml). The reaction was stirred at room temperature overnight, and then the solvent was evaporated and the residue was triturated with Et$_2$O, filtered and dried to obtain (3R)-3-(2-(3-(ethoxycarbonyl)phenylamino)-2-(6-methoxypyridin-3-yl)acetoxy)-1-(2-oxo-2-(thiazol-2-yl)ethyl)-1-azoniabicyclo[2.2.2]octane bromide (46.5 mg, 63.3% yield).

$^1$H NMR (300 MHz, DMSO-d$_6$) δ ppm 8.36-8.41 (m, 2H), 8.24 (d, 1H), 7.89 (dd, 1H), 7.36 (s, 1H), 7.18-7.29 (m, 2H), 6.98-7.05 (m, 1H), 6.87 (d, 1H), 6.77 and 6.79 (d, 1H), 5.46 and 5.49 (d, 1H), 5.21-5.28 (m, 1H), 5.16 and 5.20 (s, 2H), 4.26 and 4.27 (q, 2H), 4.02-4.21 (m, 1H), 3.86 (s, 3H), 3.41-3.82 (m, 5H), 2.15-2.23 and 2.32-2.42 (m, 1H), 1.64-2.15 (m, 4H), 1.29 and 1.30 (t, 3H);

LC-MS (ESI POS): 565.38 (M+).

Example 42

Preparation of (3R)-3-(2-(3-(ethoxycarbonyl)phenylamino)-2-(6-methoxypyridin-3-yl)acetoxy)-1-(2-(isoxazol-3-ylamino)-2-oxoethyl)-1-azoniabicyclo[2.2.2]octane chloride (C70)

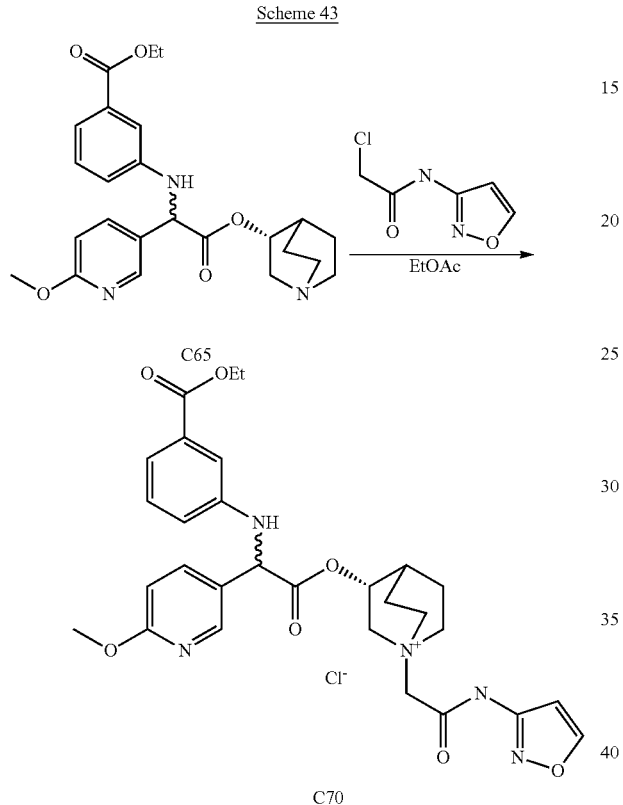

Example 43

Preparation of (3R)-3-(2-(3-(ethoxycarbonyl)phenylamino)-2-(6-methoxypyridin-3-yl)acetoxy)-1-methyl-1-azoniabicyclo[2.2.2]octane iodide (C71)

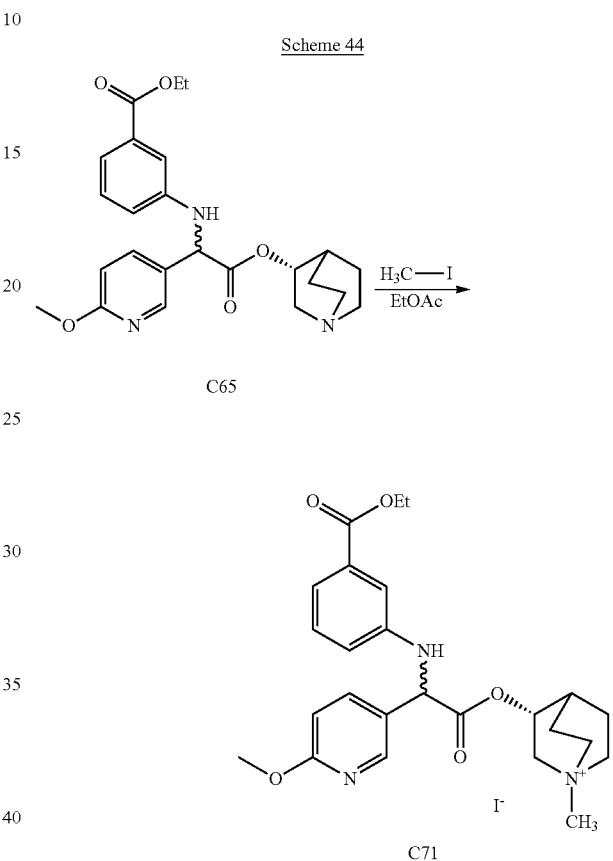

2-Chloro-N-(isoxazol-3-yl)acetamide (18.3 mg, 0.11 mmol) was added to a solution of ethyl 3-(1-(6-methoxypyridin-3-yl)-2-oxo-2-((R)-quinuclidin-3-yloxy)ethylamino)benzoate (C65) (50 mg, 0.11 mmol) in EtOAc (2 ml). The reaction mixture was stirred at room temperature overnight. The solvent was evaporated, and the residue was triturated with Et$_2$O, filtered and dried. The product was purified by preparative HPLC (Eluent: CH$_3$CN/H$_2$O) to obtain (3R)-3-(2-(3-(ethoxycarbonyl)phenylamino)-2-(6-methoxypyridin-3-yl)acetoxy)-1-(2-(isoxazol-3-ylamino)-2-oxoethyl)-1-azoniabicyclo[2.2.2]octane chloride (26.2 mg, 38.4% yield).

$^1$H NMR (300 MHz, DMSO-d$_6$) δ ppm 11.77 (br. s., 1H), 8.85-8.96 (m, 1H), 8.32-8.41 (m, 1H), 7.85-7.93 (m, 1H), 7.31-7.39 (m, 1H), 7.15-7.28 (m, 2H), 6.95-7.05 (m, 1H), 6.73-6.95 (m, 3H), 5.45 and 5.48 (d, 1H), 5.08-5.27 (m, 1H), 3.97-4.38 (m, 5H), 3.85 (s, 3H), 3.39-3.84 (m, 5H), 2.12-2.23 and 2.31-2.40 (m, 1H), 1.58-2.13 (m, 4H), 1.29 and 1.30 (t, 3H);

LC-MS (ESI POS): 564.42 (M+).

Iodomethane (7.1 µl, 0.11 mmol) was added to a solution of ethyl 3-(1-(6-methoxypyridin-3-yl)-2-oxo-2-((R)-quinuclidin-3-yloxy)ethylamino)benzoate (C65) (50 mg, 0.11 mmol) in EtOAc (2 ml). The reaction mixture was stirred at room temperature overnight. The solvent was evaporated, and the residue was triturated with Et$_2$O, filtered and dried. The product was purified by preparative HPLC (Eluent: CH$_3$CN/H$_2$O) to obtain (3R)-3-(2-(3-(ethoxycarbonyl)phenylamino)-2-(6-methoxypyridin-3-yl)acetoxy)-1-methyl-1-azoniabicyclo[2.2.2]octane iodide (24.3 mg, 36.7% yield).

$^1$H NMR (300 MHz, DMSO-d$_6$) δ ppm 8.35 (d, 1H), 7.74-7.93 (m, 1H), 7.33 (t, 1H), 7.18-7.29 (m, 2H), 6.92-7.05 (m, 1H), 6.86 and 6.88 (d, 1H), 6.75 and 6.78 (d, 1H), 5.41 and 5.44 (d, 1H), 4.96-5.24 (m, 1H), 4.28 (q, 2H), 3.85 and 3.86 (s, 3H), 3.69-3.94 (m, 1H), 3.40 (m, 4H), 3.06-3.25 (m, 1H), 2.91 and 2.96 (s, 3H), 2.09-2.19 (m, 1H), 1.77-2.04 (m, 3H), 1.59-1.77 and 2.25-2.35 (m, 1H), 1.30 (t, 3H);

LC-MS (ESI POS): 454.36 (M+).

Example 44

Preparation of (3R)-3-(2-(3-(ethoxycarbonyl)phenylamino)-2-(6-methoxypyridin-3-yl)acetoxy)-1-(3-methylbut-2-enyl)-1-azoniabicyclo[2.2.2]octane bromide (C72)

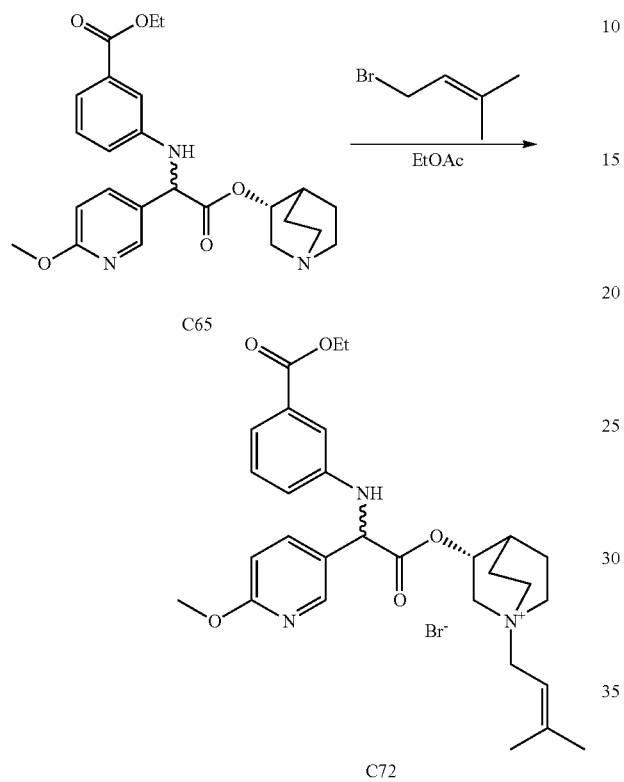

1-Bromo-3-methylbut-2-ene (16.9 mg, 0.11 mmol) was added to a solution of ethyl 3-(1-(6-methoxypyridin-3-yl)-2-oxo-2-((R)-quinuclidin-3-yloxy)ethylamino)benzoate (C65) (50 mg, 0.11 mmol) in EtOAc (2 ml). The reaction mixture was stirred at room temperature overnight. The solvent was evaporated, and the residue was triturated with Et$_2$O, filtered and dried. The product was purified by flash-chromatography (DCM/MeOH=97/3 to 9/1) to obtain (3R)-3-(2-(3-(ethoxycarbonyl)phenylamino)-2-(6-methoxypyridin-3-yl)acetoxy)-1-(3-methylbut-2-enyl)-1-azoniabicyclo[2.2.2]octane bromide (56 mg, 84% yield).

$^1$H NMR (300 MHz, DMSO-d$_6$) δ ppm 8.35 (d, 1H), 7.78-7.92 (m, 1H), 7.31-7.39 (m, 1H), 7.18-7.30 (m, 2H), 6.94-7.08 (m, 1H), 6.87 and 6.88 (d, 1H), 6.76 and 6.78 (d, 1H), 5.42 and 5.45 (d, 1H), 5.23 (t, 1H), 5.07-5.18 (m, 1H), 4.28 (q, 2H), 3.85 and 3.86 (s, 3H), 3.70-3.84 (m, 3H), 3.33-3.45 (m, 2H), 3.12-3.25 (m, 2H), 2.81-3.03 (m, 1H), 1.85-2.37 (m, 3H), 1.81 and 1.82 (br. s., 3H), 1.70 and 1.74 (s, 3H), 1.52-1.77 (m, 2H), 1.30 (t, 3H);

LC-MS (ESI POS): 508.44 (M+).

Example 45

Preparation of (3R)-3-(2-(3-ethylphenylamino)-2-(6-methoxypyridin-3-yl)acetoxy)-1-(2-oxo-2-phenylethyl)-1-azoniabicyclo[2.2.2]octane chloride (C75)

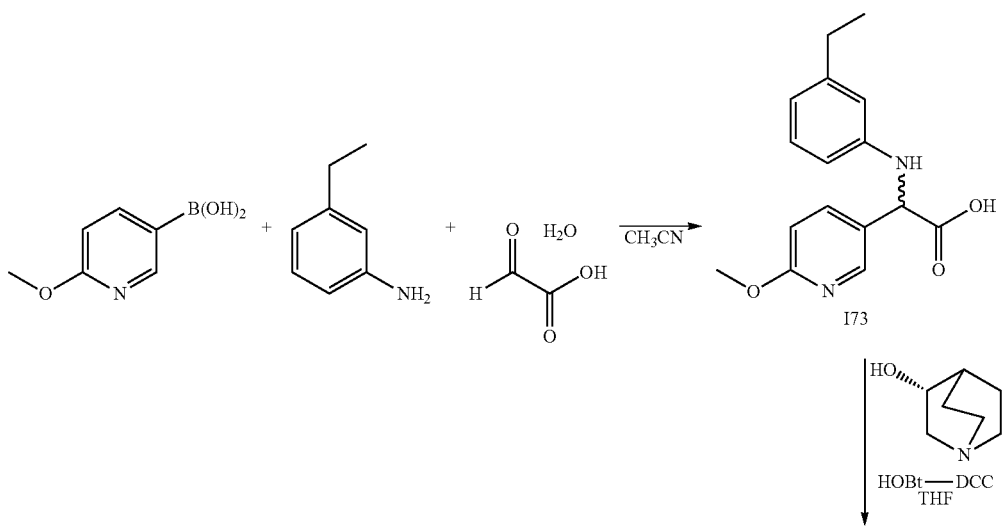

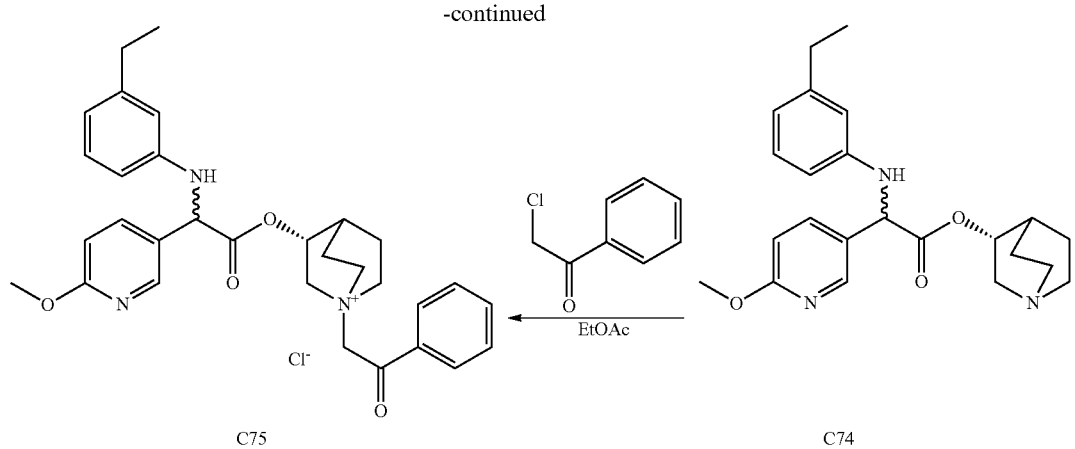

Preparation of 2-(3-ethylphenylamino)-2-(6-methoxypyridin-3-yl)acetic acid (I73)

A mixture of 6-methoxypyridin-3-ylboronic acid (200 mg, 1.31 mmol), 3-ethylaniline (163 μl, 1.31 mmol), and 2-oxoacetic acid hydrate (120 mg, 1.31 mmol) in acetonitrile (20 ml) was stirred at room temperature overnight. The solvent was evaporated, and the crude product was purified by flash-chromatography (DCM/MeOH=9/1) to obtain 2-(3-ethylphenylamino)-2-(6-methoxypyridin-3-yl)acetic acid (265 mg, 70.8% yield).

Preparation of (R)-quinuclidin-3-yl 2-(3-ethylphenylamino)-2-(6-methoxypyridin-3-yl)acetate (C74)

A mixture of 2-(3-ethylphenylamino)-2-(6-methoxypyridin-3-yl)acetic acid (I73) (265 mg, 0.93 mmol), (R)-quinuclidin-3-ol (129 mg, 1.02 mmol), 1H-benzo[d][1,2,3]triazol-1-ol hydrate (156 mg, 1.02 mmol), and N,N'-methanediylidenedicyclohexanamine (210 mg, 1.02 mmol) was dissolved in THF (10 ml) and stirred at room temperature overnight. The solvent was evaporated, and the crude product was taken up with EtOAc and washed twice with 2M $K_2CO_3$. The organic phase was dried over $Na_2SO_4$, filtered and evaporated to dryness to obtain the title compound, which was used in the next step without any further purification.

Preparation of (3R)-3-(2-(3-ethylphenylamino)-2-(6-methoxypyridin-3-yl)acetoxy)-1-(2-oxo-2-phenylethyl)-1-azoniabicyclo[2.2.2]octane chloride (C75)

2-Chloro-1-phenylethanone (143 mg, 0.93 mmol) was added to a solution of (R)-quinuclidin-3-yl 2-(3-ethylphenylamino)-2-(6-methoxypyridin-3-yl)acetate (C74) (366 mg, 0.93 mmol) in EtOAc (3 ml), and the resulting reaction was stirred at room temperature overnight. The solvent was evaporated, and the crude product was purified by preparative HPLC (Eluent: $CH_3CN/H_2O$) to obtain (3R)-3-(2-(3-ethylphenylamino)-2-(6-methoxypyridin-3-yl)acetoxy)-1-(2-oxo-2-phenylethyl)-1-azoniabicyclo[2.2.2]octane chloride (69.3 mg, 13.6% yield over two steps).

$^1$H NMR (300 MHz, DMSO-$d_6$) δ ppm 8.37 (t, 1H), 7.93-8.04 (m, 2H), 7.84-7.93 (m, 1H), 7.76 (d, 1H), 7.53-7.70 (m, 2H), 6.96-7.07 (m, 1H), 6.86 and 6.88 (d, 1H), 6.58-6.65 (m, 1H), 6.54 (d, 1H), 6.48 (d, 1H), 5.38 and 5.41 (s, 1H), 5.19-5.30 (m, 1H), 5.10 and 5.16 (s, 2H), 3.98-4.20 (m, 1H), 3.85 and 3.86 (s, 3H), 3.62-3.82 (m, 5H), 2.42-2.48 (m, 2H), 2.14-2.22 and 2.33-2.41 (m, 1H), 1.55-2.13 (m, 4H), 1.13 (t, 3=H);

LC-MS (ESI POS): 514.3 (M+).

Example 46

Preparation of (3R)-3-(2-(3-fluorophenylamino)-2-(6-methoxypyridin-3-yl)acetoxy)-1-(2-oxo-2-phenyl-ethyl)-1-azoniabicyclo[2.2.2]octane chloride (C78)

Scheme 47

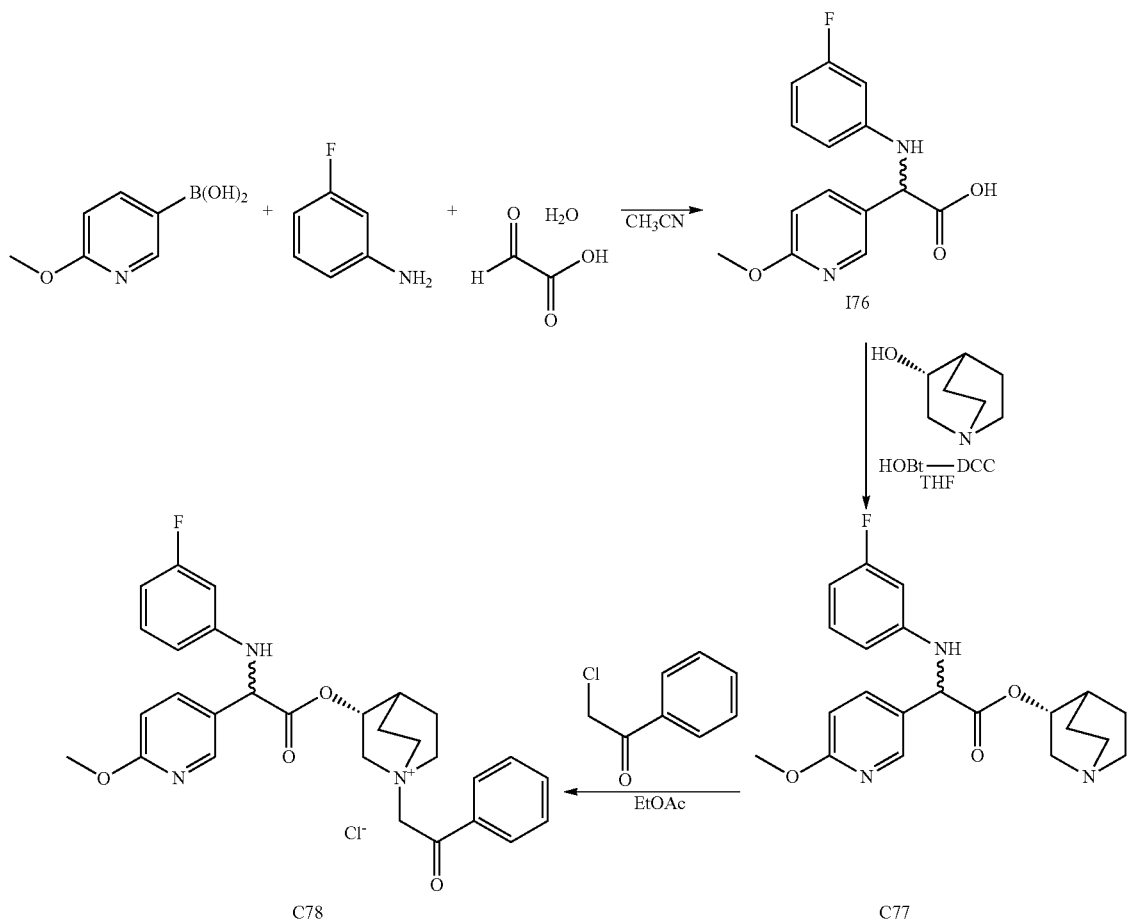

Preparation of 2-(3-fluorophenylamino)-2-(6-methoxypyridin-3-yl)acetic acid (I76)

A mixture of 6-methoxypyridin-3-ylboronic acid (200 mg, 1.31 mmol), 3-fluoroaniline (126 μl, 1.31 mmol) and 2-oxoacetic acid hydrate (120 mg, 1.31 mmol) in acetonitrile (20 ml) was stirred at room temperature overnight. The solvent was evaporated, and the crude product was purified by flash-chromatography (DCM/MeOH=9/1) to obtain 2-(3-fluorophenylamino)-2-(6-methoxypyridin-3-yl)acetic acid (48 mg, 13.3% yield).

Preparation of (R)-quinuclidin-3-yl 2-(3-fluorophenylamino)-2-(6-methoxypyridin-3-yl)acetate (C77)

A mixture of 2-(3-fluorophenylamino)-2-(6-methoxypyridin-3-yl)acetic acid (I76) (48 mg, 0.17 mmol), (R)-quinuclidin-3-ol (24.31 mg, 0.19 mmol), HOBT (29.3 mg, 0.19 mmol), and DCC (39.4 mg, 0.19 mmol) was dissolved in THF (10 ml) and stirred at room temperature overnight. The solvent was evaporated, and the crude product was taken up with EtOAc and washed twice with 2M $K_2CO_3$. The organic phase was dried over $Na_2SO_4$, filtered and evaporated to dryness to obtain the title compound, which was used in the next step without any further purification.

Preparation of (3R)-3-(2-(3-fluorophenylamino)-2-(6-methoxypyridin-3-yl)acetoxy)-1-(2-oxo-2-phenyl-ethyl)-1-azoniabicyclo[2.2.2]octane chloride (C78)

2-Chloro-1-phenylethanone (26.9 mg, 0.17 mmol) was added to a solution of (R)-quinuclidin-3-yl 2-(3-fluorophenylamino)-2-(6-methoxypyridin-3-yl)acetate (C77) (67.1 mg, 0.17 mmol) in EtOAc (3 mL), and the resulting reaction mixture was stirred at room temperature overnight. The solvent was evaporated, and the crude product was purified by flash chromatography (DCM/MeOH=97/3 to 9/1) and then by preparative HPLC (Eluent: $CH_3CN/H_2O$) to obtain (3R)-3-(2-(3-fluorophenylamino)-2-(6-methoxypyridin-3-yl)acetoxy)-1-(2-oxo-2-phenylethyl)-1-azoniabicyclo[2.2.2]octane chloride (19.5 mg, 20.7% yield).

$^1$H NMR (300 MHz, DMSO-$d_6$) δ ppm 8.33-8.43 (m, 1H), 7.91-8.03 (m, 2H), 7.86 and 7.88 (dd, 1H), 7.70-7.81 (m, 1H), 7.54-7.68 (m, 2H), 7.01-7.21 (m, 1H), 6.88 (d, 1H), 6.76 (br. s., 1H), 6.51-6.61 (m, 2H), 6.32-6.45 (m, 1H), 5.39-5.60 (m, 1H), 5.21-5.34 (m, 1H), 5.12 and 5.17 (s, 2H), 4.06-4.19 (m, 1H), 3.85 and 3.86 (s, 3H), 3.58-3.81 (m, 5H), 2.14-2.24 and 2.32-2.42 (m, 1H), 1.48-2.14 (m, 4H);

LC-MS (ESI POS): 504.28 (M+).

Example 47

Preparation of (3R)-3-(2-(2-(methoxycarbonyl)phenylamino)-2-(6-methoxypyridin-3-yl)acetoxy)-1-(2-oxo-2-phenylethyl)-1-azoniabicyclo[2.2.2]octane chloride (C81)

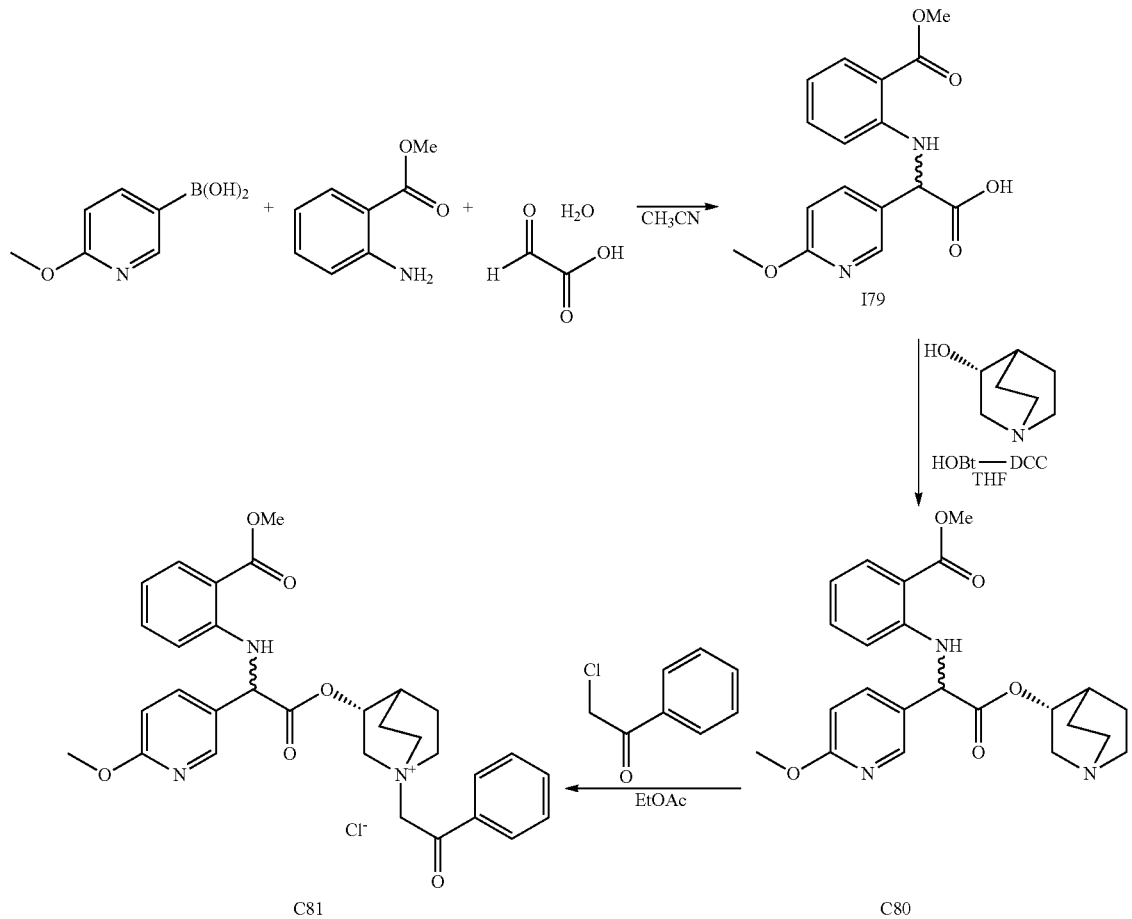

Scheme 48

Preparation of 2-(2-(methoxycarbonyl)phenylamino)-2-(6-methoxypyridin-3-yl)acetic acid (I79)

A mixture of 6-methoxypyridin-3-ylboronic acid (200 mg, 1.31 mmol), methyl 2-aminobenzoate (170 µl, 1.31 mmol), and 2-oxoacetic acid hydrate (120 mg, 1.31 mmol) in acetonitrile (20 ml) was stirred at room temperature overnight. The solvent was evaporated, and the crude product was purified by flash-chromatography (DCM/MeOH=9/1) to obtain 2-(2-(methoxycarbonyl)phenylamino)-2-(6-methoxypyridin-3-yl)acetic acid (118 mg, 28.5% yield).

Preparation of methyl 2-(1-(6-methoxypyridin-3-yl)-2-oxo-2-((R)-quinuclidin-3-yloxy)ethylamino)benzoate (C80)

A mixture of 2-(2-(methoxycarbonyl)phenylamino)-2-(6-methoxypyridin-3-yl)acetic acid (I79) (118 mg, 0.37 mmol), (R)-quinuclidin-3-ol (52.2 mg, 0.41 mmol), 1H-benzo[d][1,2,3]triazol-1-ol hydrate (62.8 mg, 0.41 mmol), and N,N'-methanediylidenedicyclohexanamine (85 mg, 0.41 mmol) was dissolved in dry THF (10 ml) and stirred at room temperature overnight. The solvent was evaporated under reduced pressure, and the crude product was taken up with EtOAc and washed twice with 2M $K_2CO_3$. The organic phase was dried over $Na_2SO_4$, filtered and evaporated to dryness to obtain the title compound, which was used in the next step without any further purification.

Preparation of (3R)-3-(2-(2-(methoxycarbonyl)phenylamino)-2-(6-methoxypyridin-3-yl)acetoxy)-1-(2-oxo-2-phenylethyl)-1-azoniabicyclo[2.2.2]octane chloride (C81)

2-Chloro-1-phenylethanone (57.7 mg, 0.37 mmol) was added to a solution of methyl 2-(1-(6-methoxypyridin-3-yl)-2-oxo-2-((R)-quinuclidin-3-yloxy)ethylamino)benzoate (C80) (159 mg, 0.37 mmol) in EtOAc (3 ml), and the resulting reaction mixture was stirred at room temperature overnight. The solvent was evaporated and the crude was purified first by flash chromatography (DCM/MeOH=97/3 to 9/1), then by preparative HPLC (Eluent: $CH_3CN/H_2O$) and finally by flash chromatography (DCM/MeOH=95/5) to obtain (3R)-3-(2-(2-(methoxycarbonyl)phenylamino)-2-(6-methoxypyridin-3-yl)acetoxy)-1-(2-oxo-2-phenylethyl)-1-azoniabicyclo[2.2.2]octane chloride (21.2 mg, 9.8% yield).

$^1$H NMR (300 MHz, DMSO-d$_6$) δ ppm 8.76 (d, 1H), 8.37 (t, 1H), 7.90-8.08 (m, 2H), 7.83-7.91 (m, 1H), 7.72-7.83 (m, 2H), 7.50-7.66 (m, 2H), 7.30-7.44 (m, 1H), 6.89 (d, 1H), 6.62-6.72 (m, 2H), 5.65 and 5.70 (d, 1H), 5.22-5.35 (m, 1H), 5.13 and 5.17 (s, 2H), 3.98-4.26 (m, 1H), 3.86 (s, 3H), 3.85 (s, 3H), 3.52-3.76 (m, 5H), 2.20-2.46 (m, 1H), 1.62-2.17 (m, 4H);

LC-MS (ESI POS): 544.31 (M+).

Biological Characterisation

Example 48

Examples of Radioligand Binding Assay for Cloned Human Muscarinic Receptors

CHO-K1 clone cells expressing the human M1-, M2-, and M3-receptors (Euroscreen, Swissprot P11229, P08172, P20309, Genbank: J02960 respectively) were harvested in Ca$^{++}$/Mg$^{++}$ free phosphate-buffered saline and collected by centrifugation at 1500 rpm for 10 minutes, at 4° C. The pellets were resuspended in ice cold buffer A (15 mM Tris-HCl pH 7.4, 2 mM MgCl$_2$, 0.3 mM EDTA, 1 mM EGTA). Cloned cells expressing M1-, M2-, and M3-receptors were homogenized by a PBI politron (setting 5 for 15 s). The crude membrane fraction was collected by two consecutive centrifugation steps at 40000 g for 20 minutes at 4° C., separated by a washing step in buffer A. The pellets obtained from the three cell lines were finally resuspended in buffer C (75 mM Tris HCl pH 7.4, 12.5 mM MgCl$_2$, 0.3 mM EDTA, 1 mM EGTA, 250 mM sucrose) and aliquots were stored at −80° C.

The day of experiment, M1-, M2-, and M3-receptor frozen membranes were resuspended in buffer D (50 mM Tris-HCl pH 7.4, 2.5 mM MgCl$_2$, 1 mM EDTA). The non selective muscarinic radioligand [3H]-N-methyl scopolamine (see Mol. Pharmacol., 45:899-907, which is incorporated herein by reference in its entirety) was used to label the M1, M2, and M3 binding sites. Binding experiments were performed in duplicate (ten point concentrations curves) in 96 well plates at radioligand concentration of 0.1-0.3 nM. The non specific binding was determined in the presence of cold N-methyl scopolamine 10 µM. Samples (final volume 0.75 ml) were incubated at RT for 120 minutes for M1, 60 min for M2 and 90 min for M3 binding assay. The reaction was terminated by rapid filtration through GF/B Unifilter plates and two washes (0.75 ml) with cold buffer using a Packard Filtermate Harvester. Radioactivity on the filters was measured by a microplate scintillation counter TopCount NXT (Canberra Packard).

In the present assays, Ki values for the tested compounds were determined from the observed IC50 values according to known methods. A lower Ki value indicates that the tested compound has a higher binding affinity for the receptor.

The Ki values of the tested compounds of the invention are comprised between 0.1 nM and 1 µM.

The interaction with M3 muscarinic receptors can be estimated by the results of in vitro studies which evaluated the potency of the test compounds and the offset of the inhibitory activity produced after washout of the antagonists in isolated guinea pig trachea.

Example 49

In Vitro Interaction with Guinea Pigs M3 Receptors

The potency of the antagonist activity in isolated guinea pig trachea was investigated following a method previously described by Haddad E B et al., in Br. J. Pharmacol., 127, 413-420, 1999, which is incorporated herein by reference in its entirety, with few modifications.

A cumulative concentration-response curve to test antagonists was constructed on preparations precontracted by carbachol, until a complete inhibition of smooth muscle tone was achieved. The concentration of antagonist producing a 50% reversal of carbachol-induced tonic contraction (IC$_{50}$) was taken as a measure of its potency in this bioassay.

In the experiments aiming at assessing the offset of the inhibitory effects produced by test compounds, the minimal concentration of the test compounds known to produce a maximal inhibitory effect was administered to carbachol-precontracted preparations. As soon as the tonic contraction was completely reversed, the organ bath solution was renewed and preparations were thoroughly washed with fresh Krebs solution. Carbachol (0.3 µM) was administered again (at 30 minute interval between washout and next administration) during the next 4 hours.

After the administration of carbachol, the inhibitory effects of the compounds of the invention, administered at a concentration of 10 nM, were expressed as percentage of the recovery of the contracting response to carbachol. The percentage of recovery four hours after the washout was lower than 50%.

The IC$_{50}$ values for the tested compounds are comprised between 0.1 nM and 300 nM.

Example 50

Plasma Stability

In order to demonstrate that the compounds are degraded, stability in human plasma at 1 and 5 hours was tested for the compound of the invention. Briefly, 10 µl of a stock solution 250 µM of the compound in acetonitrile were added to 1 ml of human plasma and samples were incubated at 37° C. Plasma (50 µL) was taken after 0, 1, and 5 hours of incubation and added to 140 µl of acetonitrile with addition of verapamil as internal standard (250 ng/ml). Samples were analysed by HPLC-MS/MS analysis.

Plasma stability is calculated as percentage remaining after 1 and 5 hours by dividing the peak area at 1 or 5 hours by the area of the peak at time 0.

After 1 and 5 hours of incubation, plasma stability being tested for some representative compounds of the invention result to be comprised between 0 and 25%, indicating that the compounds of the invention are very unstable in human plasma.

Legend
* NMR
s=singlet
d=doublet
t=triplet
q=quartet
dd=doublet of doublets
m=multiplet
br=broad Where a numerical limit or range is stated herein, the endpoints are included. Also, all values and subranges within a numerical limit or range are specifically included as if explicitly written out.

Obviously, numerous modifications and variations of the present invention are possible in light of the above teachings. It is therefore to be understood that, within the scope of the appended claims, the invention may be practiced otherwise than as specifically described herein.

All patents and other references mentioned above are incorporated in full herein by this reference, the same as if set forth at length.

The invention claimed is:
1. A compound of formula (I):

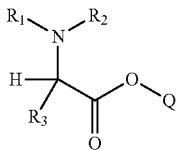

wherein:
- $R_1$ is selected from the group consisting of aryl, heteroaryl, aryl($C_1$-$C_6$)alkyl, and heteroaryl($C_1$-$C_6$)alkyl, each of which may be optionally substituted by one or more substituents selected from the group consisting of halogen atoms, —OH, oxo, —SH, —$NH_2$, —$NO_2$, —CN, —CON($R_5$)$_2$, —NHCOR$_5$, —COR$_5$, —CO$_2R_5$, ($C_1$-$C_6$)alkylsulfanyl, ($C_1$-$C_6$)alkylsulfinyl, ($C_1$-$C_6$)alkylsulfonyl, ($C_1$-$C_6$)alkyl, ($C_1$-$C_6$)haloalkyl, ($C_1$-$C_6$)alkoxy, and ($C_1$-$C_6$)haloalkoxy;
- $R_2$ is H or is selected from the group consisting of ($C_1$-$C_6$)alkyl, ($C_3$-$C_8$)cycloalkyl, and aryl($C_1$-$C_6$)alkyl, each of which may be optionally substituted by one or more substituents selected from the group consisting of halogen atoms, —OH, oxo, —SH, —$NH_2$, —$NO_2$, —CN, —CON($R_5$)$_2$, —NHCOR$_5$, —COR$_5$, —CO$_2R_5$, ($C_1$-$C_6$)alkylsulfanyl, ($C_1$-$C_6$)alkylsulfinyl, ($C_1$-$C_6$)alkylsulfonyl, ($C_1$-$C_6$)alkyl, ($C_1$-$C_6$)haloalkyl, ($C_1$-$C_6$)alkoxy, and ($C_1$-$C_6$)haloalkoxy;
- $R_3$ is selected from the group consisting of phenyl, pyridyl, and benzothiophenyl, each of which may be optionally substituted by one or more substituents selected from the group consisting of halogen atoms, —OH, oxo, —SH, —$NH_2$, —$NO_2$, —CN, —CON($R_5$)$_2$, COR$_5$, CO$_2R_5$, ($C_1$-$C_6$)alkylsulfanyl, ($C_1$-$C_6$)alkylsulfinyl, ($C_1$-$C_6$)alkylsulfonyl, ($C_1$-$C_6$)alkyl, ($C_1$-$C_6$)haloalkyl, ($C_1$-$C_6$)alkoxy and ($C_1$-$C_6$)haloalkoxy, and aryl($C_1$-$C_6$)alkoxy;
- $R_5$, independently in each occurrence, is H or is selected from the group consisting of ($C_1$-$C_6$)alkyl, ($C_2$-$C_6$)alkenyl, ($C_3$-$C_8$)cycloalkyl, heteroaryl, and aryl each of which may be optionally substituted by one or more substituents selected from the group consisting of halogen atoms, —OH, oxo, —SH, —$NH_2$, —$NO_2$, —CN, —CONH$_2$, —COOH, ($C_1$-$C_6$)alkoxycarbonyl, ($C_1$-$C_6$)alkylsulfanyl, ($C_1$-$C_6$)alkylsulfinyl, ($C_1$-$C_6$)alkylsulfonyl, ($C_1$-$C_6$)alkyl, ($C_1$-$C_6$)haloalkyl, ($C_1$-$C_6$)alkoxy, and ($C_1$-$C_6$)haloalkoxy;
- Q represents a group of formula (i) or (ii)

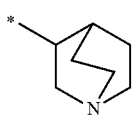

(i)

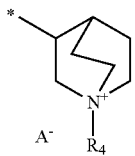

(ii)

wherein $R_4$ is a group of formula (Y):

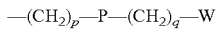

(Y)

wherein
p is 0 or an integer of 1 to 4;
q is 0 or an of from 1 to 4;

P is absent or is selected from the group consisting of —O—, —S—, —SO—, —$SO_2$!—CO—, —NR$_5$—, —CH═CH—, —N($R_5$)$SO_2$—, —N($R_5$)COO—, —N($R_5$)C(O)—, —$SO_2$N($R_5$)—, —CO(O)N($R_5$)—, and —C(O)N($R_5$)—;

W is H or is selected from the group consisting of ($C_1$-$C_6$)alkyl, ($C_2$-$C_6$)alkenyl, $C_3$-$C_8$)cycloalkyl, aryl, and heteroaryl, each of which may be optionally substituted by one or more substituents selected from the group consisting of halogen atoms, —OH, oxo, —SH, —$NH_2$, $NO_2$, —CN, —CON($R_5$)$_2$, —NHCOR$_5$, —COR$_5$, —CO$_2R_5$, ($C_1$-$C_6$)alkyl, ($C_1$-$C_6$)alkylsulfanyl, ($C_1$-$C_6$)alkylsulfinyl, ($C_1$-$C_6$)alkylsulfonyl, ($C_1$-$C_6$)alkyl, ($C_1$-$C_6$)haloalkyl, ($C_1$-$C_6$)alkoxy, and ($C_1$-$C_6$)haloalkoxy;

$A^-$ is a physiologically acceptable anion;
or a pharmaceutically acceptable salt thereof;
wherein at least one between $R_1$ and $R_3$ is a heteroaryl group.

2. A compound or salt thereof according to claim 1, wherein $R_1$ is selected from the group consisting of aryl, heteroaryl, and aryl($C_1$-$C_6$)alkyl, each of which may be optionally substituted by one or more substituents selected from the group consisting of halogen atoms, —COR$_5$, —CO$_2R_5$, —CON($R_5$)$_2$, ($C_1$-$C_6$)alkyl, and ($C_1$-$C_6$)alkoxy; $R_2$ is H or ($C_1$-$C_6$)alkyl; and Q is a group of formula (i).

3. A compound or salt thereof according to claim 1, wherein $R_1$ is selected from the group consisting of phenyl, benzyl, and thiophenyl, each of which may be optionally substituted by one or more substituents selected from the group consisting of halogen atoms, —COR$_5$, —CO$_2R_5$, —CON($R_5$)$_2$, ($C_1$-$C_6$)alkyl, and ($C_1$-$C_6$)alkoxy, wherein $R_5$ is H or ($C_1$-$C_6$)alkyl; Q is a group of formula (i); and $R_2$ is H or methyl.

4. A compound or salt thereof according to claim 1, wherein $R_1$ is selected from the group consisting of aryl, heteroaryl, and aryl($C_1$-$C_6$)alkyl, each of which may be optionally substituted by one or more substituents selected from the group consisting of halogen atoms, —COR$_5$, —CO$_2R_5$, —CON($R_5$)$_2$, ($C_1$-$C_6$)alkyl, and ($C_1$-$C_6$)alkoxy; $R_2$ is H or ($C_1$-$C_6$)alkyl; and Q is a group of formula (ii).

5. A compound or salt thereof according to claim 1, wherein $R_1$ is selected from the group consisting of phenyl, benzyl, and thiophenyl, each of which may be optionally substituted by one or more substituents selected from the group consisting of halogen atoms, —COR$_5$, —CO$_2R_5$, —CON($R_5$)$_2$, —($C_1$-$C_6$)alkyl, and —($C_1$-$C_6$)alkoxy, wherein $R_5$ is H or ($C_1$-$C_6$)alkyl; and Q is a group of formula (ii).

6. A compound or salt thereof according to claim 1, wherein $R_3$ is selected from the group consisting of aryl and heteroaryl, each of which may be optionally substituted by one or more substituents selected from the group consisting of halogen atoms, ($C_1$-$C_6$)alkoxy, —OH, and aryl($C_1$-$C_6$)alkoxy; Q is a group of formula (i); and $R_2$ is H or ($C_1$-$C_6$)alkyl.

7. A compound or salt thereof according to claim 1, wherein Q is a group of formula (i).

8. A compound or salt thereof according to claim 1, wherein $R_3$ is selected from the group consisting of aryl and heteroaryl, each of which may be optionally substituted by one or more substituents selected from the group consisting of halogen atoms, ($C_1$-$C_6$)alkoxy, —OH, and aryl($C_1$-$C_6$)alkoxy; Q is a group of formula (ii); and $R_2$ is H or ($C_1$-$C_6$)alkyl.

9. A compound or salt thereof according to claim 1, wherein Q is a group of formula (ii).

10. A compound or salt thereof according to claim 1, wherein Q is a group of formula (ii); $R_4$ is a group of formula (Y) wherein p is 0, 1, 2, or 3, q is 0, P is absent or is selected from the group consisting of —O—, —CO—, and —C(O)N($R_5$)—, and W is selected from the group consisting of aryl, ($C_2$-$C_6$)alkenyl, and heteroaryl, each of which may be optionally substituted by one or more substituents as described above.

11. A compound or salt thereof according to claim 1, wherein Q is a group of formula (ii); p is 1, q is 0, P is —CO—, and W is selected from the group consisting of phenyl, pyridyl, thiophenyl, isoxazolyl, and thiazolyl, each of which may be optionally substituted as described above.

12. A compound or salt thereof according to claim 1, wherein Q is a group of formula (ii); p is 3, q is 0, P is —O—, and W is phenyl optionally substituted as described above.

13. A compound or salt thereof according to claim 1, wherein Q is a group of formula (ii); p is 2, q is 0, P is absent, and W is phenyl optionally substituted as described above.

14. A compound or salt thereof according to claim 1, wherein Q is a group of formula (ii); p is 1, q is 0, P is —CON(H)—, and W is pyridyl optionally substituted as described above.

15. A compound or salt thereof according to claim 1, wherein Q is a group of formula (ii); p and q are 0, P is absent, and W is methyl.

16. A pharmaceutical composition, comprising at least one compound of formula (I) or salt thereof according to claim 1 and one or more pharmaceutically acceptable carriers and/or excipients.

17. A pharmaceutical composition according to claim 16, which is in a form suitable to be administered by inhalation.

18. A pharmaceutical composition according to claim 17, which is an inhalable powder, a propellant-containing metering aerosol, or a propellant-free inhalable formulations.

19. A method for the treatment of a broncho-obstructive disease, comprising administering an effective amount of a compound or salt thereof according to claim 1 to a subject in need thereof, wherein said broncho-obstructive diseases is asthma, chronic bronchitis, or chronic obstructive pulmonary disease.

20. A combination, which comprises at least one compound of formula (I) or salt thereof according to claim 1 and one or more active ingredients selected from the group consisting of a beta2-agonist, a corticosteroid, a P38 MAP kinase inhibitor, a IKK2 inhibitor, an HNE inhibitor, a PDE4 inhibitor, a leukotriene modulator, a NSAID, and a mucus regulator.

21. A device, comprising a pharmaceutical composition according to claim 19.

22. A device according to claim 21, which is a single- or multi-dose dry powder inhaler, a metered dose inhaler, or a soft mist nebulizer.

* * * * *